United States Patent
Christeller et al.

(10) Patent No.: US 6,972,350 B1
(45) Date of Patent: Dec. 6, 2005

(54) PEST-RESISTANT PLANTS COMPRISING A CONSTRUCT ENCODING A VACUOLE TARGETING SEQUENCE AND AVIDIN OR STREPTAVIDIN

(75) Inventors: John Tane Christeller, Palmerston North (NZ); Paul William Sutherland, Auckland (NZ); Colleen Murray, Palmerston North (NZ); Ngaire Patricia Markwick, Auckland (NZ); Bruce Allan Philip, Auckland (NZ); Louise Anne Malone, Auckland (NZ); Elisabeth Phyllis June Burgess, Auckland (NZ); Margaret Mary Phung, deceased, late of Palemerston North (NZ); by Tammy Sherrie Fongsavanh, legal representitive, Lower Hutt (NZ)

(73) Assignee: The Horticulture and Food Research Institute of New Zealand, Palmerston North (NZ)

( * ) Notice: Subject to any disclaimer, the term of this patent is extended or adjusted under 35 U.S.C. 154(b) by 0 days.

(21) Appl. No.: 09/743,690

(22) PCT Filed: Jul. 15, 1999

(86) PCT No.: PCT/NZ99/00110

§ 371 (c)(1),
(2), (4) Date: May 11, 2001

(87) PCT Pub. No.: WO00/04049

PCT Pub. Date: Jan. 27, 2000

(30) Foreign Application Priority Data

Jul. 15, 1998 (NZ) ................................. 331002

(51) Int. Cl.[7] ............................ A01H 5/00; A01H 5/10; C12N 15/82; C12N 15/62; C12P 21/02
(52) U.S. Cl. ...................... 800/302; 800/279; 536/23.4; 435/320.1; 435/418; 435/70.1; 424/93.2
(58) Field of Search ................................. 800/279, 302, 800/288; 435/320.1, 70.1, 418, 419; 424/93.2; 536/23.4, 23.1

(56) References Cited

U.S. PATENT DOCUMENTS

| | | | |
|---|---|---|---|
| 5,168,049 A | | 12/1992 | Meade et al. |
| 5,276,269 A | | 1/1994 | Raikhel |
| 5,360,726 A | * | 11/1994 | Raikhel ...................... 800/287 |
| 5,525,713 A | | 6/1996 | Raikhel |
| 5,889,174 A | | 3/1999 | Warren et al. |
| 5,908,975 A | | 6/1999 | Caimi et al. |
| 5,990,390 A | | 11/1999 | Lundquist et al. |
| 6,054,637 A | * | 4/2000 | Boller et al. ................. 800/298 |

FOREIGN PATENT DOCUMENTS

| | | |
|---|---|---|
| WO | WO 89/03422 A1 | 4/1989 |
| WO | WO 92/14831 A1 | 9/1992 |
| WO | WO 94/00992 * | 1/1994 |
| WO | WO 96/30530 A1 | 10/1996 |
| WO | WO 96/40949 A1 | 12/1996 |
| WO | WO 98/11235 A2 | 3/1998 |

OTHER PUBLICATIONS

Hill et al, 1998, Biochem. Biophys. Res. Comm. 244:573–577.*
Hilder et al, 1987, Nature 330:160–163.*
Di Sansebastiano, Gian–Pietro et al.; "Specific accumulation of GFP in a non–acidic vacuolar compartment via a C–terminal porpeptide–mediated sorting pathway"; *The Plant Journal*; 1998; pp. 449–457; vol. 15, No. 4.
Farrell, Leigh B, and Roger N. Beachy; "Manipulation of β–glucuronidase for use as a reporter in vacuolar targeting studies"; *Plant Molecular Biology*; 1990; pp. 821–825; vol. 15; Kluwer Academic Publishers; Belgium.
Guan, Xuen and Eve S. Wurtele; "Expression of *Streptavidin* gene in tobacco and its effects on bacteria"; *Plant Physiol*; 1993; p. 45; vol. 102 (suppl.).
Hood, Elizabeth E. et al.; "Molecular farming of industrial proteins from transgenic maize"; *Chemicals via Higher Plant Bioengineering* (Shahidi et al., eds.); 1999; pp. 127–147; Kluwer Academic Publishers; New York.
Hood, Elizabeth E. et al.; "Commercial production of avidin from transgenic maize: characterization of transformant, production, processing, extraction and purification"; *Molecular Breeding*; 1997; pp. 291–306; vol. 3; Kluwer Academic Publishers; Belgium.
Hood, E. E. et al.; "Transgenic com: a new source of valuable industrial products" (ABSTRACT); *Proceedings of the 1998 Corn Utilization and Technology Conference*; Jun. 1–3, 1998; pp. 101–104; Corn Refiniers Association Inc.; U.S.A.
Morgan T. D. et al.; "Avidin and streptavidin as insecticidal and growth inhibiting dietary proteins"; *Entomol. exp. appl.*; 1993; pp. 97–108; vol. 69; Kluwer Academic Publishers; Belgium.

* cited by examiner

*Primary Examiner*—Anne Kubelik
(74) *Attorney, Agent, or Firm*—Townsend and Townsend and Crew LLP

(57) ABSTRACT

This invention relates to nucleic acids encoding chimeric polypeptides comprising vacuole targeting sequences and sequences encoding avidin or streptavidin. The nucleic acids are useful for conferring pest resistance on plants and in the production of compositions useful as pesticides.

21 Claims, 28 Drawing Sheets

```
Sal I    Bam H I

|    |
--------- - pUC 19

|
  Xba I
      1   ATGGAGTCAA AGTTTGCTCA CATCATTGTT TTCTTTCTTC TTGCAACTTC
                                     original sequence   - ag   a
     51   CTTTGAAACT CTCTTGGCAC GAAAAGAAAG Tgatggacca gagatcttag
                                                      mutagenic primer
    101   aacTTCAAAA GGAATTTGAA TGCAATGGAA AACAAAGGTG GCCAGAACTT

151   ATTGGTGTAC CAACAAAGCT TGCTAAGGGG ATAATTGAGA AGGAAAATTC

201   ACTCATAACT AATGTTCAGA TACTACTGAA TGGTTCTCCA GTCACAATGG

251   ATTATCGTTG TAATCGAGTT CGTCTTTTTG ATAACATTTT GGGTGATGTT

301   GTACAAATTC CTAGGGTGGC TTAA
```

Figure 1

```
      1   GAATTCCGCA AGGAgcacac ccggctgtcc acctgCTGCA GAGATGGTGC
                        upstream primer
     51   ACGCAACCTC CCCGCTGCTG CTGCTGCTGC TGCTCAGCCT GGCTCTGGTg
              cc       t       original sequence
    101   gctcccggga tccctgccag AAAGTGCTCG CTGACTGGGA AATGGACCAA
             mutagenic primer
    151   CGATCTGGGC TCCAACATGA CCATCGGGGC TGTGAACAGC AGAGGTGAAT

201   TCACAGGCAC CTACATCACA GCCGTAACAG CCACATCAAA TGAGATCAAA

251   GAGTCACCAC TGCATGGGAC ACAAAACACC ATCAACAAGA GGACCCAGCC

301   CACCTTTGGC TTCACCGTCA ATTGGAAGTT TTCAGAGTCC ACCACTGTCT

351   TCACGGGCCA GTGCTTCATA GACAGGAATG GAAGGAGGT CCTGAAGACC

401   ATGTGGCTGC TGCGGTCAAG TGTTAATGAC ATTGGTGATG ACTGGAAAGC

451   TACCAGGGTC GGCATCAACA TCTTCACTCG CCTGCGCACA CAGAAGGAGT

501   GAGGATGGCC CCGCAAAGCC AGCAACAATG CCGGAGTGCT GACACTGCTT
                                                 ↓ Hind III
    551   GTGATATTCC TCCCCAATAA AGCTTG
```

Figure 2

```
          EcoR I
            ↓
  1  GAATTCGCAT ATGGCTGAAG CTGGTATCAC CGGTACTTGG TACAACCAGC

51  TGGGGTCTAC CTTCATCGTT ACCGCTGGTG CTGACGGTGC ACTGACCGGT

101  ACTTACGAAA GCGCTGTTGG TAACGCTGAA AGCCGTTATG TTCTGACCGG

151  TCGTTACGAC TCTGCTCCGG CTACCGACGG TTCTGGTACT GCTCTGGGTT

201  GGACCGTTGC TTGGAAAAAC AACTACCGTA ACGCTCACTC TGCTACCACC

251  TGGTCTGGCC AGTACGTTGG TGGTGCTGAA GCTCGTATCA ACACCCAGTG

301  GCTGCTGACC TCTGGTACCA CCGAAGCTAA CGCTTGGAAA TCTACCCTGG

351  TTGGTCACGA CACGTTCACC AAAGTTAAAC CGTCTGCTGC TTCTATCTAGA
                                                        ↑
                                                      Xba I
```

Figure 3

```
Sal I    altered Bam H I*
   |        |
---------- - pUC 19
   |
 Xba I

1  ATGGATGTTC ACAAGGAAGT TAATTTCGTT GCTTACCTAC TAATTGTTCT

51  TGGTAAGATT TTCCTTTACT CCTTTGTTTT AAAAAATAAA AAAACAAAAA

101  AAATCTTGGT TTATACATAT ATATACACAC AAGTAGTTTT ATTTTTTTCC

151  TTTATATTAT ATTTGTTGTA GGAATATTTC TACTTGTTAG CGTGGTGGAA

201  CATGTTGATG CGAAGATCTG TACTAAAGAA TGTGGTAATC TTGGGTTTGG

251  GATATGCCCA CGTTCAGAAG GAAGTCCGAA AAATCCCATA TGCATCAATT

301  GTTGCTCAGG CTATAAGGGT TGTAATTATT ATAGTGTTTT CGGGAGATTT

351  ATTTGCGAAG GAGAATCTGA CCTAAAAAAC CCAAAAGCTT GCCCCCTAAA

401  TTGTGATACA AATATTGCCT ATTCAAGATG CCCCCATTCA GAAGGAAAAT

451  CGCTAATTTA TCCCACCGGA TGTACCACAT GTTGCACAGG GTACAAGGGT

501  TGCTACTATT TCGGTAAAAA TGGCAAGTTT GTATGCGAAG GAGAGAGTGA

551  TGAACCCAAG GCAAATATGT ACCCTGCAAT GTGA
```

* result of PCR error during isolation of the PPI-II sequence

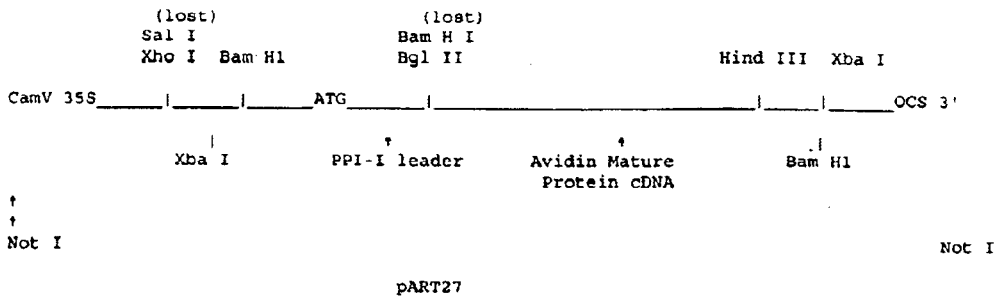

pART27

B)

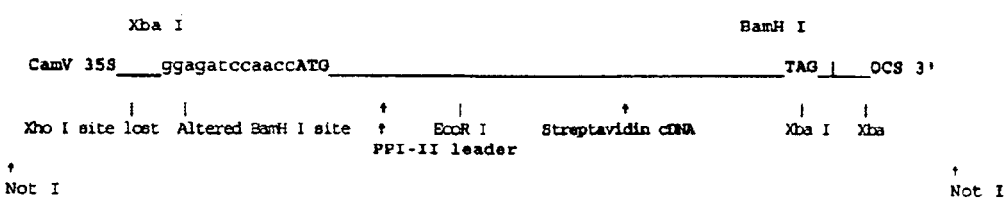

pART27

Figure 7

A)
```
  1 ATGGAGTCAA AGTTTGCTCA CATCATTGTT TTCTTTCTTC TTGCAACTCC
 51 CTTTGAAACT CTCTTGGCAC GAAAAGAAAG TGATGGACCA GAGATCCCTG
101 CCAGAAAGTG CTCGCTGACT GGGAAATGGA CCAACGATCT GGGCTCCAAC
151 ATGACCATCG GGCTGTGAA CAGCAGAGGT GAATTCACAG GCACCTACAT
201 CACAGCCGTA ACAGCCACAT CAAATGAGAT CAAAGAGTCA CCATTGCATG
251 GGACACAAAA CACCATCAAC AAGAGGACCC AGCCCACCTT TGGCTTCACC
301 GTCAATTGGA AGTTTTCAGA GTCCACCACT GTCTTCACGG CCAGTGCTT
351 CATAGACAGG AATGGGAAGG AGGTCCTGAA GACCATGTGG CTGCTGCGGT
401 CAAGTGTTAA TGACATTGGT GATGACTGGA AAGCTACCAG GGTCGGCATC
451 AACATCTTCA CTCGCCTGCG CACACAGAAG GAGTGA
```

B)
```
                 cleavage site
                       ↓
  1 MESKFAHIIV FFLLATPFET LLARKESDGP EipARKCSLT GKWTNDLGSN
 51 MTIGAVNSRG EFTGTYITAV TATSNEIKES PLHGTQNTIN KRTQPTFGFT
101 VNWKFSESTT VFTGQCFIDR NGKEVLKTMW LLRSSVNDIG DDWKATRVGI
151 NIFTRLRTQK E*
```

```
  1  ATGGATGTTC ACAAGGAAGT TAATTTCGTT GCTTACCTAC TAATTGTTCT
 51  TGGTAAGATT TTCCTTTACT CCTTTGTTTT AAAAAATAAA AAAACAAAAA
101  AAATCTTGGT TTATACATAT ATATACACAC AAGTAGTTTT ATTTTTTTCC
151  TTTATATTAT ATTTGTTGTA GGAATATTTC TACTTGTTAG CGTGGTGGAA
201  CATGTTGATG CGAAGATCTG TACTAAGAAT TCGCATATGG CTGAAGCTGG
251  TATCACCGGT ACTTGGTACA ACCAGCTGGG GTCTACCTTC ATCGTTACCG
301  CTGGTGCTGA CGGTGCACTG ACCGGTACTT ACGAAAGCGC TGTTGGTAAC
351  GCTGAAAGCC GTTATGTTCT GACCGGTCGT TACGACTCTG CTCCGGCTAC
401  CGACGGTTCT GGTACTGCTC TGGGTTGGAC CGTTGCTTGG AAAAACAACT
451  ACCGTAACGC TCACTCTGCT ACCACCTGGT CTGGCCAGTA CGTTGGTGGT
501  GCTGAAGCTC GTATCAACAC CCAGTGGCTG CTGACCTCTG GTACCACCGA
551  AGCTAACGCT TGGAAATCTA CCCTGGTTGG TCACNACACG TTCACCAAAG
601  TTAAACCGTC TGCTGCTTCT ATCTAG
```

B)

```
                                     cleavage site
                                           ↓
  1  MDVHKEVNFV AYLLIVLGIF LLVSVVEHVD AKICTKnshM AEAGITGTWY
 51  NQLGSTFIVT AGADGALTGT YESAVGNAES RYVLTGRYDS APATDGSGTA
101  LGWTVAWKNN YRNAHSATTW SGQYVGGAEA RINTQWLLTS GTTEANAWKS
151  TLVGHDTFTK VKPSAASI*
```

```
  1  CCCTCCGTCC CCGCCGGGCA ACAACTAGGG AGTATTTTTC GTGTCTCACA
 51  TGCGCAAGAT CGTCGTTGCA GCCATCGCCG TTTCCCTGAC CACGGTCTCG
101  ATTACGGCCA GCGCTTCGGC AGACCCCTCC AAGGACTCGA AGGCCCAGGT
151  CTCGGCCGCC GAGGCCGGCA TCACCGGCAC CTGGTACAAC CAGCTCGGCT
201  CGACCTTCAT CGTGACCGCG GGCGCCGACG GCGCCCTGAC CGGAACCTAC
251  GAGTCGGCCG TCGGCAACGC CGAGAGCCGC TACGTCCTGA CCGGTCGTTA
301  CGACAGCGCC CCGGCCACCG ACGGCAGCGG CACCGCCCTC GGTTGGACGG
351  TGGCCTGGAA GAATAACTAC CGCAACGCCC ACTCCGCGAC CACGTGGAGC
401  GGCCAGTACG TCGGCGGCGC CGAGGCGAGG ATCAACACCC AGTGGCTGCT
451  GACCTCCGGC ACCACCGAGG CCAACGCCTG GAAGTCCACG CTGGTCGGCC
501  ACGACACCTT CACCAAGGTG AAGCCGTCCG CCGCCTCCAT CGACGCGGCG
551  AAGAAGGCCG GCGTCAACAA CGGCAACCCG CTCGACGCCG TTCAGCAGTA
601  GTCGCGTCCC GGCACCGGCG GGTGCCGGGA CCTCGGCC
```

B)

```
  1  MRKIVVAAIA VSLTTVSITA SASADPSKDS KAQVSAAEAG ITGTWYNQLG
 51  STFIVTAGAD GALTGTYESA VGNAESRYVL TGRYDSAPAT DGSGTALGWT
101  VAWKNNYRNA HSATTWSGQY VGGAEARINT QWLLTSGTTE ANAWKSTLVG
151  HDTFTKVKPS AASIDAAKKA GVNNGNPLDA VQQ
```

PEST-RESISTANT PLANTS COMPRISING A CONSTRUCT ENCODING A VACUOLE TARGETING SEQUENCE AND AVIDIN OR STREPTAVIDIN

FIELD OF THE INVENTION

This invention relates to chimeric polypeptides comprising vacuole targeting sequences and plant-noxious sequences and especially pest control proteins. The polypeptides are useful in methods for targeting non-vacuolar harmful proteins to plant vacuoles. Chimeric polypeptides of the invention containing pest control proteins are useful for conferring pest resistance on plants and in the production of compositions useful as pesticides. The methods and compositions form further aspects of the invention.

BACKGROUND OF THE INVENTION

Expression of proteins in plants is a useful strategy, for producing commercial quantities of a desired protein. Plant expression may avoid problems associated with production of those proteins in animal systems particularly where the protein is required for human therapeutic purposes, and can also be useful for conferring beneficial properties on the plant expression same. Such beneficial properties may include herbicide or pest resistance for example.

However, proteins desirable for expression in plants may themselves be noxious to the plant. That is, they may harm the plant by killing or damaging it or interfering with growth, development and fertility. For example, the protein avidin has been shown to cause male sterility when expressed in plants (WO 96/40949 and WO 99/04023), as has ribonuclease when used under specific promoters (Mariani et al., *Symp. Soc. Exp. Biol.* 45:271–9, 1991).

Accordingly, there is a need for a means of producing desirable plant-noxious proteins in a plant. Organelle targeting of proteins has been contemplated (U.S. Pat. No. 5,792,923). Targeting of foreign proteins to vacuoles has also been contemplated. Vacuole targeting has been applied to increasing accumulation in vacuoles of products which would otherwise be metabolised. U.S. Pat. No. 5,436,394 discusses targeting of invertase to the vacuole as does WO 92/14832. U.S. Pat. No. 5,792,923 discloses plants in which a polyfructan sucrase is targeted to vacuoles. In U.S. Pat. No. 5,723,764 cellulose synthase is targeted to vacuoles. None of these products are plant-noxious. Accordingly, there is no suggestion in any of these documents that vacuole targeting is required to avoid harmful effects on plants.

U.S. Pat. No. 5,360,726 and U.S. Pat. No. 5,525,713 contemplate vacuolar targeting of cereal lectins in leaves and other tissues. Lectins are themselves vacuolar proteins normally located in root tips of adult plants, and specific cells of developing embryos. Lectins are insecticidal proteins. However, there is no suggestion in any of these U.S. parents that vacuolar targeting is necessary or advantageous for production of insecticidal plants.

In WO 98/11235 it is suggested that cellulose degrading enzymes be targeted to vacuoles of transgenic plants to alleviate toxicity problems. However, no data is presented on cellulase activity or localisation of the protein in transgenic plants. Accordingly, there is no data showing vacuolar accumulation occurred and that toxicity was avoided. Therefore, there is still a need for production of transgenic plants in which plant-noxious proteins can be produced without deleterious effects on the plant.

One significant economic area of interest is the use of transgenic plants for pest control.

Pests such as insects, nematodes and mites are a significant economic cost to plant-based industries. Losses arise through production lost to pest consumption, spoilage and introduction of disease carried by pests.

Traditionally, control of pests has been pursued though the application of pesticidal chemicals. Continued use of chemicals is subject to a number of disadvantages. Pests can develop tolerance to chemicals over time producing pesticide resistant populations. Chemical residues may also pose environmental hazards as well as health concerns.

Biological control presents an alternative means of pest control which is potentially more effective and specific than current methods, as well as reducing dependence on chemical pesticides. The need for biological controls has lead to the use of recombinant DNA techniques to insert genes which express pesticidal toxins into plant cells.

This technology in turn may also give rise to resistant pest populations. There is therefore an ongoing need to find proteins with pesticidal properties, particularly those that are encoded by single genes. These genes can be used to transform plants to produce pest resistant cultivars.

Genes studied to date include a range of cry genes from the bacterium *Bacillus thuringiensis* (Bt) encoding β-endotoxins and various his-her plant genes encoding antimetabolites such as protease and α-amylase inhibitors and lectins (Boulter, 1993). Many transgenic cultivars with improved insect resistance are now being commercialised, for example, transgenic cotton, corn, and potatoes (James and Krattiger, 1996).

The commercial production of avidin from reproductive tissue of plants using such constructs has also been contemplated (U.S. Pat. No. 5,767,379). The production methods are subject to a number of drawbacks. Male fertility in plants can be lost and expression in vegetative tissue may be low. This may be due in part to expression being outside the cell.

Most recently, the use of avidin and streptavidin as larvicides against insect pests has been explored (WO 94/00992; Morgan et al. 1993; and Bruins et al., *Insect Biochemistry*, 21: 535–539, 1991). In WO 94/00992 generation of resistant plants has been sought by inserting into the cells of a plant a gene whose expression causes production of one or more of those glycoproteins in larvicidal amounts. While transient expression was shown in maize cells in suspension, no data is presented to show that avidin or streptavidin were expressed at insecticidal concentrations or that plants could be produced expressing same without deleterious side effects.

In later applications by the same applicant as for WO 94/00992, transgenic plants with avidin under control of a promoter are described, see WO 96/40949, WO 99/04023 and U.S. Pat. No. 5,767,379. There is no mention of any of the plants produced in these documents as having insecticidal activity. Moreover, the plants produced all exhibit male sterility. There is no specific suggestion in these documents that vacuole targeting could be used to avoid development of male sterility. Similarly, in *Plant Physiol.* 102 (Suppl.): 45, 1993 a chimeric gene comprising streptavidin coding sequences under control of the CaMV 35S promoter and three signal sequences is contemplated. The signal sequences are indicated as useful for targeting protein to different organelles in plants. However, these organelles are unspecified. Moreover, there is no evidence any plants have been produced incorporating the chimeric genes nor any discussion as to the effects the genes may have on those plants.

The issues with chimeric genes is whether they can be correctly targeted, whether they will be stable in vacuoles, and whether sequestration in a cell vacuole will prevent the protein expressed by the chimeric gene from having deleterious effects on the plant cells.

To date, limited success has been achieved in producing insect resistant plants using this technology.

Specifically, no one has been able to produce a fertile plant expressing significant levels of a biotin-binding protein in vegetative tissues, nor plants shown to be resistant to insect attack due to the expression of a biotin-binding protein. Similarly, no one has yet been able to provide a protein conferring broad spectrum insect resistance on a host plant without deleterious effects to the plant.

It is an object of the present invention to provide chimeric polypeptides and plants which go some way to overcoming the above drawbacks or at least to provide the public with a useful choice.

SUMMARY OF THE INVENTION

Accordingly, in one aspect, the present invention may be broadly said to consist in a chimeric polypeptide that comprises (a) a vacuole targeting sequence encoding a polypeptide; and (b) a sequence encoding a plant-noxious protein linked in operable combination to said targeting polypeptide.

Preferably, the vacuole targeting polypeptide is a signal sequence polypeptide selected from proteinase inhibitor signal sequence (PPI-I or PPI-II) polypeptide which have the amino acid sequences set out in FIG. 8B and FIG. 9B respectively, or variants thereof having substantially equivalent signalling activity thereto.

Preferably, the plant-noxious protein is pest control protein and desirably, a biotin-binding protein.

Preferably, the biotin-binding protein encoded is avidin or streptavidin or a functionally equivalent variant thereof.

The chimeric polypeptides may further comprise at least one additional sequence encoding a protein or peptide.

Conveniently, the chimeric polypeptides of the invention are obtained by expression of a DNA sequence encoding the chimeric polypeptide in a host cell or organism.

In a further aspect, the present invention provides an isolated nucleic acid molecule encoding a chimeric polypeptide of the invention.

This nucleic acid molecule can be an RNA or cDNA molecule but is preferably a DNA molecule.

Also provided by the present invention are recombinant expression vectors which contain a DNA molecule of the invention, and hosts transformed with the vector of the invention capable of expressing a polypeptide of the invention.

In a still further aspect, the invention provides a method of producing a polypeptide of the invention comprising the steps of:
(a) culturing a host cell which has been transformed or transfected with a vector as defined above to express the encoded polypeptide of the invention; and optionally
(b) recovering the expressed polypeptide.

An additional aspect of the present invention provides a ligand that binds to a polypeptide of the invention. Most usually, the ligand is an antibody or antibody binding fragment.

In a further aspect the present invention provides a method for producing a pest resistant plant, comprising transforming the plant genome to include at least one DNA molecule of the invention which includes a sequence encoding a pest control protein.

Also provided is a transgenic plant expressing insecticidally effective concentrations of a pest control protein.

The present invention further provides a transgenic plant that contains a DNA molecule of the invention.

In one embodiment the transgenic plant further contains at least one additional DNA sequence encoding a protein or peptide.

In a still further aspect, the present invention provides a method for controlling or killing pests comprising administering to said pest an amount of a chimeric polypeptide of the invention, which includes a sequence encodine a pest control protein, effective to control or kill said pest.

In one embodiment of the method, the chimeric polypeptide is administered with a second pest control protein, where the combination provides more effective control than administration of the second pest control protein alone.

Usually, the pests are the immature stages of insects, including larvae, grubs, nymphs and instars.

In yet a further aspect, the present invention provides a composition comprising a chimeric polypeptide of the invention and a carrier, diluent, excipient or adjuvant.

In a further composition aspect, the present invention provides a composition comprising plant material produced in accordance with the invention and a carrier, diluent, excipient or adjuvant.

The composition is preferably a pesticidal composition.

In a further aspect the present invention provides a method for controlling or killing pests comprising administering to said pest plant material produced in accordance with the invention, which expresses a pest control protein, or administering a pesticidal composition of the invention, effective to control or kill said pest.

In a still further aspect the present invention provides a method for producing a plat-noxious protein, the method comprising extracting the protein from a plant containing a DNA molecule of the invention coding for same.

While the invention is broadly as defined above, it will be appreciated by those persons skilled in the art that it is not limited thereto and that it also includes embodiments of which the following description gives examples.

FIG. 1 shows the nucleic acid sequence of Potato Proteinase Inhibitor I (PPI-I/pUC19)(SEQ ID NO:1). The signal sequence is in bold type and the start and stop codons are in italic. The mutagenic primer is denoted by underlined in lower case with the Bgl II site created by mutagenesis in bold italic. The upstream and downstream primers used were the Forward and Reverse M13(lacZ) Primers [Perkin Elmer].

FIG. 2 shows Avidin cDNA (pGEMav) (SEQ ID NO:2. The signal sequence represented in bold type, start and stop codons are in italic, primers are underlined lower case with the BamH I site created by mutagenesis in italic. The downstream primer used was the Reverse M13(lacZ) Primer [Perkin Elmer].

FIG. 3 shows streptavidin cDNA (Streptavidin/pUC19) (SEQ ID NO:3). Start and stop codons are in bold type. EcoR I and Xba I sites are in italic.

FIG. 4 shows potato proteinase inhibitor II (PPI-II/pUC19) (SEQ ID NO:4). The signal sequence is represented in bold type and start and stop codons are in bold italic. Underlined type denotes the intron within the signal sequence. The asterisk denotes the result of PCR error during isolation of the PPI-II sequence.

FIG. 5 shows components of the ligation reaction to produce recombinant pART7 containing the PPI-I signal sequence/Avidin cDNA gene fusion. A) PPI-I leader fragment resulting from a Sal I/Bgl II digest of the mutated PPI-I PCR product. B) Avidin mature protein cDNA fragment, resulting from a BamH I/Hind III digest of the mutated Avidin PCR product. C) pART7 vector following an Xho I/Hind III digestion. * denotes compatible cohesive ends. ** denotes compatible cohesive ends.

FIG. 6 shows DNA fragments A, B and C were the components of the ligation reaction to produce recombinant pUC19 containing the PPI-II signal sequence/Streptavidin cDNA gene fusion. The fused gene was then released from pUC19 by a Sal I/BamH I digest and ligation of components D and E produced recombinant pART7. A) PPI-II leader fragment resulting from a Sal I/EcoR I digest of the PPI-II PCR product. B) Streptavidin cDNA fragment, resulting from an EcoR I/Xba I digest of the recombinant plasmid pUC19/Streptavidin cDNA. D) PPI-II signal sequence/Streptavidin cDNA gene fusion fragment, resulting from a Sal/BamH I digest of recombinant pUC19 containing the fused gene. E) pART7 vector following an Xho I/BamH digestion. * denotes compatible cohesive ends.

FIG. 7 shows a schematic representation of the pART7 expression cassette as it was cloned into the pART27 binary vector; A) containing the PPI-I-Avidin gene fusion and B) containing the PPI-II/Streptavidin gene fusion (altered BamH I site=SEQ ID NO:5).

FIG. 8 shows PPI-I/Avidin gene fusion sequence (SEQ ID NO:6) (A) and fusion protein sequence (SEQ ID NO:7)(B): The fusion protein has a total of 161 amino acids; the PPI-I sequence is represented by italic type with bold type denoting the PPI-I signal peptide. Two amino acids, novel to both the PPI-I and the Avidin peptide sequences and represented in lower case, were introduced with the ligation of the Bgl II and BamH I compatible cohesive ends.

FIG. 9 shows PPI-II/Streptavidin gene fusion sequence (SEQ ID NO:8)(A) and fusion protein sequence (SEQ ID NO:9) (B): The fission protein has a total of 168 amino acids; the PPI-II sequence is represented by italic type with bold type denoting the PPI-II signal peptide. Three amino acids, novel to both PPI-II and the Streptavidin peptide sequences and represented in lower case, were introduced at the point of fusion.

FIGS. 10 and 11 show the survival of larvae of the potato moth, *Phthorimaea operculella* fed tobacco plants expressing avidin in two replicate trials.

FIG. 12(A) shows the nucleotide sequence for the gene for streptavidin (SEQ ID NO:10)(Argarana et al. 1986). The signal sequence is represented in bold type, start and stop codons in bold italic. (B) shows the protein sequence for streptavidin (SEQ ID NO:11). The signal sequence is represented in bold type.

FIG. 13 shows a cross section of a transgenic leaf stained with methylene blue/Azure II to show general structure of the leaf. Densely stained bodies in the vacuole are arrowed. Bar=50 μm. v; vascular bundle. t; trichome. g; glandular hair.

FIG. 14 shows immunolabelling of the section for the distribution of avidin (arrowed). Fluorescence indicates the presence of avidin. Bar=50 μm.

FIG. 15 shows a transmission electron micrograph showing the distribution of protein bodies in the vacuole of the cell (arrowed). Bar=1 μm.

FIG. 16 shows a higher magnification of FIG. 15. Immunogold labelling over the surface of the protein bodies within the vacuole (arrowed). Bar=200 nm.

FIG. 46 shows the effect of avidin-painted lettuce leaves on the survival of slugs, *Deroceras reticulatum*.

FIG. 47 shows the effect of avidin expression in tobacco combined with painted-on aprotinin or Cry1Ba on survival of larvae of the cotton bollworm (corn earworm, tomato fruitworm), *Helicoverpa armigera*.

DETAILED DESCRIPTION OF THE INVENTION

Figure 5:
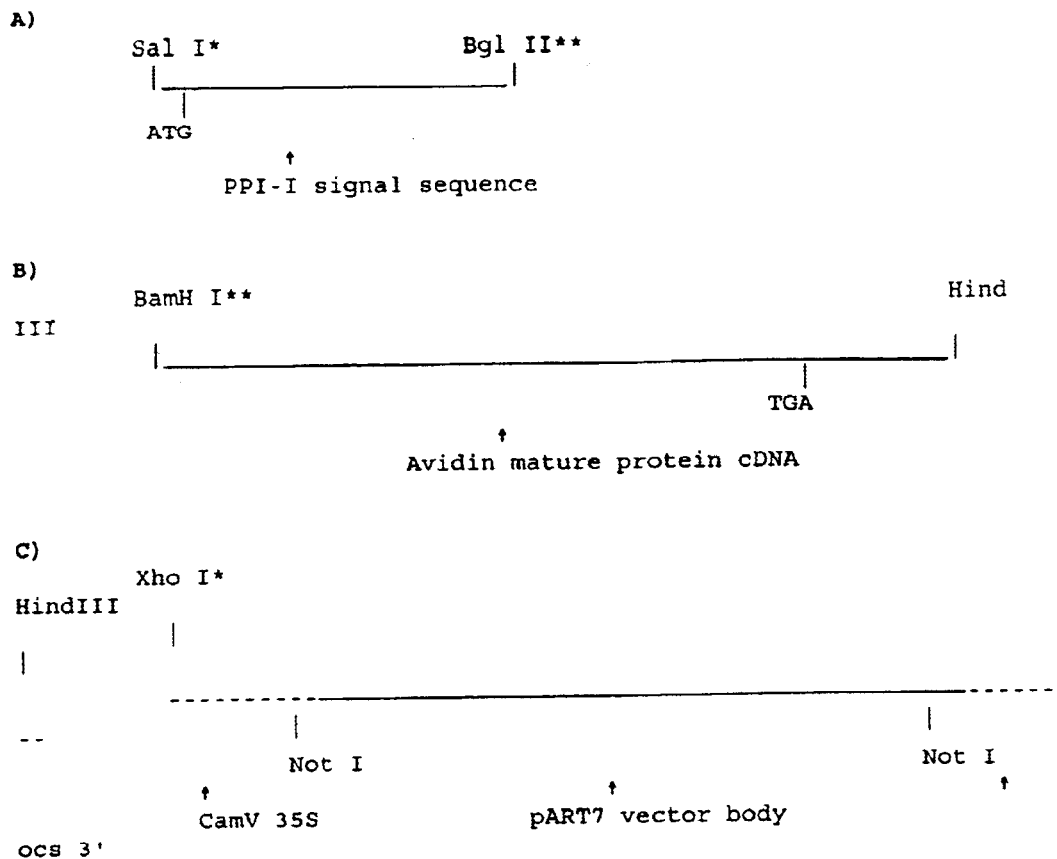

The present invention provides novel chimeric polypeptides comprising vacuole targeting sequences and plant-noxious sequences. The targeting sequences and plant-noxious sequences are operably linked.

The term "operably linked" as used herein refers to a juxtaposition wherein the components so described are in a relationship permitting them to function in their intended manner. For example, a signal sequence is operably linked to a coding sequence if the promoter affects its transcription or expression.

The term "vacuole targeting sequence" as used herein refers to a sequence operable to direct or sort a selected non-vacuolar protein to which such sequence is linked, to a plant vacuole.

The vacuolar targeting polypeptide sequences of the invention, when transformed into plants, function to direct or sort the protein products directed by the expression of genes to which they are operably linked from the cytoplasm to the vacuole of the plant cell. Since the vacuole of plant cells has a storage function, proteins directed there remain there, continually increasing in abundance, unless subject to degradation by vacuolar proteinases. The vacuolar proteins are also isolated from the major metabolic processes in the plant and thus will not interfere with the plant growth and development. The success of the present invention needed that both these requirements be met.

Vacuolar targeting sequences include any such targeting sequences as are known in the art that effect proper vacuole targeting in plant hosts. These include polypeptides targeting barley lectin (Bednarek et al., 1990), sweet potato sporarnin (Matsuoka et al., 1990), tobacco chitinase (Neuhaus et al., 1991), bean phytohemagglutinin (Tague et al. 1990), 2S albumin (Saalbach et al., 1996), aleurain (Holwerda et al., 1992). Vacuolar targeting in plants has been widely studied (for example see Chrispeels, 1991; Chrispeels & Raikhel, 1992; Dromboski & Raikhel, 1996; Kirsch et al., 1994; Nakamura & Matsuoka, 1993; Neilsen et at., 1996; Rusch & Kendall, 1995; Schroder et al., 1993; Vitale & Chrispeels, 1992; von Heijne, 1983). Other sequences are described, for example, in U.S. Pat. No. 5,436,394, U.S. Pat. No. 5,792,923, U.S. Pat. No. 5,360,726, U.S. Pat. No. 5,525,713 and U.S. Pat. No. 5,576,428 incorporated herein by reference. However, potato proteinase inhibitor targeting sequences are preferred.

A number of potato proteinase signal sequence polypeptides designated PPI-I and PPI-II are disclosed for use herein. These polypeptides were described previously (Beuning et al., (1994); Christeller et al. (1994)). The polypeptides have the amino acid sequences set out in FIGS. 8B and 9B respectively. Also encompassed within the invention are variants of these polypeptides and those known in the art which have substantially equivalent targeting sequence activity thereto.

The term "variant" as used herein refers to a polypeptide wherein the amino acid sequence exhibits substantially 70% or greater homology with the amino acid sequences set out in FIGS. 1 and 4. Preferably, the variants will have greater than 85% homology, and most preferably, 95% homology or more. Variants may be arrived at by modification of the native amino acid sequence by such modifications as insertion, substitution or deletion of one or more amino acids.

As noted above, the chimeric polypeptide comprises a vacuole targeting signal sequence operably linked to a plant-noxious protein.

The term "plant-noxious protein" as used herein refers to a protein which has a negative effect on plant health, growth, development or fertility when not sequestered in a plant vacuole.

Examples of plant-noxious proteins include barnase (ribonuclease), cellulases and other cell wall degrading enzymes such as pectinases and polygalacturonases as well as pest control proteins discussed below.

In one embodiment, the plant-noxious protein is a pest control proteins pest control proteins include proteins which decrease availability of vitamins, or other essential growth component or are toxic to pests per se. Toxic proteins include lectins, proteinase inhibitors, *Bacillus thuringiensis* insecticidal proteins, alpha-amylase inhibitors, vegetative insecticidal proteins, lipoxygenase and cholesterol oxidase. Proteins which decrease availability of vitamins fall broadly into these categories of degradative enzymes and binding proteins. Examples of degradative enzymes include thiaminase, riboflavin hydrolase, and pantothenate hydrolase but are not limited thereto.

Bt proteins useful in the present invention include Cry proteins such as Cry1Ba, Cry1Ac, Cry1Cb, Cry1Da, Cry1F, Cry5 and Cry9A, but are not limited thereto.

Proteinase inhibitors useful in the invention include aprotinin, kunitz-type inhibitors from soybean, arrowroot, taro, proteinase inhibitor 1, proteinase inhibitor 2, alpha-1 antitrypsin, Bownan-Birk inhibitors from soybean and cowpea and oryzacystatin.

The term "pest" as used herein refers to a broad group of organisms which at some point in their life cycle live or feed on plants adversely affecting same. Included in the term are protozoa, arthropods (especially insects), aschelminthes and platyhelminthes, nematodes and molluscs.

Binding proteins useful in the invention include riboflavin-binding protein, carotenoid binding proteins, fatty-acid binding proteins, retinol binding proteins, alpha-tocopherol binding proteins, folate-binding proteins, thiamine-binding proteins, pantothenate-binding proteins and biotin-binding proteins, but again are not limited thereto. A preferred group of binding proteins are vitamin binding proteins, particularly biotin-binding proteins. These are proteins which associate with biotin to form a complex with a dissociation constant of $10^{-6}$M or less. Usually, the complex is a non-covalent complex. The biotin binding proteins for use herein must be operable to bind biotin in a plant system without adversely affecting the plant, or to affect the plant in a minimal way, when included in chimeric to polypeptides of the invention. For example, slight reductions in plant growth would be acceptable.

Systems requiring covalent enzymatic sequestration are also contemplated within this term. For example, simultaneous overexpression of a biotin requiring carboxylase or a biotin acceptor peptide (for example, see Schatz, P. J., *Biotechnology*, 11: 1138–1143, (1993) and biotin holocarboxylase synthetase in the vacuole could be used to induce biotin deficiency. Biotin would be covalently sequestered enzymatically on vacuole rupture.

Biotin is an essential nutrient for many species of pests (Dadd R. H., 1985; Kerkut G. A. et al., *Comprehensive Insect Physiology, Biochemistry and Pharmacology*, 4: 313–390, 1985). As discussed above, biotin-binding proteins have been found to have pesticidal properties and to inhibit growth of pests. The binding of biotin causes a biotin deficiency which results in the inhibition of growth and ultimate death of pests.

Biotin-binding proteins known in the art include egg yolk biotin-binding proteins (Subramanial and Ariga 1995, *Biochem J*, 308: 573–577, serum (Seshagiri and Ariga, 1987. *Biochem. Biophys. Acta*, 916: 474431), biotin-binding antibodies, and fragments thereof, biotin holocarboxylase synthetase, biotinidase, bacterial proteins, avidin isolated from egg white, and streptavidin. The properties of a number of these proteins are usefully discussed in *Methods of Enzymology* Vol 184 (eds M. Wilcheta and E A Bayer).

Preferred biotin-binding polypeptides, for use in the present invention, are avidin and streptavidin or functionally equivalent variants thereof. It will be appreciated that other groups that function to bind biotin, such as those referred to above, are equally able to be used in the present invention.

Avidin is a water-soluble tetrameric glycoprotein isolated originally from raw egg white (*J. Biol. Chem* 136: 801 (1940)). The protein is well known with the complete amino acid sequence having been published in, for example, *J. Biol. Chem.* 246: 698 (1971).

The full amino acid sequence for avidin is shown in FIG. 8B (amino acids 34 to 161). Several natural variants of avidin have also been discussed in Keinanen et al., *Eur. J., Biochem*, 220:615–621 (1994) and synthetic variants in Marttila et al., FEBS Letters. 441:313–317 (1998).

Streptavidin is a non-glycosylated bacterial binding protein derived from the culture supernatant of *Streptomyces avidinii* (Bayer et al. 1990). The full amino acid sequence for streptavidin is given in FIG. 12.

'Core' SAV is equivalent to amino acid residues 37–164 of *Streptomyces avidinii* (SAV) FIG. 12, (Argarana et al., 1986). Other 'core' SAV molecules have been produced with various N-terminal and C-terminal deletions. A preferred sequence referred to as "Synthetic 'Core' Streptavidin" is a modified 'core' SAV having the sequence shown in FIG. 9B (amino acids 41 to 168). SYNSAV is equivalent to 'Core' SAV modified such that codons for each amino acid correspond to those in highly expressed *E. coli* genes. SYNSAV is also modified to contain unique restriction sites evenly throughout sequence. The resulting sequence has G+C content of 54% relative to 69% for same region of native SAV (Thompson et al. (1993))[29]. A number of natural variants of streptavidin have also been described in Bayer et al., *Biochem. Biophy. Acta* 1263: 60–66 (1995), GenBank Acc. No. S78782 and S78777. Synthetic streptavidin molecules can also be produced using known art techniques. See for example WO 89/03422.

The chimeric polypeptides of the invention may further comprise one or more sequences encoding other proteins or peptides. Two to four further sequences are contemplated, but more are feasible. These other proteins or peptides may be selected from any proteins known in the art which it is desired to express in a plant vacuole including plant-noxious proteins discussed above.

Proteins to be produced in conjunction with pest control proteins may be selected so as to achieve an additive or synergistic effect as demonstrated in Example 18), a broader spectrum of control, or to reduce the risk of resistance developing. Examples of such proteins include other pest control proteins as discussed above including proteinase inhibitors, toxic proteins and biotin-binding proteins, as well as antimicrobial, antifungal and antiviral proteins but not limited thereto.

Figures 46, 47:
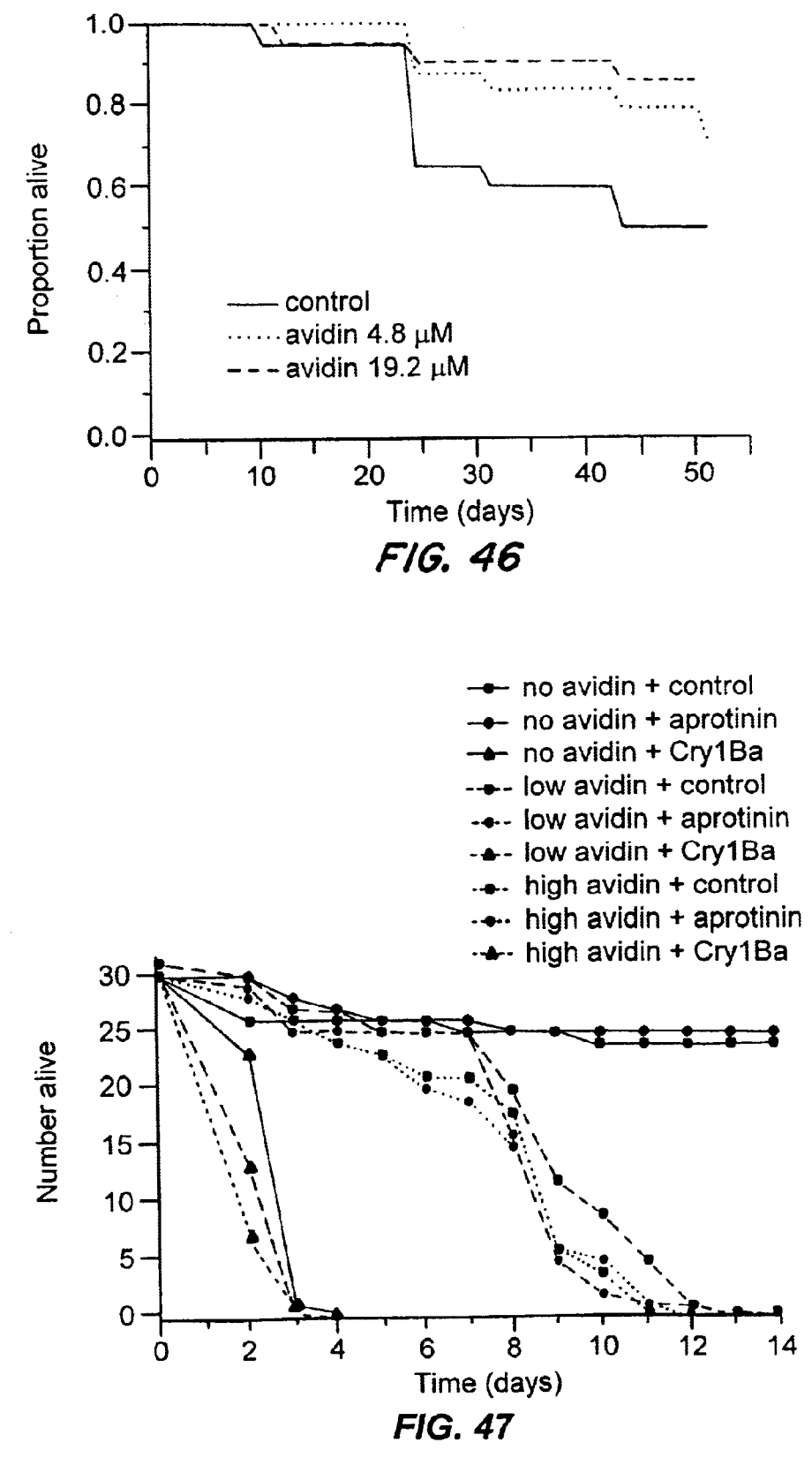

The applicants have surprisingly found that plants expressing avidin when combined with Bt insecticidal protein can exhibit synergistic effects on pests (FIG. 47). Proteinase inhibitors may be desirable for use in preventing proteolysis of the insect control protein (see Example 18) Shao et al., *J Invertebr. Pathol.* 72: 73–81 (1998); and Keller et al., *Insect Biochem. Mol. Biol.* 26: 365–73 (1996). The compatibility of biotin-binding proteins and protease inhibitors has been demonstrated by the applicant.

The antimicrobial, antifungal and antiviral groups of proteins can assist in the control of plant disease particularly where insect damage contributes to the spread of disease. Proteins which have been shown to have these activities include dermaseptins, cercropins, attacins, lysozyme, chitinases, hevein, glucose oxidase, glucanases, thionins, lectins, *Raphanus sativus*, antifungal protein, osmotin, lipid transfer proteins, lipoxygenase and virus coat proteins.

Similarly, reduction in disease from insect resistant crops has been reported. For example, research at Iowa State University has shown reduction in feeding damage is linked to a reduction in earmould in Bt maize.

The reader will appreciate that modifications, including chemical and biochemical modifications, of the polypeptides of the invention are possible. Such modifications include, for example, acetylation, carboxylation, phosphorylation, glycosylation, ubiquitination, labelling, and the like. The production of peptide fragments is also well within the capabilities of an art skilled worker.

The polypeptides of the invention can be prepared in a variety of ways. For example, as indicated above the signal sequences and biotin-binding proteins can be produced by isolation from natural sources and then coupled using techniques known in the art. For example, through recombinant nucleic acid methods.

Synthesis using known techniques (such as stepwise solid phase synthesis described by Merryfield, *J. Amer. Chem.Soc.* Vol 85:2149–2156, 1963), or as preferred through employing recombinant DNA techniques.

Variants of the polypeptide can similarly be made by any of those techniques known in the art. For example, variants can be prepared by site-specific mutagenesis of the DNA encoding the native amino acid sequence as described by Adelman et al. DNA 2:183 (1983). Generally, the variants produced are functionally equivalent to the original sequence.

Where it is preferred, recombinant techniques used to produce the polypeptide of the invention, the first step is to obtain DNA encoding the desired product. Such DNA comprises a still further aspect of this invention.

The DNA of the invention may encode a native or modified polypeptide of the invention or an active fragment thereof. In its presently preferred form, the DNA comprises the nucleotide sequence of FIG. 8A, or the nucleotide sequence of FIG. 9A. Preferred sequences exhibit 60% or greater homology with these sequences, preferably 80% homology and most preferably 95% homology or more. That is, most preferred sequences will hybridise to the sequences of the invention under stringent hybridisation conditions.

The DNA can be isolated from any appropriate natural source or can be produced as intron free cDNA using conventional techniques. DNA can also be produced in the form of synthetic oligonucleotides where the size of the active fragment to be produced permits. By way of example, the Triester method of Matteucci et al. *J. Am. Chem.Soc. Vol* 103:3185–3191 (1981) may be employed.

Where desirable, the DNA of the invention can also code for a chimeric polypeptide of the invention (including polypeptides encoding more than one protein). Such fusion proteins may be produced as disclosed in WO 86/02077 incorporated herein by reference. Fusion proteins further comprising the polypeptide of the invention and a carrier protein are possible. This carrier protein will generally be cleavable from the polypeptide, peptide or fragment under controlled conditions. Examples of commonly employed carrier proteins are galactosidase and glutathione-S-transferase.

As indicated above, also possible are variants of the polypeptide or peptide which differ from the native amino acid sequence by insertion, substitution or deletion of one or more amino acids. Neutral variations (those which have no effect on function) are specifically contemplated. Where such a variant is desired the nucleotide sequence of the native DNA is altered appropriately. This alteration can be made through elective synthesis of the DNA or by modification of the native DNA by, for example, site-specific or cassette mutagenesis. Preferably, where portions of cDNA or genomic DNA require sequence modifications, site-specific primer directed mutagenesis is employed using techniques standard in the art.

In a further aspect, the present invention consists in replicable transfer vectors suitable for use in preparing a polypeptide or peptide of the invention. These vectors may be constructed according to techniques well known in the arL or may be selected from cloning vectors available in the art.

The cloning vector may be selected according to the host or host cell to be used. Useful vectors will generally have the following characteristics:
(a) the ability to self-replicate;
(b) the possession of a single target for any particular restriction endonuclease; and
(c) desirably, carry genes for a readily selectable marker such as antibiotic resistance or herbicide tolerance.

Two major types of vector possessing these characteristics are plasmids and bacterial viruses (bacteriophages or phases). Presently preferred vectors include the plasmids pMOS-Blue, pGem-T, pUC18, pUC19, pART27, pMON, pJIT, pBIN, pRD 400, pART7.

Also contemplated is the use of RNA vectors for example, tobacco mosaic virus (Donson et al., *Proc Natl. Acad. Sci. USA.*, 88:7204–8, 1991), potato virus X (PVX)(Chapman et al., *Plant J.* 2:549–57, 1992), and barley stripe mosaic virus (ESMV) (Josh, et al., *EMBO J.* 9:2663–9, 1990). TMV has previously been used to infect plants to produce therapeutic protein products (Turpen, *Philos Trans. R. Soc. Lond. Biol. Sci.,* 354: 665–73, 1999). Basic RNA vectors can be produced according to known art techniques.

The DNA molecules of the invention may be expressed by placing them in operable linkage with suitable control sequences in a replicable expression vector. Control sequences may include origins of replication, a promoter, enhancer and transcriptional terminator sequences amongst others. The selection of the control sequence to be included in the expression vector is dependent on the type of host or host cell intended to be used for expressing the DNA.

Generally, procaryotic, yeast, insect or mammalian cells are useful hosts. Also included within the term hosts are plasmid vectors. Suitable procaryotic hosts include *E. coli, Bacillus* species and various species of *pseudomonas*. Commonly used promoters such as β-lactamase (penicillinase) and lactose (lac) promoter systems are all well known in the art. Any available promoter system compatible with the host of choice can be used. Vectors used in yeast are also available and well known. A suitable example is the 2 micron origin of replication plasmid.

Similarly, vectors for use in mammalian cells are also well known. Such vectors include well known derivatives of SV-40, adenovirus, retrovirus-derived DNA sequences, *Herpes simplex* viruses, and vectors derived from a combination of plasmid and phage DNA.

Further eucaryotic expression vectors are known in the art (e.g. P. J. Southern and P. Berg, *J. Mol. Appl. Genet.* 1 327–341 (1982); S. Subramani et al., *Mol.Cell.Biol.* 1, 854–864 (1981); R. J. Kaufmann and P. A. Sharp, "Amplification and Expression of Sequences Cotransfected with a Modular Dihydrofolate Reducase Complementary DNA Gene, *J. Mol. Biol.* 159, 601–621 (1982); R. J. Kaufmann and PA. Sharp, *Mol. Cell. Biol.* 159, 601–664(1982); S. I. Scahill et al., "Expressions And Characterization Of The Product Of A Human Immune Interferon DNA Gene In Chinese Hamster Ovary Cells," *Proc. Natl. Acad. Sci. USA.* 80, 4654–4659 (1983); G. Urlaub and L. A. Chasin, *Proc. Natl. Acad. Sci. USA.* 77, 42164220, (1980).

The expression vectors useful in the present invention contain at least one expression control sequence that is operatively linked to the DNA sequence or fragment to be expressed. The control sequence is inserted in the vector in order to control and to rate the expression of the cloned DNA sequence. Examples of useful expression control sequences are the lac system, the trp system, the tac system, the trc system, major operator and promoter regions of phage lambda, the glycolytic promoters of yeast acid phosphatase, e.g. Pho5, the promoters of the yeast alpha-mating factors, and promoters derived from polyoma, adenovirus, retrovirus, and simian virus, e.g. the early and late promoters of SV40, and other sequences known to control the expression of genes of prokaryotic and eucaryotic cells and their viruses or combinations thereof.

Also useful in the present invention are promoters which can be used to target proteins to specific plant tissues. These have application in situations where accumulation of a protein in a particular tissue is desired, or alternatively, is to be avoided to prevent non-target effects. For example, accumulation of an insect control protein in pollen may be undesirable if it is fed on by non target pests such as butterflies, bees or other pollinators. Specific promoters can be used to target such pest control proteins away from pollen.

Alternatively, a target pest may have defined feeding characteristics such as only feeding on leaves, seed, fruit, flowers or the like. In such cases, it would be desirable to target the pest control protein to the plant tissues being feed on, or to particular cells within those tissues. For example, to leaf epidermal cells, root cortex cells, mesophyll cells and the like. Any of the promoters known in the art for targeting specific plant tissues may be employed.

Preferred promoters for use herein include lacZ, CaMV-35S, LHC a/b, T7, nos, rubisco small subunit (SSU), gpd and nod gene promoters.

In the construction of a vector it is also an advantage to be able to distinguish the vector incorporating the foreign DNA from unmodified vectors by a convenient and rapid assay. Such assays include measurable colour changes, antibiotic resistance, herbicide tolerance and the like. In one preferred vector, the β-galactosidase gene is used, which gene is detectable by clones exhibiting a blue phenotype on X-gal plates. This facilitates selection.

Once selected, the vectors may be isolated from the culture using routine procedures such as freeze-thaw extraction followed by purification.

For expression, vectors containing the DNA of the invention to be expressed and control signals are inserted or transformed into a host or host cell. Intermediate host cells can be used to increase the copy number of the cloning vector prior to introduction into plant cells. Some useful expression host cells include well-known prokaryotic and eucaryotic cells. Some suitable prokaryotic hosts include, for example, *E. coli*, such as *E. coli*, S G-936*, E. coli* HB 101, *E. coli* W3110*, E. coli* X1776, *E. coli*, X2282*, E. coli*, DHT, and *E. coli*, MR01*, Pseudomonas, Bacillus*, such as *Bacillus subtilis*, and *Streptomyces*. Suitable eucaryotic cells include yeast and other fungi, insect, animal cells, such as COS cells and CHO cells, human cells and plant cells in tissue culture.

Expression systems employing insect cells utilising the control systems provided by baculovirus vectors have been described (Miller et al., in *Genetic Engineering,* 8: 277–297, 1986).

Depending on the host used, transformation is performed according to standard techniques appropriate to such cells. For prokaryotes or other cells that contain substantial cell walls, the calcium treatment process (Cohen, S. N. *Proceedings, National Academy of Science, USA* 69: 2110, 1972) may be employed. For mammalian cells without such cell walls the calcium phosphate precipitation method of Graeme and Van Der Eb, *Virology* 52:546, 1978 is preferred. Transformations into plants may be carried out using *Agrobacterium tumefaciens* (Shaw et al., *Gene* 23:315, 1983) or into yeast according to the method of Van Solingen et al. *J. Bact.* 130: 946, 1977 and Hsiao et al. *Proceedings, National Academy of Science,* 76: 3829, 1979.

In a preferred transformation process, the vectors of the invention are incorporated into *Agrobacterium tumefaciens* which can be used to infect plant cells, particularly dicotyledenous plant cells, thereby transferring the vectors and conferring pest resistance. The cloning vectors can also be introduced into plant cells using convenient art techniques such as electroporation, microparticle bombardment and microinjection. Microparticle bombardment is the preferred transformation process for monocotyledenous plants. Suitable plant transformation techniques are usefully summarised in Torres et al., Plant Cell, Tissue and Organ Culture 34: 279–285, 1993, Michelmore et al., Plant Cell Reports 6:439–442, 1987, Horsch et al., *Plant Molecular Biology Mammal AS:* 1–9, 1988, Xinrun et al., *J. Genet. and Breed* 46: 287–290, 1992 and WO 97/17455 incorporated herein by reference.

Upon transformation of the selected host with an appropriate vector the polypeptide encoded can be produced, often in the form of fusion protein, by culturing the host cells. The polypeptide of the invention may be detected by rapid assays as indicated above. The polypeptide can then be recovered and purified if desired. Recovery and purification can be achieved using any of those procedures known in the art, for example by absorption onto and elution from an anion exchange resin. This method of producing a polypeptide of the invention constitutes a further aspect of the present invention.

The present invention also provides a method for producing a plant-noxious protein, the method comprising extracting the protein from a plant incorporating a DNA sequence of the invention coding for same. The expression level of the protein may be increased by further incorporating into the DNA sequence of the invention a peptide export signal sequence, or intron sequence. Methods of enhancing expression levels and methods for production of the protein generally may be effected according to the techniques of WO 97/17455 incorporated herein by reference.

The use of the chimeric polypeptides of the present invention represents an advance over this document because the protein is produced in vegetative tissues (leaves, stems, tubers, roots) as opposed to the reproductive tissues. In the case of avidin and streptavidin this avoids the negative effect of male sterility.

The method of the present invention is also significantly more effective than the disclosed art method with avidin produced as levels up to two times higher than previously reported. See Examples 9, 18 and 17.

The applicant has also been the first to achieve expression of streptavidin using this methodology (see Example 7). The expression levels are approximately twice those previously reported for avidin in U.S. Pat. No. 5,767,379.

It is also noted that the avidin and streptavidin expression levels were achieved with selfed plants. Higher levels of expression are anticipated where plants expressing high levels of avidin or streptavidin are crossed.

The method can be used for producing proteins from a wide range of plants which produce abundant vegetative material e.g. potatoes, cassaya, tobacco, grasses, legumes, and trees rather than being restricted to plants which produce large reproductive structures e.g. maize.

In a further aspect, the present invention provides a transgenic plant that contains a DNA molecule of the invention. The plant is produced according to the procedures detailed above, generally comprising transformation with a vector of the invention.

In one embodiment, the transgenic plant contains at least one, and commonly two to four, additional DNA sequences encoding a protein or peptide. More additional sequences are feasible. The proteins or peptides may be any of those proteins or peptides discussed above for the additional protein or peptide within the chimeric polypeptide. Again, sequences encoding Bt Cry proteins are preferred for incorporation into the plant. Incorporation of the additional sequence(s) for the protein(s) or peptide(s) other than as part of the chimeric polypeptide allows for the independent expression of the chimeric polypeptide and additional protein(s) or peptide(s).

Plants suitable for transformation with the vectors of the invention may be selected from a broad range of plants including cereal crops, vegetable, fruit and other food crops, forage crops and turf plants, fibre crops, timber and pulp and paper plants, shelter-belt plants and tree crops, ornaments and flower plants, culinary plants, medicinal plants and herbs and plants grown to produce beverages and plants grown for smoking.

Examples of cereal crops include wheat, rice, barley, maize, oats, millet, sorghum and rye.

Examples of vegetable, fruit and other food crops include root crops such as potato, sweet potato, beetroot, parsnip, turnip, swede and carrot, cucurbits such as cucumbers, pumpkins, squash, marrow, courgettes and watermelon, brassicas such as cauliflower, cabbage, oilseed rape, brussels sprouts and broccoli corn, tomato, lettuce, celery, onions, garlic, legumes such as lentils, green beans, lima beans, haricot beans, red kidney beans, kudzu beans, mung beans, broadbeans, soybeans, chickpeas, peas, and peanuts, apple, pear, kiwifruit, tamarillo, feijoa apricot, plum, citrus such as orange, lemon, tangelo, grapefruit, uglifruit and mandarin, pineapple, peach, nectarine, cherry, berries, olives and sugarcane.

Examples of forage crops and turf plants include legumes such as clover, alfalfa, lotus, trefoil and lucerne and grasses and other graminaceous plants such as ryegrass, browntop, fescue, cocksfoot, kikuyu and, paspalum, and sorghum grass.

Fibre crops include cotton, flax, kapok and hemp.

Timber, shelterbelt, conservation, pulp and paper plants and tree crops include, for example, pine, eucalyptus, spruce, fir, oak, ash, birch, beech, mahogany, rosewood, ebony, maple, teak, cedar, redwood, jarrah, chestnut, walnut, macadamia nut, poplar, willow, cypress, camphor, mulberry, marram grass and rubberplant.

Ornamental shrubs, trees and flower plants include roses, petunias, orchids, carnations, chrysanthemums, daisies, tulips, lilies, gypsophylla, hibiscus, rhododendrons, conifers, camellias, hebes, lavender, lupins, tussock, ferns and native plants.

Culinary plants include herbs such as basil, rosemary, oregano, bay, and spices such as cinnamon, mace, tumeric, and sage.

Medicinal plants include poroporo, opium poppies, coca, marijuana, camomile, comfrey, foxglove and belladonna.

Plants used to produce beverages include tea, coffee, hops and cocoa.

Plants used for smoking include tobacco.

Plants transformed with the vectors of the invention direct expression of the plant-noxious proteins in the vacuoles of the plant cells. The protein is effectively sequestered into the vacuole. Where the protein is a pest control protein, when a pest feeds on the plant expressing a pest control protein, the plant cell components mix together allowing a substance to be controlled (e.g. biotin) to be bound by the binding protein, or alternatively degraded by enzyme (e.g. in the case of thiamine). This essentially deprives the pest of the vitamin it requires leading to stunted growth and death.

The effect of biotin deprivation is often manifested in the failure of the immature stages of the pests to complete the process of moulting from one developmental stage to the next as demonstrated in Examples 6 to 13.

In a further aspect, the invention also provides a transgenic plant expressing pesticidally effective concentrations of pest control protein.

In one preferred aspect, there is provided a plant expressing insecticidally effective concentrations of a biotin-binding protein. Also provided are plants expressing combinations of biotin-binding proteins and other pest control proteins as discussed above.

The present invention has application in producing plants resistant to a broad range of pests in the larval stage including moths, beetles, weevils, caterpillars, borers, budworms, armyworms, bollworms, rootworms, webworms, aphids, bugs, crickets, locusts, grasshoppers, grubs, flies, fruitflies, leafminers, plant hoppers, earwigs, scale insects, thrips, and springtails. Plants of the invention may also be resistant to other invertebrate pests of plants such as mites and lice and other pests and pathogens which have a vitamin requirement especially for biotin, particularly those which undergo a moulting process as part of their development:

List of most Preferred Pests:

Order *Lepidoptera:*
  cotton bollworm (*Helicoverpa armigera*)
  tropical army-worm (*Spodoptera litura*), also *S. littoralis, S. exigua*
  European corn-borer (*Ostrinia nubilalis*)
  tobacco horn worm (*Manduca sexto*)
  loopers (*Chrysodiexis* spp.)
  rice stem borer (*Chilo suppressalis*)
  porina (*Wiseana* spp.)
  cutworms (*Agrotis* spp.)
  diamondback moth (*Plutella xylostella*)
  potato tuber moth (*Phthorimaea operculella*)
  codling moth (*Cydia pomonella*)
  Indian meal moth (*Plodia interpunctella*)
  gypsy moth (*Lymantria dispar*)

Order Coleoptera:
  argentine stem weevil (*Listronotus bonariensisµ*)
  clover root weevil (*Sitona lepidus*)
  grass-grubs (*Costelytra zelandica, Odontria* spp.)
  corn rootworm (*Diabrotica virgifera*)
  rice and wheat weevils (*Sitophilus* spp.)
  mealworms (*Tenebrio molitar*)
  flour beetles (*Tribolium confusum*)

Order Orthoptera:
  black field cricket (*Teleogryllus commodus*)
  locusts (*Locusra migratoria*)

Order *Hymenoptera:*
  Sawflies (*Sirex* spp., *Nematus olgospilus*)

Order *Thysanoptera:*
  Western Flower thrips (*Frankliniella occidentals*)

Order Diptera:
  Hessian flies (*Mayetiola destructor*)

Mites (Class Arachnida)

Order Acari
  two-spotted mite (*Tetranychus urticae*)
  European red mite (*Panonychus ulmi*)

The applicants have also demonstrated that plants of the invention will not cause significant mortality of desirable insects such as adult honeybees feeding on pollen (see Example 14). Some specificity of action is also shown where non-moulting, adult stages of insects such as weevils, and invertebrates that do not moult, such as nematodes, slugs or snails, are unlikely to be harmed by feeding on these plants. Hence, plants produced according to the invention have a broad spectrum of pest resistance for invertebrates that moult, particularly insects, as part of their development process.

In a further aspect the invention provides a method of imparting pest resistance to plants comprising transforming the plants with a vector according to the present invention.

The method may also be effected by transforming isolated plant cells or tissues and generating plants from the transformed cells or tissue using standard culture techniques. Plants at any stage of development, parts thereof, plant cuttings, seeds, plant cells, and cell and tissue cultures transformed with vectors of the invention form further aspects of the invention.

Transformed plants can be used in conventional breeding programmes to transfer the DNA sequences of the invention.

The plants of the invention may be grown en masse. However, it is also feasible to use a smaller number of plants as "bait" plants within a crop area. Only the bait plants would include the insect control proteins. To ensure preferential targeting of bait plants by pests, attractants such as colour, hormone and scent lures may be used on or around the bait plants.

Alternatively, bait plants may be plants which a target pest has a preference for compared with the crop being grown. For example, it has been shown that rootworm have a preference for Taiuia over soybean and maize. Such bait plants may also be used in conjunction with attractants.

In another aspect, the present invention also provides a composition comprising a chimeric polypeptide of the invention and a carrier diluent, excipient or adjuvant therefor. In another composition aspect, there is provided a composition comprising plant material produced in accordance with the invention formulated with agriculturally acceptable excipients, carriers, diluents or adjuvants. The term "plant" as used herein encompasses plants, plant parts such as leaves, roots and flowers, plant cuttings, seeds, tissue cultures, cell cultures and plant cells but is not limited thereto.

Preferably, the composition is a pesticidal composition comprising a pesticidally effective amount of the polypeptide, or plant material and an acceptable carrier. These carriers include inert carriers such as surfactants, spreaders, stickers, mineral and organic granular carriers, stabilisers such as microencapsulation polymers or petroleum-based solvents.

Examples of surfactants, spreaders and stickers include C-Daxoil®, Codacide Oil®, D-C-Trate®, Supawet Oil®, Bond®, Boost® Penetrant, Citowett® and Freeway.

Examples of mineral granular spreaders include talcum powder, clay, silica, sand, limestone, gypsum, kaolin, montmorillonite, attapulgite and diatomite.

Examples of organic granular spreaders include corncob granules, pecan shells, peanut hulls and recycled paper fibre.

Examples of stabilisers include sodium tripolyphosphate, UV-absorbers (e.g. 2,4-dihydroxy benzophenone (Uvinul M-400, UM), 4 aminobenzoic acid (PBT), fluorescent brightener-28 (FB-28)), quenchers, radical scavengers, Hindered Amine Light Stabilizers (HALS), photostabilisers (e.g. clays, chromophores) and mineral oils.

Examples of microencapsulation polymers include cellulose acetate butyrate (CAB), ethyl cellulose (EC22 and EC 100), low and medium molecular weight poly(methyl methacrylate) (PMML and PMMM), poly(alpha-methylstyrene) (PMS) and starch urea formaldehyde (Starch-UF).

Examples of petroleum solvents include Aromatic 100, Aromatic 200, EXXSOL D 80, NORPAR 15, VARSOL 1, ISOPAR L, ISOPAR M, ISOPAR V and ORCHEX 796.

The pesticidal composition can be applied to plants in the form of sprays, dusts, or other formulations commonly employed in making pesticides. In the case of the plant material containing composition the material will be present in a dispersable or finely divided form to facilitate spraying onto plants to protect against pest attack. Such sprays would be useful in reducing pest numbers, whether the binding proteins, especially biotin-binding proteins, or degrading enzymes, had been released during processing via rupturing of the vacuoles, or not. If the vacuoles remain intact, then the proteins or enzymes will be released as the pests feed upon the preparation, and as such the invention may have utility as a mechanism for slow release of these proteins or enzymes, or any other proteins directed to the vacuole by the vector.

The compositions may further include one or more antifungal, antiviral, antimicrobial or pest control proteins all as discussed above. The use of these compositions in combination with the plants of the invention may be additive or synergistic, achieve broader spectrum control and reduce the risk of resistance developing.

Combinations particularly contemplated herein are compositions comprising proteinase inhibitors or insecticidal proteins such as *Bacillus thuringiensis* Cry proteins or biopesticides such as insect viruses or entomopathogenic fungi. Cry proteins including Cry1Ac, Cry1Cb, Cry1Da, Cry1F, Cry5 and Cry9A are preferred. The applicants have surprisingly found that plants transformed with biotin binding proteins and treated with Bt insecticidal protein exhibited synergistic toxic effects on pests (see Example 18). This suggests that plants containing chimeric genes expressing both biotin binding proteins and Bt proteins will be highly effective in protecting plants from pest attack. It is likely that such plants will be more toxic than those expressing either protein singly.

In another embodiment, the compositions of the invention can be used in conjunction with transgenic plants other than those of the invention. These other transgenic plants, for example, may incorporate genes conferring fungal, viral, microbial or herbicide resistance; genes conferring early ripening, heat stability, increased accumulation ability of desired products such as starch or cellulose or any other desirable trait as are known in the art. The composition of the invention when applied to the transgenic plant may also achieve the desirable results discussed above with plants of the invention.

In another embodiment, a composition of the invention may be applied to harvested material to prevent pest damage in storage. In an extrapolated application, the compositions may similarly be used in plant derived products such as flours, meals, cereals and the like to prevent or control pest infestation.

Also provided by the present invention is a method for controlling or killing pests comprising administering to said pest an amount of a chimeric polypeptide of the invention, which includes a sequence encoding a pest control protein, effective to control or kill said pest.

In one embodiment of the method, the chimeric polypeptide is administered with a second pest control protein, wherein the combination provides more effective control than administration of the second pest control protein alone. It will also be appreciated that more complex combinations of pest control proteins including a polypeptide of the invention are feasible. Most commonly, two to five additional pest control proteins will be used. However, the methods and compositions are not limited thereto. The additional pest control plants may comprise any of those already discussed. A preferred additional pest control protein is a Bt protein, especially a Cry protein.

In a related aspect, also provided is a method of controlling or killing pests, the method comprising administering to said pest plant material of the invention which includes a sequence encoding a pest control protein. Compositions of the invention may also be used in these pest control methods.

It will also be appreciated that a further method for controlling pest attacks on plants of the invention expressing a pest control protein, comprises treating those plants with a Bt protein or composition incorporating same.

As discussed above, the pests against which the invention is most effective are the immature stages of insects, including larvae, grubs, nymphs and instars. Administration may be achieved according to any suitable method known in the art. For example, through plant material, sprays, mulches, baits, dusts or other compositions which the pest to be controlled takes up through feeding, inhalation, transdermal absorption or other administrative route. Pests which may be killed or controlled using this method include those discussed above and particularly those referenced in the accompanying Examples and those pests belonging to the same insect orders as those referenced in the accompanying Examples.

It will be appreciated that the above description is provided by way of example only and that variations in both the materials and techniques used which are known to those persons skilled in the art are contemplated.

Non-limiting examples illustrating the invention will now be provided.

EXAMPLE 1

Experimental Details Concerning the Preparation of Constructs

Materials:
Custom primers were synthesized by Life Technologies. Subcloning Efficiency DH5 competent Cells were purchased from Life Technologies and the Hybaid Recovery Plasmid Mini Prep Kit from Hybaid Limited. All enzymes, unless otherwise stated were purchased from Promega Ampligase Thermostable DNA Ligase and Reaction Buffer and GELase were purchased from Epicentre Technologies and Polymerase Chain Reaction (PCR) reagents from Perkin Elmer.

The Avidin cDNA (pGEMav) carried on the plasmid pGEM13 was supplied by Professor M. S. Kulomaa ((Department of Biological and Environmental Science, University of Jyvaskyla, Finland) and the Potato Proteinase Inhibitor I (PPI-I) cDNA was isolated in this laboratory (Beuning et al. 1994, GenBank Accession #L06606) and cloned into pUC19.

The Streptavidin cDNA, carried on the plasmid pET3a was supplied by The DuPont Merck Pharmaceutical Company. The Potato Proteinase Inhibitor II (PPI-II) genomic sequence was isolated in this laboratory and cloned into pUC19 (Murray and Christeller, 1994).

Methods:
Subcloning Efficiency DH5 competent Cells were used for general cloning and amplification of recombinant plasmids and the Hybaid Recovery Plasmid Mini Prep Kit was used for plasmid preps. Isolation and recovery of DNA fragments was achieved by agarose gel electrophoresis followed by treatment of excised gel bands with GELase.

DNA Sequencing and Computer Analysis:
DNA sequencing was carried out on an Applied Biosystems (ABI) DNA Sequencer using dye terminator chemistry. Sequence analysis was performed using the Wisconsin Package Version 9.1, Genetics Computer Group (GCG), Madison, Wis.

EXAMPLE 2

Preparation of a Binary Vector Designed to Express a Chimeric Polypeptide Comprising Avidin Mature Peptide Fused to a Potato Proteinase Inhibitor I Signal Peptide Methods:
A one-step PCR-based mutagenesis method employing the combined use of a thermostable DNA polymerase and thermostable DNA ligase (Moore and Michael, 1995), was used to prepare a construct comprising the sequence encoding the mature Avidin polypeptide (Gope et al. 1987) fused to a PPI-I signal sequence. A Bgl II site was produced downstream of the PPI-I leader sequence at-positions 92–97 of the PPI-I coding sequence and a BamH I site was created upstream of the sequence encoding the mature Avidin polypeptide, at positions 65–70 of the sequence encoding the Avidin protein, as shown in FIG. 1 and FIG. 2 respectively. These two restriction sites have compatible cohesive ends.

Primers:
Forward M13 (lacZ) Primer [Perkin Elmer] (SEQ ID NO:12):
5'-GCCAGGGTTTTCCCAGTCACGA-3'
Reverse M13 (lacZ) Primer [Perkin Elmer] (SEQ ID NO:13):
5'-GAGCGGATAACAATTTCACACAGG-3'
Avidin Upstream Primer (SEQ ID NO:14):
5'-GCACACCCGGCTGTCCACCTG-3'
Phosphorylated Mutagenic Primers
PPI-I mutagenic primer (SEQ ID NO:15):
5'-PGATGGACCAGAGATCTTAGAAC-3'
Avidin mutagenic primer (SEQ ID NO:16):
5'-PGGCTCCCGGGATCCCTGCCAG-3'

Amplification/Mutagenesis Reactions:
To generate mutant products a total PCR reaction volume of 50 μL with an effective 1 X Ampligase Reaction Buffer [20 mM Tris-HCl (pH 8.3 at 25° C.), 25 mM KCl, 10 mM MgCl$_2$, 0.5 mM NAD and 0.01% Triton X-100] was used with the following conditions:

100 pmol each outer primer
1 mol phosphorylated mutagenic primer
40 nmol each dNTP
0.1 mmol dithiothreitol
5 U Taq DNA polymerase
5 U thermostable DNA ligase
1 ng recombinant plasmid DNA template Reactions were first incubated at 94° C. for 3 min., followed by 30 amplification cycles performed as follows:
94° C., 1 min.
40° C., 1 min.
65° C., 6 min.

Amplification cycles were followed by a final extension at 65° C. for 7 min.

Restriction analysis of amplification products from both mutagenesis reactions revealed mutant product to be present, but only at a maximum of 5% of the total product. To increase the yield of mutated product, Bgl II (for PPI-I mutagenesis) and BamH I (for Avidin mutagenesis) digestion products were ligated and then used as template for a second amplification reaction using outer primers only (Avidin Upstream and Reverse M13 (lacZ) for Avidin; Forward M13 (lacZ) and Reverse M13 (lacZ) for PPI-I). For PPI-L greater than 95% of second round amplification product had the desired Bgl II site and approximately of the second round product for Avidin mutagenesis possessed the BamH I site.

The mutated PPI-I amplification product was digested with Bgl II and Sal I and the mutated Avidin product with BamH I and Hind III. The PPI-I leader sequence and the coding sequence for the Avidin mature protein were isolated and recovered for cloning along with Xho I/Hind III digested non-recombinant pART7 vector (Gleave, 1992). These three species were ligated, resulting in recombinant pART 7 [refer FIG. 5] and the sequence of the chimeric gene was checked. Subsequently, the expression cartridge containing the gene fusion was cloned into the Not I site of pART7 vector (Gleave, 1992) and this construct [refer FIG. 7A] was mobilized to *Agrobacterium tumefaciens* (strain LBA4404) by standard tri-parental mating techniques (Ditta et al. 1980).

Discussion:

The resulting PPI-I/Avidin fusion protein has a total of 161 amino acids as shown in FIG. 8. The first 31 amino acids are PPI-I sequence and since the leader sequence comprises the first 23 amino acids, the original patterning of amino acids around with the site for cleavage between the signal sequence and the mature protein is retained. There are two single base pair changes in the gene fusion sequence relative to the predicted sequence. These changes are presumably the result of PCR error. One change is silent and the other results in an amino acid change from Serine to Proline at position 17 of the PPI-I signal sequence.

EXAMPLE 3

Preparation of a Binary Vector Designed to Express a Chimeric Polypeptide Comprising Synthetic "Core" Streptavidin Peptide Fused to a Potato Proteinase Inhibitor II Signal Peptide Methods:

A fused gene was prepared comprising the sequence encoding Synthetic "Core" Streptavidin (Thompson and Weber 1993) fused to a PPI-II signal sequence. The Streptavidin cDNA, carried on the plasmid pET3a was cloned into the EcoR I/Xba I sites of pUC19 (FIG. 3). The PPI-II signal sequence (FIG. 4) which contains an intron was isolated from recombinant plasmid using PCR with a sense primer binding to pUC19 and an antisense primer incorporating an EcoR I site into a 5' overhang. The primers were as follows.

sense primer (SEQ ID NO:17):
5'-CTG CAG GTC GAC TCT AGA GGA-3'
antisense primer (SEQ ID NO:18):
5'-GGT GAA TTC TTA GTA CAG ATC TTC GCA-3'

Amplification Reaction:

A total PCR reaction volume of 50 μl with an effective 1 X PCR Buffer [10 mM Tris-HCl, pH 8.3 and 50 mM KCL] was used with the following conditions:

20 pmol each primer
15 nmol each dNTP
2.0 mM MgCl$_2$
5 U Taq DNA polymerase
1 ng recombinant plasmid DNA template Reactions were first incubated at 94° C. for 2 min., followed by 30 amplification cycles performed as follows:

94° C., 1 min.
50° C., 1 min.
72° C., 1 min.

Amplification cycles were followed by a final extension at 72° C. for 7 min.

Figure 6:
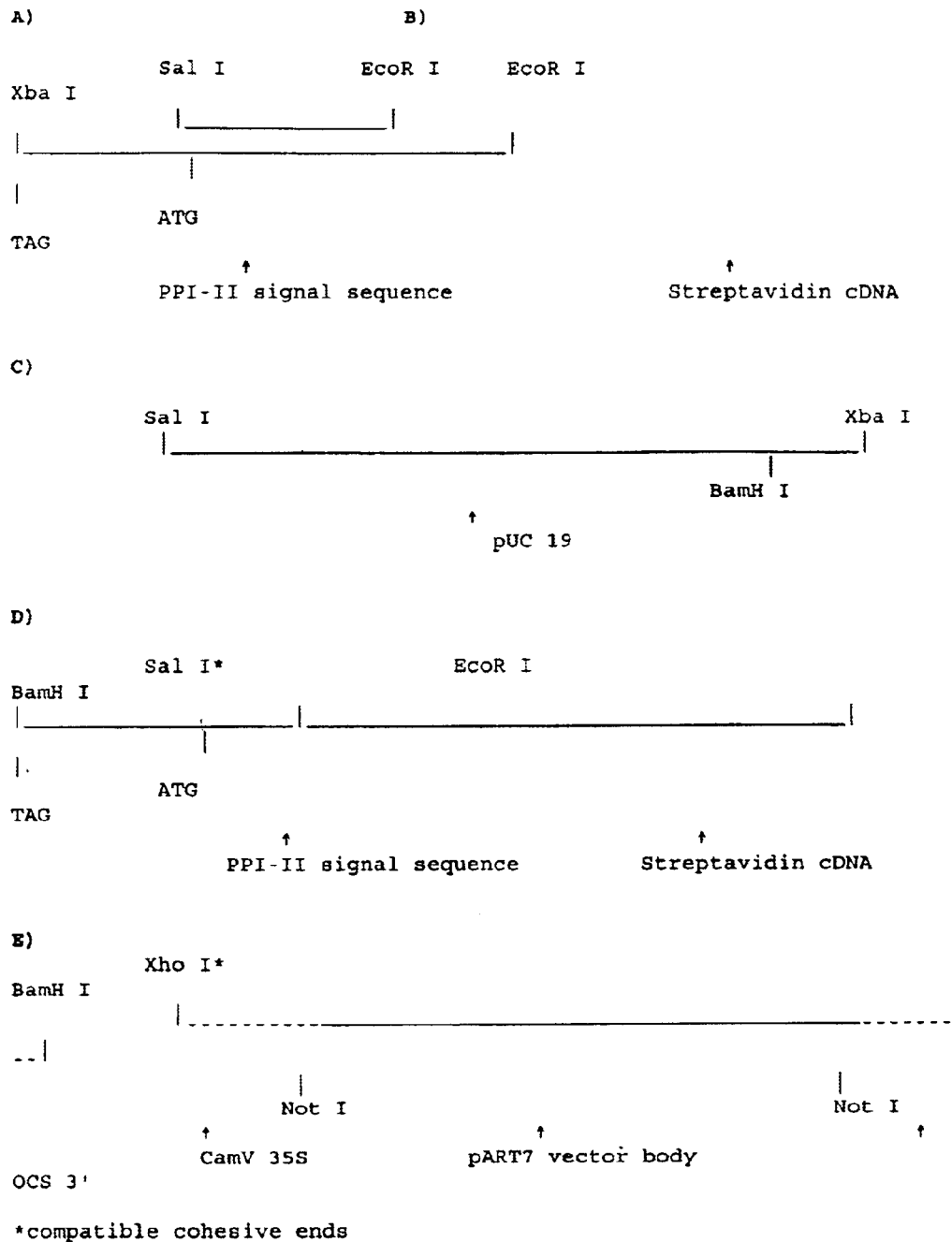

The PCR product representing the PPI-II signal sequence was digested with Sal I and EcoR I. The recombinant plasmid pUC 19/Streptavidin cDNA was digested with EcoR I and Xba I and the Streptavidin cDNA was isolated from the vector and recovered. Non-recombinant pUC19 was digested with Sal I and Xba I and the three species were ligated to produce a construct comprising the gene fusion cloned into the Sal I and Xba I sites of pUC19. The sequence of the gene fusion was checked and subsequently cloned into the Xho I and BamH I sites of the pART7 vector [refer FIG. 6]. The pART7 expression cartridge containing the gene fusion was then cloned into the Not I site of pART27 and this construct [refer FIG. 7B] was mobilized to *Agrobacterium tumefaciens* (strain LBA4404) by standard tri-parental mating techniques.

Discussion:

The resulting PPI-II/Streptavidin fusion protein has a total of 168 amino acids as shown in FIG. 9. The first 36 amino acids are PPI-II sequence. Five of these amino acids follow the cleavage site, preserving the amino acid pattern around this position. The nucleotide sequence of the PPI-II signal sequence includes a 119 bp intron (Murray and Christeller, 1994).

EXAMPLE 4

Immunodetection of Avidin in Transgenic Tobacco

Methods:

1. Tissue Print

Samples were taken from the top 8 leaves of a tobacco plant expressing avidin (PLA2/9 #1). Four plants not expressing avidin were used as controls (PLA 2/3, NT12, GUS1 and JB3-13.

Pieces of transgenic tobacco leaves 1×1 cm were frozen at −20° C. for 20 min, allowed to thaw and printed on to nitrocellulose using mechanical pressure.

Labelling Protocol:

Printed nitrocellulose membranes was washed in PBS-T (phosphate buffered saline with 0.1% Tween 20) for 20 min, blocked in 0.1% BSA-C (Aurion) for 15 min and incubated in 1:1000 anti-avidin (Sigma A-5170) diluted in blocking buffer for 1 h (as a control for non-specific binding, this last step was deleted in duplicate sets of prints). The membrane was then washed in PBS-T, incubated in goat anti-rabbit IgG-gold (10 nm) (Sigma), washed again in PBS-T, then in double distilled water and drained. Finally the membrane was silver enhanced (BioCell silver enhancement kit) for 15 min. Enhancement was stopped by washing in distilled water.

Results:

The nitrocellulose membrane silver enhanced (turned brown) over most of the tissue print area in the smallest top leaf. In all other leaves the silver enhancement was detected mainly towards the cut edges of leaf material. There was no silver enhancement on the prints from control plants or on the prints made in the absence of the anti-avidin antibody. This labelling protocol also acts as a test of the labelling procedure.

2. Embedded material

Pieces 1×1×5 mm of transgenic tobacco leaf(Pla 2/9 #1)were filed in 2% paraformaldehyde and 2.5% glutaraldehyde in 0.1M phosphate buffer under vacuum for 1 h. The material was post-fixed in 1% osmium tetroxide 1 h, dehydrated in an ethanol series and embedded in Spurrs resin. Pieces of non-transgenic tobacco (control material) were prepared in a similar manner. Sections were cut 300 nm thick for light microscopy (LM) and mounted on Poly-L-lysine coated slides. Sections for electron microscopy (EM) were cut 130 nm thick (gold) and mounted on carbon/formvar coated nickel grids.

Labelling Protocol:

For light microscopy the sections had a Pap pen ring drawn around them to contain the incubation liquid. The protocol for LM and EM were the same thereafter. The sections were etched for 30 min in 10% hydrogen peroxide to remove the osmium, blocked in 0.1% BSA-c for 15 ml, incubated in anti-avidin 1:500 in PBS-T for 1 h (deleted for control) and washed in PBS-T. They were then incubated in goat anti-rabbit IgG-Alexa 488 (Molecular Probes) for 1 h. The sections were then washed thoroughly in buffer and then in double distilled water.

The methodology for labelling of sections for the electron microscope (EM) was similar to that for the light microscope (LM) except goat anti-rabbit IgG-gold (10 nm) was used instead of goat anti-rabbit IgG Alexa 488.

Sections were then viewed on a fluorescence microscope. Sections (1 μm thick) were stained methylene blue/AzureII.

Figure 13:
Figure 14:
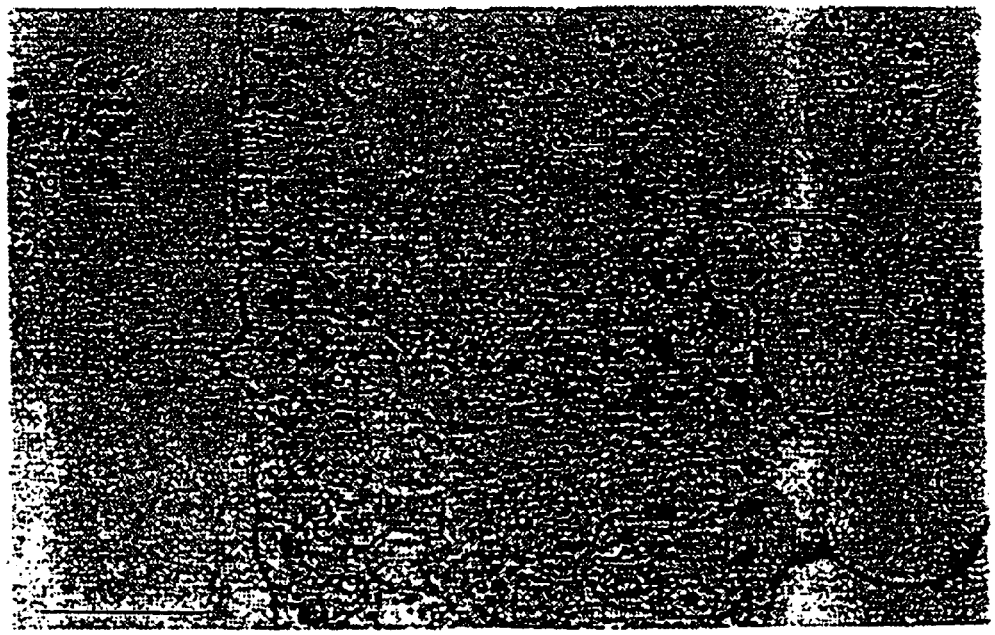

Results:

Sections of Pla 2/9 #1 smallest top leaf stained for light microscopy shows darkly staining bodies mesophyll, epidermal cells, and cells of the glandular hairs (FIGS. 13 and 14)

Figure 15:
Figure 16:

Immunolabelling of LM (FIG. 14) and EM (FIGS. 15 and 16) sections showed labelling of protein-type bodies in the vacuoles of mesophyll cells (both spongy and pallisade) and in glandular hairs (FIGS. 15 and 16). The protein bodies were usually condensed into one body which was sometimes seen as a ring. There was no labelling in the vascular tissue or in the trichomes. Control material did not label.

Conclusions:

The results indicate that avidin is synthesized in most common cell types in tobacco leaves. The bulk of the protein appears to be transported to the vacuole and deposited as a protein body within this organelle.

EXAMPLE 5

ELISA Assay of Avidin and Streptavidin

The following general ELISA assay technique was used for assaying for avidin and streptavidin where indicated in the following examples.

Method:
1. Plant material was ground with 2 volumes (w/v) of ice cold 0.05 μM sodium phosphate (pH 7.5) containing 5% polyvinylpolypyrrolidone. This was centrifuged and the supernatant used for analysis. In order to construct standard curves control plant material was ground in the above buffer with and without 0.2 mg/mL avidin or streptavidin and centrifuged.
2. Generally 10 μL of extract and 90 μL of coating buffer (15 mM sodium carbonate, 46 mM sodium bicarbonate, pH 9.6) were mixed in a 96 well microtitre plate and incubated at 4C overnight. Each sample was duplicated and standards consisted of various proportion of control plant extract/added protein extract to the same total extract volume as the samples.
3. Plates were washed (3×) in phosphate-buffered saline (PBS) containing 0.02% Tween 20 (PBST) and incubated for 1 hr in 100 μL of PBST containing 0.5% gelatin.
4. Plates were washed (3×) in PBST and incubated for 1 hr in 100 μL of PBS containing either polyclonal rabbit anti-avidin or anti-streptavidin antibodies.
5. Plates were washed (3×) in PBST and incubated for 1 hr in 100 μL of PBS containing goat anti-rabbit antibody linked to alkaline phosphatase.
6. Plates were washed (3×) in PBST and, after addition of 100 μL of 0.1 M diethanolamine (pH 9.8) containing 0.5 mM $MgCl_2$ and 0.5 mg/mL p-nitrophenyl phosphate, assayed at 410 nm in a microtitre plate reader. Initial rates of samples were determined by linear regression over 5–10 mins and compared to rates obtained for the duplicate standard curves (8 avidin or streptavidin concentrations) on each microtitre plate.
7. Concentrations of avidin and streptavidin in the samples were determined as the mean molar concentration in the tissue assuming that the specific gravity of plant tissue is one and molecular weights for avidin and streptavidin of 15600 and 16473 (for the standard) respectively.

EXAMPLE 6

Toxicity of Whole Tobacco (*Nicotiana Tabacum*) Plants Expressing Avidin to Potato Tuber Moth Larvae (*Phthorimaea operculella*) (*Lepidoptera*: Gelechiidae)

Constructs:

Non-transformed control plants
  2 plants (NT 1, NT 2)
Control plants transformed with pumpkin fruit chymotrypsin inhibitor (PFCI) but not expressing the protein
  3 plants (JB3/1, JB3/2, JB5/1)
Tobacco plants transformed with the avidin gene with a PPI-I targeting sequence (Example 2 above)
  6 lines (PLA2/2, PLA2/7, PLA2/9, PLA2/13, PLA2/20, PLA2/24), 4 clonal plants per line Trial Design:

Trial 1:

The tobacco plants were removed from tissue culture and potted in fertilised potting mix (Smiths® general potting mix) before being placed in large ventilated acetate containers (220×300 mm) in a containment glasshouse unit at 22±5° C. They were watered daily to maintain high humidity and soil moisture content.

Eight days later, when plants were well established with at least four to five small leaves, ten neonate potato tuber moth (PTM) larvae were placed on each tobacco plant, usually two per leaf. Prior to inoculation the larvae were weighed in batches of five (since single larvae are too small to give an accurate reading). TM larvae were obtained from a laboratory culture reared on potato tubers following the same basic procedure as Broodryk (1971) and Meisner et al. (1974).

Trial 2:

One week after Trial 1 was completed, the tobacco plants were cut back to the second node and allowed to regenerate leaves. When the plants had developed four to five leaves (in approximately 11 days) they were each inoculated again with ten neonate PTM larvae, usually two per/leaf, weighed in batches of five prior to inoculation as above.

Trails 1 and 2:

Inoculated plants were kept individually in acetate containers in the containment glasshouse unit at 22±5° C. for nine days. Under these conditions growth of control larvae is exponential from hatch to nine days, but after this growth rate slows as pupation approaches. Hence in order to compare growth rates of larvae on control and transgenic plants, the trial was concluded after nine days. Damaged leaves containing larvae were removed, and larvae were dissected out of their mines within the leaf or stem tissue. The intention was to weigh the larvae at this point in order to estimate growth rates, but, except for those on control plants, larvae were mostly dead, dried and shrivelled. Consequently head capsules were measured so that the instar reached at death could be recorded.

Level of Expression of the Avidin Protein

Results:

The level of expression of avidin in each of the plant lines was quantitated using chemilumenessance detection of avidin protein from western blots of leaf tissue, compared to authentic avidin standards and expressed as percentage of total leaf protein. These levels are given in Table 1 below.

TABLE 1

The level of expression of avidin as % of total leaf protein, determined using the chemiluminescence method

| Plant Line | Avidin expression % total leaf protein ($\mu$M)* |
|---|---|
| PLA2/2 | 0.07 (0.90) |
| PLA2/7 | 0.10 (1.23) |
| PLA2/9 | 0.07 (0.90) |
| PLA2/13 | 0.06 (0.77) |
| PLA2/20 | 0.065 (0.83) |
| PLA2/24 | 0.06 (0.77) |

*The chemiluminescence method was used to estimate avidin expression as % total soluble leaf protein. In later Examples, an ELISA method (Example 5) was used to estimate the expression levels as $\mu$M. Hence these values were converted to $\mu$M. Avidin expression was measured in clones of these original plants using the ELISA method and results given in Example 8, Table 5. These levels are about three times higher than those given in Table 1. This may reflect the fact that, in these trials the measurements were done on plants still in tissue culture whereas those in Example 8 wree done on large leaves from mature plants.

Mortality of PTM Larvae Feeding on Whole Tobacco Plants Expressing the Avidin Gene.

Figure 10:
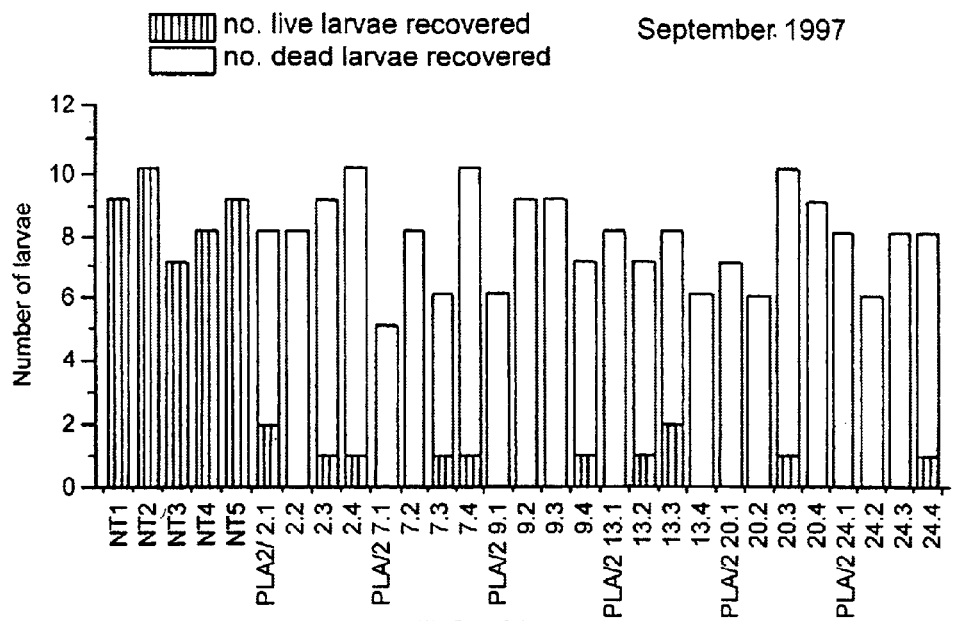

Trial 1:

Good recovery rates of larvae from both control and transgenic plants were obtained: 86% from controls and 76.7% from transformed plants. FIG. 10 clearly shows the high mortality PTM larvae after feeding for nine days on whole transgenic tobacco plants expressing the avidin gene compared to both non-transformed control plants and control plants transformed with, but not expressing, the pumpkin fruit chymotrypsin inhibitor (PFCI) gene.

The majority of dead larvae were recovered from mines where they had died at the "cutting face". A few (5% of dead larvae) were recovered from the surface of leaves, having generally left a mine close by. It is most likely that the majority of larvae not recovered had died in this way and had fallen off the leaves. Some mines were found without occupants. However, there was no evidence that larvae had started and abandoned mines on several occasions as we have previously observed in another experiment in which larvae were fed on tobacco expressing cry 1Ac and cry 9Aa2 genes (Gleave et al. 1998).

PTM larvae undergo four instars during their development. In order to define the stage of development of the larvae at death, head capsule widths were measured using a micrometer eye-piece. All control larvae were alive and most were third instars. None of the larvae recovered on any of the plants expressing avidin had reached third instar before death and many had died during or just after the moult from first to second instar, as evidenced by the fact that the ecdysed cuticle was still attached. This reflects results in earlier trials with avidin incorporated into diet.

Table 2 below gives a breakdown of instars on each plant line.

TABLE 2

Number of larvae at each instar recovered from transgenic tobacco plants expressing avidin in Trial 1

| Plant line | Neonates inoculated | Number of larvae at | | | |
|---|---|---|---|---|---|
| | | 1st instar | 2nd instar | 3rd instar | 4th instar |
| NT control | 20 | 0 | 1 | 18 | 0 |
| JB control | 30 | 0 | 0 | 23 | 1 |
| PLA2/2 | 40 | 3 | 28 | 0 | 0 |
| PLA2/7 | 40 | 4 | 23 | 0 | 0 |
| PLA2/9 | 40 | 2 | 27 | 0 | 0 |
| PLA2/13 | 40 | 1 | 25 | 0 | 0 |
| PLA2/20 | 40 | 2 | 27 | 0 | 0 |
| PLA2/24 | 40 | 4 | 25 | 0 | 0 |

Figure 11:
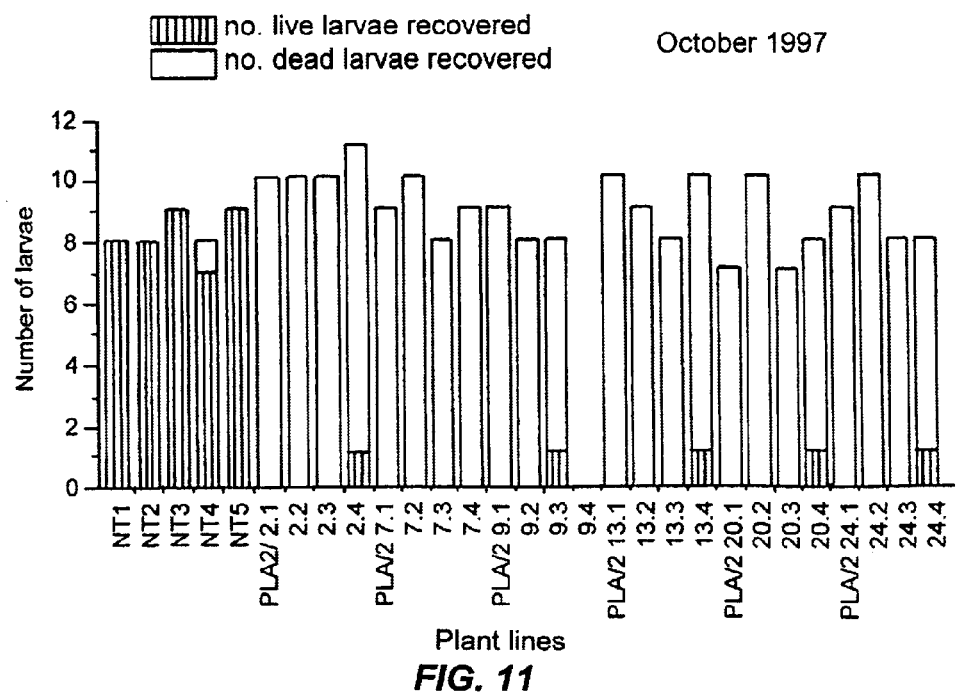

Trial 2:

Again there were good recovery rates of larvae from both control and transgenic plants: 88% from controls and 88.8% from transformed plants. FIG. 11 reflects the results of the first trial showing high mortality of PTM larvae fed on whole trans genic tobacco plants expressing the avidin gene compared to those on control plants. In fact a total of only four live larvae were recovered from all avidin expressing plants (<1.7% survival), whereas only three larvae had died on the control plants (94% survival).

Head capsule widths of larvae were measured and the number of recovered larvae at each instar is given in Table 3. As in the first trial, none of the larvae recovered from any of the plants expressing avidin had reached third instar before death and many had died during or just after the moult from first to second instar again the ecdysed cuticle was still attached in many cases.

TABLE 3

Number of larvae at each instar recovered from transgenic tobacco plants expressing avidin in Trial 2

| Plant line | Neonates inoculated | Number of larvae at | | | |
|---|---|---|---|---|---|
| | | 1st instar | 2nd instar | 3rd instar | 4th instar |
| NT control | 20 | 0 | 3 | 12 | 0 |
| JB control | 30 | 0 | 1 | 24 | 3 |
| PLA2/2 | 40 | 34 | 5 | 0 | 0 |
| PLA2/7 | 40 | 25 | 9 | 0 | 0 |
| PLA2/9 | 40 | 30 | 3 | 0 | 0 |
| PLA2/13 | 40 | 26 | 11 | 0 | 0 |
| PLA2/20 | 40 | 25 | 5 | 0 | 0 |
| PLA2/24 | 40 | 30 | 3 | 0 | 0 |

Conclusion:

Total mortality of PTM larvae fed on tobacco plants expressing the avidin gene would have occurred if the trials had been continued beyond nine days; larvae that survived for nine days were small, shrivelled and close to death as evidenced by their minimal response when touched by a fine sable paint brush.

Avidin expressed in tobacco plants is highly toxic to PTM larvae and has definite potential in the development of pest resistant crop cultivars.

EXAMPLE 7

Toxicity of Whole Tobacco (*Nicotiana tabacum*) Plants Expressing Streptavidin to Potato Tuber Moth Larvae (*Phthorimaea operculella*) (*Lepidoptera*: Gelechiidae)

Constructs:

Non-transformed Control Plants 6 plants (NT21–26)

Plants transformed with and expressing the streptavidin gene with a PPI-II targeting sequence (Example 3 above)-(Sav)

6 plant lines, 5 clones per line (5, 9, 10, 14, 23, 26)

2 plant lines, 3 clones per line (25, 28).

Trial Design:

Trial 1:

The transformed tobacco plants were removed from tissue culture, planted in fertilised potting mix (Smiths® general potting mix) and placed individually in large ventilated acetate containers (220×300 nm) in a containment glasshouse unit at 24±7° C. They were watered regularly to maintain high humidity and soil moisture content until well established.

Eleven days later, five neonate potato tuber moth (PTM) larvae were placed on each tobacco plant. Prior to inoculation the larvae were weighed in batches of five (since single larvae are too small to give an accurate reading on a 5-place balance). PTM larvae were obtained from a laboratory culture reared on potato tubers following the same basic procedure as Broodryk (1971) and Meisner et al. (1974).

Trial 2:

On completion of Trial 1, the tobacco plants were cut back to the second node and allowed to regenerate new leaves. When the plants had developed at least four to five leaves they were each inoculated again with five neonate PTM larvae as above. Unfortunately some individual plants died during this process and so fewer clones were tested for some lines in the second trial.

Trials 1 and 2:

Inoculated plants were kept individually in acetate containers in the containment glasshouse unit at 24±7° C. for nine days. Under these conditions growth of control larvae is exponential from hatch to nine days, but after this growth rate slows as pupation approaches. Hence in order to compare growth rates of larvae on control and transgenic plants, the trial was concluded after nine days. Damaged leaves containing larvae were removed, and larvae were dissected out of their mines within the leaf or stem tissue. The intention was to weigh the larvae at this point in order to estimate growth rates, but, except for those on control plants, the larvae were mostly dead, dried and shrivelled. Consequently head capsule width was measured for all larvae retrieved so that the instar reached at death could be recorded.

Results:

Level of Expression of the Streptavidin Protein:

The level of expression of streptavidin in each of the plant lines was measured using the technique described in Example 5. These levels are given in Table 4 below.

TABLE 4

Expression of streptavidin in tobacco plants

| Plant Line (Savα) | Expression of Streptavidin μM (s.e.) |
| --- | --- |
| 5 | 12.802 (0.834) |
| 9 | 17.818 (0.059) |
| 10 | 11.404 (0.896) |
| 14 | 18.178 (0.560) |
| 23 | 24.524 (0.042) |
| 25 | 21.703 (0.842) |
| 26 | 16.306 (1.831) |
| 28 | 15.788 (0.260) |

Figure 17:
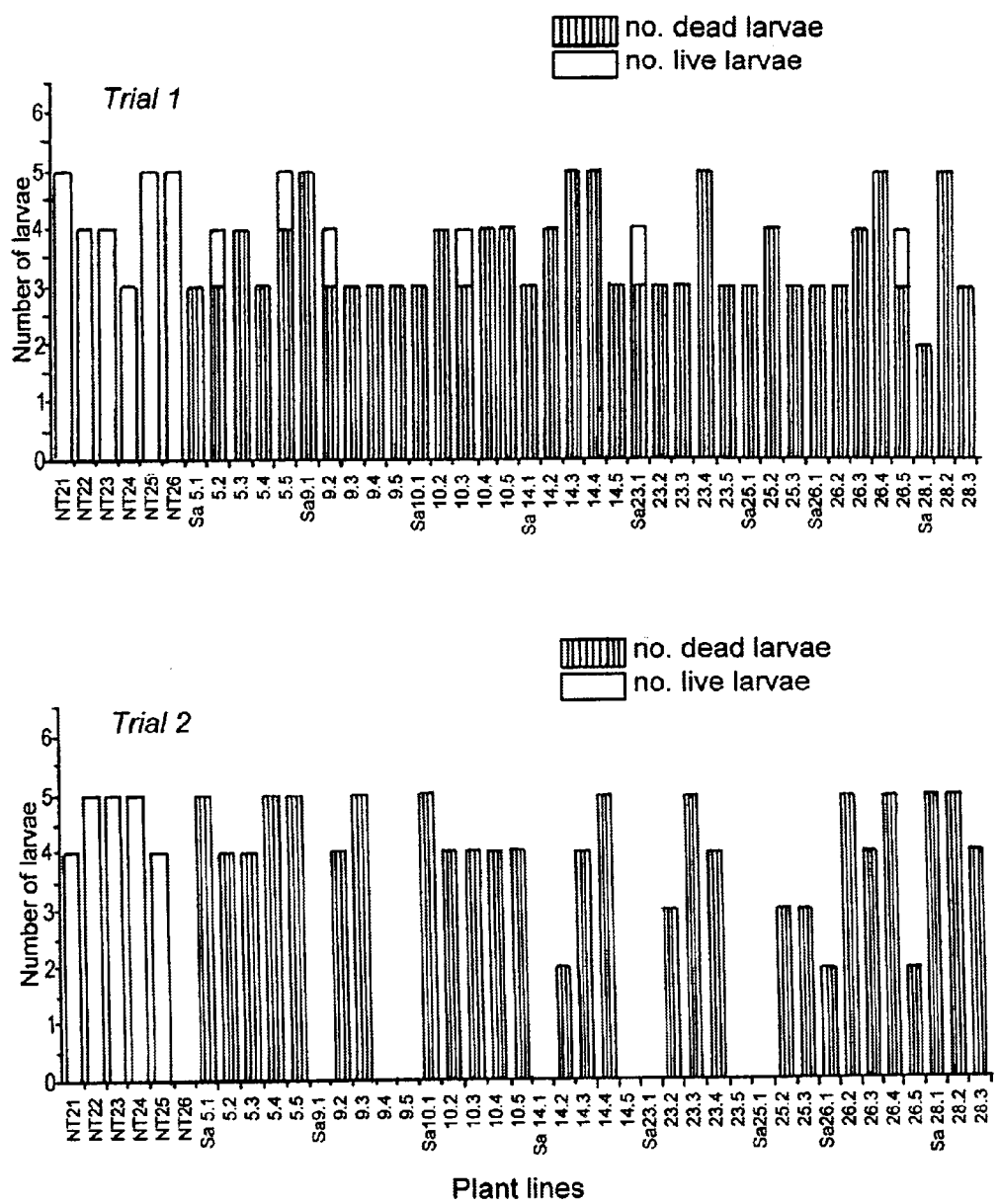
FIG. 17 shows the survival of larvae of the potato tuber moth, *Phthorimaea operculella* fed tobacco plants expressing streptavidin in two replicate trials.

Mortality of PTM Larvae Feeding on Whole Tobacco Plants Expressing the Streptavidin Gene:

Trials 1 and 2:

Recovery of larvae was good from control plants in both trials (88.6 and 92% respectively) and from transgenic plants (78.3 and 83% respectively) and similar to that reported in the trials with tobacco expressing the avidin gene (Example 6). FIG. 17 shows the number of live and dead larvae recovered nine days after inoculation, from each plant line in both trials. In Trial 2 there was total mortality on all plant lines, but in Trial 1 there were a few survivors after nine days on some plant lines: of the 25 larvae initially placed on the plants, two survived on line 5 and one each on lines 9, 10, 23 and 28. However, all of these "survivors" were close to death. In contrast, there was no larval mortality on control plants in either trial. As in Example 6, the majority of larvae had died within the mines in the leaves and only a few dead larvae were found on the leaf surface after abandoning their mines.

Figure 18:
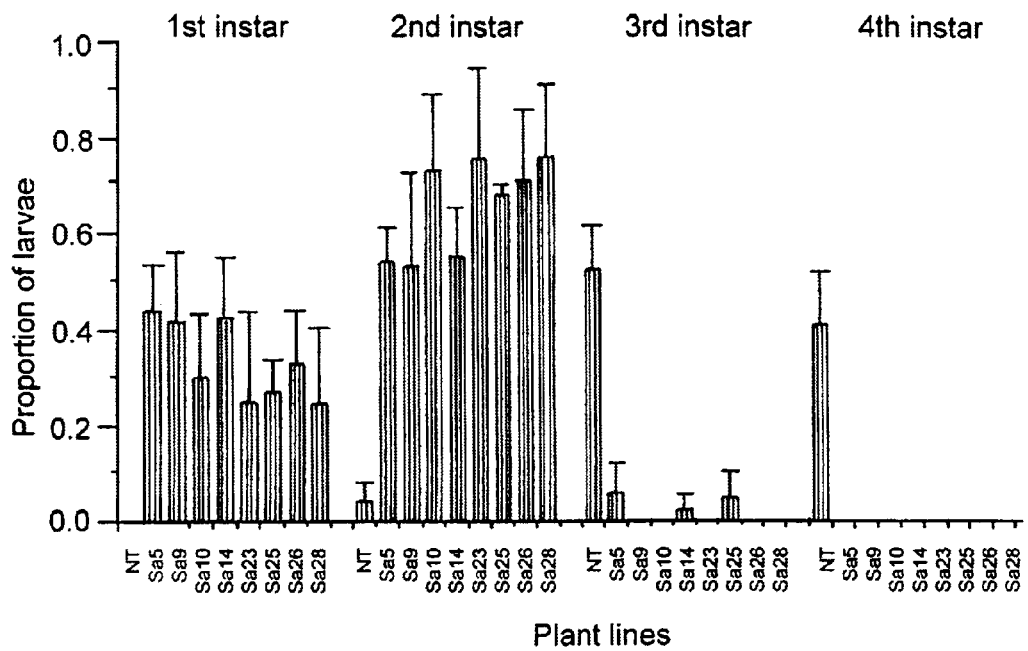
FIG. 18 shows the proportion of larvae of the potato tuber moth, *Phthorimaea operculella* at each instar after feeding for nine days tobacco plants expressing streptavidin.

Head capsule widths of all larvae were measured after they were removed from their leaf mines to determine their stage of development. Larvae recovered from non-transgenic (NT) plants were all alive in both trials and all but two had reached 3rd or $4^{th}$ instar. In contrast, the majority of larvae feeding on the transgenic plants had died at $1^{st}$ or $2^{nd}$ instar (FIG. 18). Most of these had died just prior to or during the ecdysis from $1^{st}$ to $2^{nd}$ instar as was evidenced by the number of dead larvae with ecdysed skins and head capsules still attached.

Conclusion

Tobacco plants expressing the streptavidin gene were highly insecticidal to potato tuber moth larvae. Larval mortality occurred on all plants tested expressing the gene and the majority of larvae died just prior to, during, or immediately after ecdysis between the $1^{st}$ and $2^{nd}$ instar.

EXAMPLE 8

Toxicity of Avidin Expressed in Tobacco (*Nicotiana tabacum*) Leaves to Larvae of the Common Cutworm *Spodoptera litura* (*Lepidoptera*: Nictuidae) and the Cotton Bollworm (Tomato Fruitworm, Cornear Worm) *Helicoverpa armigera* (*Lepidoptera*: Noctuidae)

Constructs:

Control lines:

Non-transformed control plants:

4 plants (NT11, NT12, NT13, NT14)

Control plants transformed with PRD400 vector with pumpkin fruit chymotrypsin inhibitor (PFCI) gene but which do not express the transgene:

8 plants (6 independent transformants) (JB3-1C/AB. JB3-1, JB3-13, JB3-15, 2 clonal JB3-16 plants, and 2 clonal JB3-25 plants)

Control Plants Transformed with the pART27 Vector:
  7 plants (all independent transformants) (art27c #1, art27c #3, art27c #4, art27c #5, art27c #6, art27c #7, art27c #8)
Control Plants Containing the pART27 Vector with the GUS Gene (uid):
  4 plants (all independent transformants) (GUS 1, GUS2, GUS5, GUS8)
Avidin-expressing Lines:
  Tobacco plants transformed with the avidin gene with a PPI-I targeting sequence (Example 2 above):
  6 plant lines derived from 6 separate transformation events (PLA2/2, PLA2/7 PLA2/9, PLA2/13, PLA2/20, PLA2/24), 4 clonal plants per line.
Insects:
  Spodoptera litura were obtained from a laboratory colony originally established from moths field-collected in Queensland, Australia, while Helicoverpa armigera were from a laboratory colony established from moths collected in Christchurch, New Zealand. Both colonies were reared on artificial diet as described in McManus and Burgess (1995).
  Neonate S. litura larvae were placed on tobacco leaves within 12 h of emergence from eggs. Initial larval weight was estimated from the mean weight of three samples of 100 larvae.
  Neonate H. armigera larvae were placed on artificial diet for 48 h following emergence from eggs, and then placed on tobacco leaves as late first instar larvae. Initial larval weight was determined as the mean of the individual weights of a randomly chosen sample of 48 larvae weighed at the beginning of the experiment.
Trial Design:
  On each plant used in the experiment, Leaf 1 was designated as the uppermost (youngest) leaf which was 15 cm or more in length from leaf tip to leaf base (the point at which the leaf joined the petiole). The leaves below Leaf 1 were assigned numbers consecutively down the plant Leaves 1 and 2 were used for H. armigera as previous experiments had shown that larvae grow best on these leaves. For similar reasons. S. litura were given Leaves 4 and 5 of the same plants.
  To ensure leaves remained turgid during larval feeding each leaf was cut from the plant close to the stem leaving a long petiole, and each petiole was immediately plunged into about 20 $\mu$L of a setting solution of 0.4% agar in a 30 mL coulter cup.
  At the start of the experiment, larvae were placed on leaves from one plant from each of the six clonal avidin-expressing lines, and on six control plants. Twelve H. armigera larvae were placed on the undersides of Leaves 1 and 2, i.e 12 larvae×2 leaves×6 plant lines=144 larvae, and an equivalent number of control larvae were used. For S. litura; 15 larvae were placed on the upper surfaces of Leaves 4 and 5, i.e. 15 larvae×2 leaves×6 plant lines=180 larvae on both avidin and control treatments.
  Each leaf with larvae was placed in a 300×210×80 mm plastic storage box lined with paper towels and with a snap-on lid. Larvae and leaves were checked daily, and leaves were replaced with new ones from fresh plants as necessary so that larvae could feed ad libitum. Throughout the experiment, larvae on avidin plants were fed leaves from within the same clonal line (e.g. PLA2/2 or PLA2/7), and larvae on control plants were kept on the same genetic plant type (NT or JB-3 or art27c or GUS). When necessary, leaves of the equivalent physiological age from previously used plants were utilised.
  The experiment was conducted in a controlled temperature room at 24.5±1° C. and 60% relative humidity, with a 16:8 h light:dark cycle.
  Larvae were first weighed and survivors counted at Day 8, and then at regular intervals throughout the experiment until death or until pupation had begun in a treatment.
Determination of Avidin Expression Levels:
  To measure expression levels in plants fed to larvae, two leaf samples of 8 cm$^2$ were taken from Leaf 4 of all avidin plants used in the trial. One sample was taken just before larvae were initially placed on the leaf, and the other a few days later, following the transfer of larvae from the leaf onto a fresh leaf. Expression was measured as described in Example 5.

TABLE 5

Expression levels of avidin in plants

| Plant line | Mean expression level of avidin ($\mu$M) | Standard error | Number of samples |
| --- | --- | --- | --- |
| PLA2/2 | 3.10 | 0.42 | 8 |
| PLA2/7 | 3.29 | 0.23 | 8 |
| PLA2/9 | 4.37 | 0.51 | 8 |
| PLA2/13 | 3.40 | 0.38 | 8 |
| PLA2/20 | 4.59 | 0.31 | 8 |
| PLA2/24 | 4.10 | 0.21 | 8 |
| NT | 0 | — | 8 |

Figure 19:
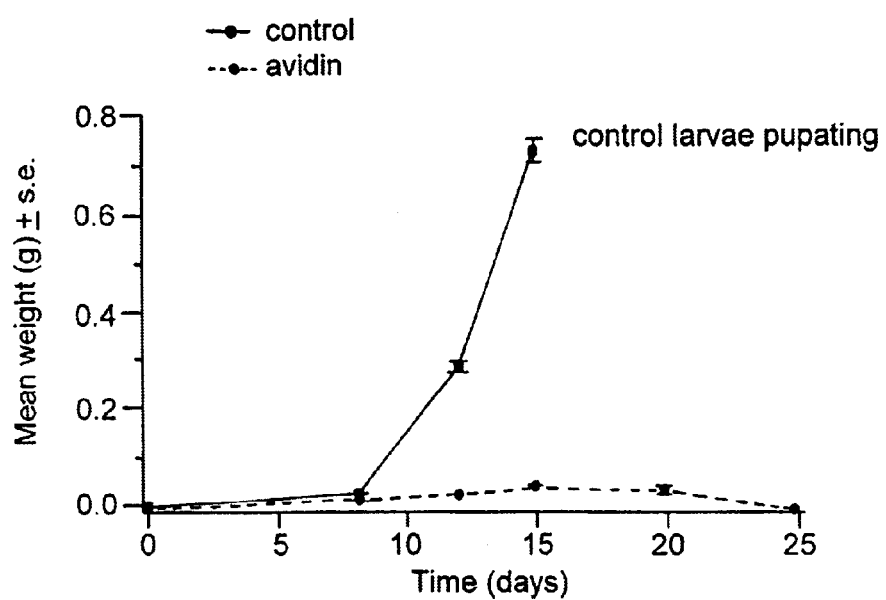
FIG. 19 shows the growth of larvae of the common cutworm, *Spodoptera litura*, fed tobacco leaves expressing avidin.
Figure 20:
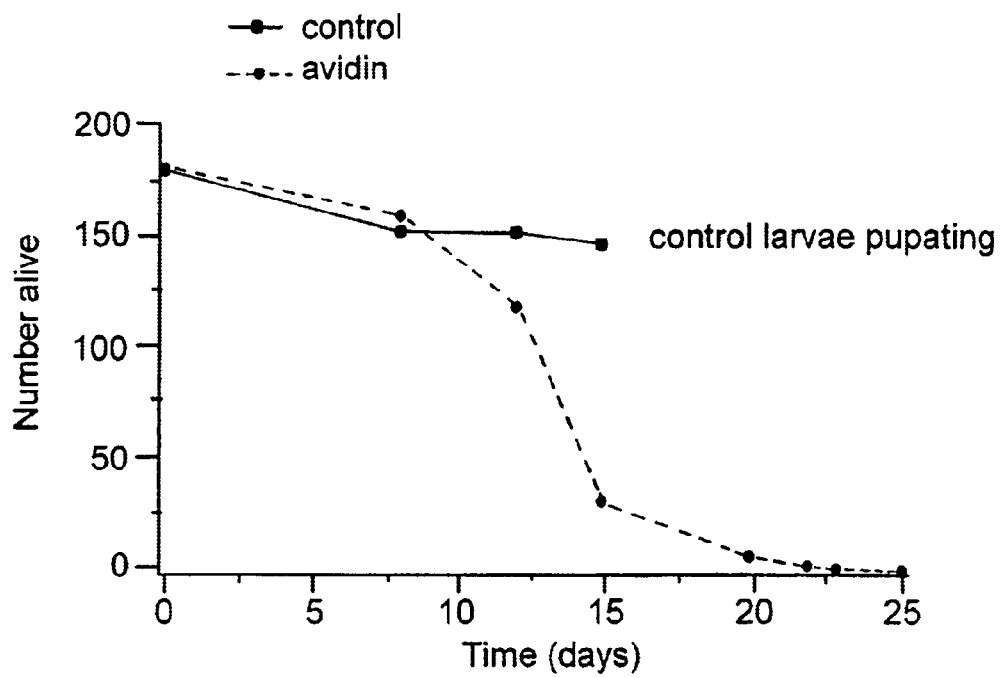
FIG. 20 shows the survival of larvae of the common cutworm, *Spodoptera litura*, fed tobacco leaves expressing avidin.
Figure 21:
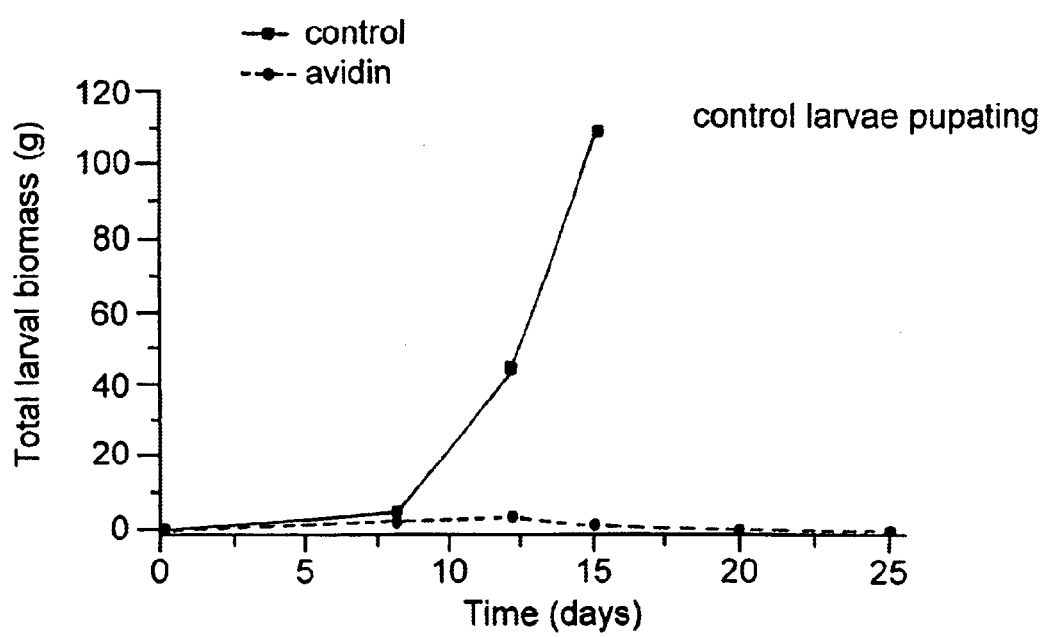
FIG. 21 shows the accumulation of larval biomass of the common cutworm *Spodoptera litura*, fed tobacco leaves expressing avidin.
Figure 22:
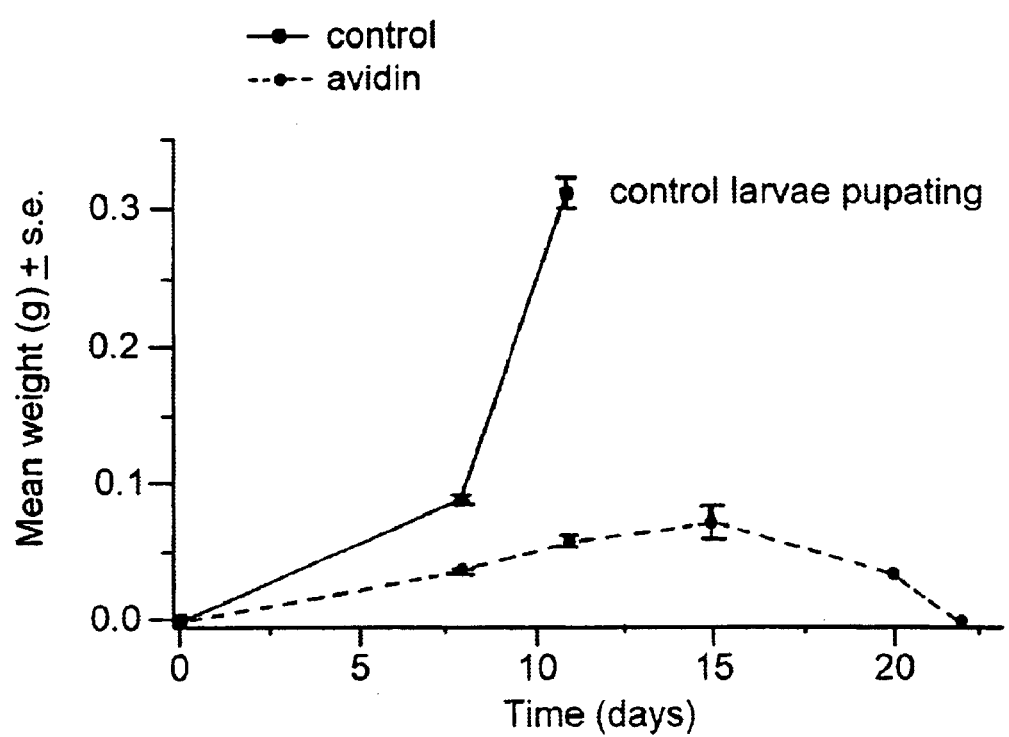
FIG. 22 shows the growth of larvae of the cotton bollworm (corn earworm, tomato fruitworm), *Helicoverpa armigera* fed tobacco leaves expressing avidin.
Figure 23:
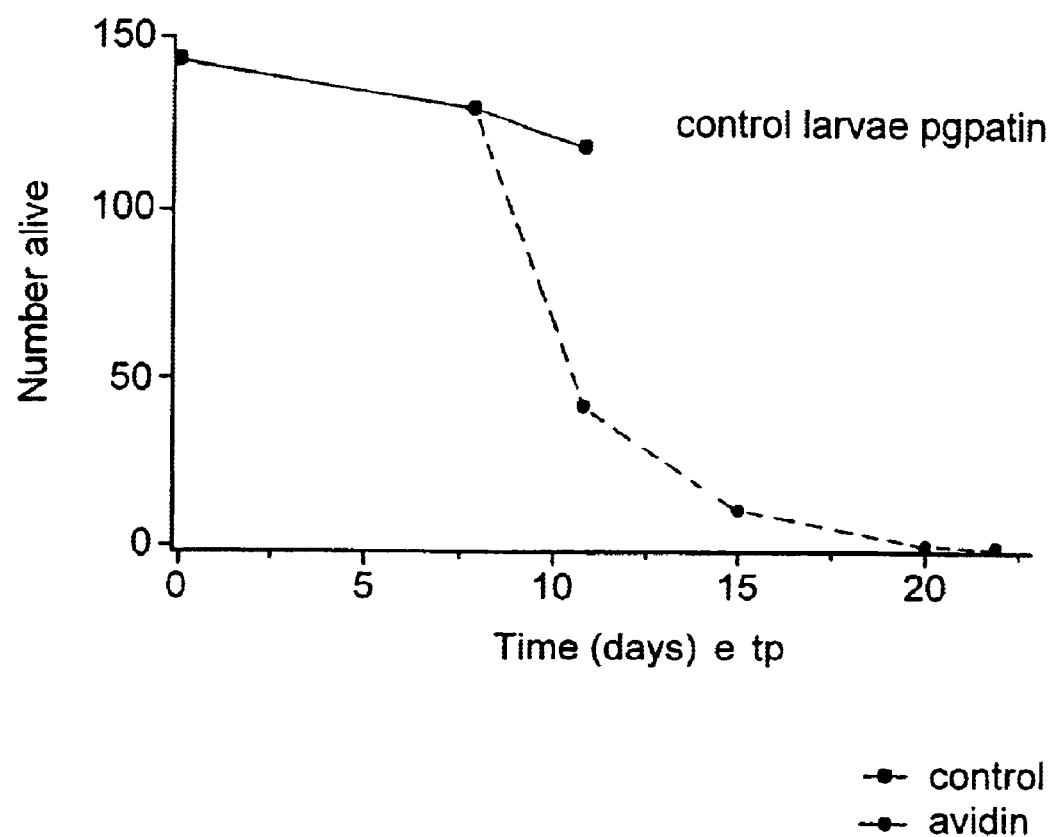
FIG. 23 shows the survival of larvae of the cotton bollworm (corn earworm, tomato fruitworm), *Helicoverpa armigera*, fed tobacco leaves expressing avidin.
Figure 24:
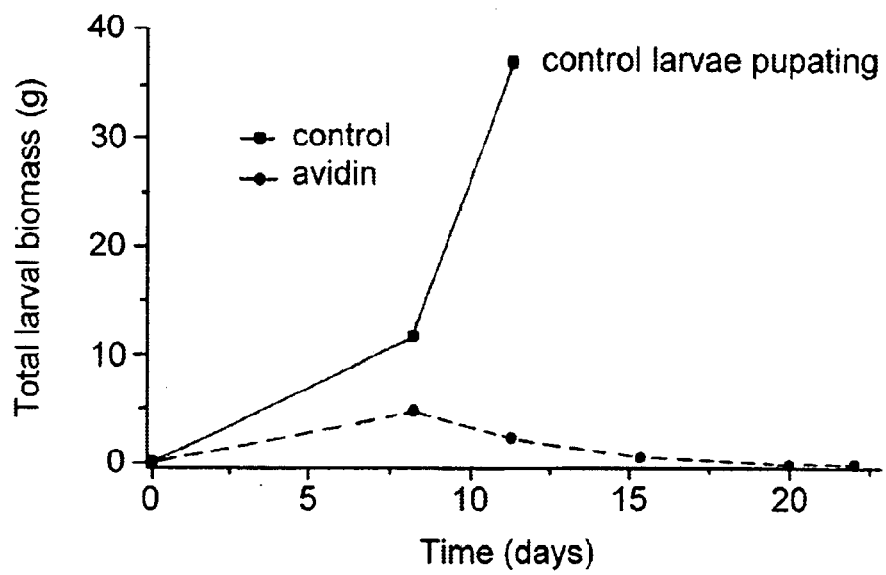
FIG. 24 shows the accumulation of biomass of larvae of the cotton bollworm (corn earworm, tomato fruitworm), *Helicoverpa armigera*, fed tobacco leaves expressing avidin.

Results:
S. litura
  As the same pattern of response was observed in larvae on all control lines, results from the different lines were pooled. The same observation was made for larvae on all avidin lines, so results from these lines were also pooled.
  Larvae on avidin-expressing plants were significantly smaller than controls at the first weighing on Day 8 (control plants: N=153, mean weight=0.0304 g, s.e.=0.0014; avidin plants: N=160, mean weight=0.0151 g, s.e.=0.0007; P<0.001) (FIG. 19), (ANOVA, Payne et al., 1993),but there were no differences in survival at that time. By Day 12, larvae eating avidin plants had begun to die (P<0.001) (FIG. 20), and there were clear differences in mean weight and total live biomass present on the two treatments (P<0.001) (FIG. 21). By Day 15, these differences were even more pronounced, and after this time control larvae had pupated, so no further control measurements were taken. Comparative larval sizes on control and avidin plants are shown on Day 15 in FIG. 19B. Differences in size and plant damage on Day 15 are shown in FIG. 19C. Larvae on avidin plants steadily diminished in numbers and total biomass, and by day 25 all had died.
  We observed that larvae feeding on avidin plants were unable to successfully complete the process of moulting from one instar to the next. Larvae on these plants appeared to stop feeding during ecdysis, and to then turn black and die while still attached to a partially shed larval skin.
H. armigera
  As with S. litura, larval responses on all control lines were the same, and results were thus pooled, as were responses on all avidin lines. H. armigera larvae fed avidin-expressing plants were smaller than those fed control plants by Day 8 (control plants: N=130, mean weight=0.0909 g, s.e.=0.0031; avidin plants: N=130, mean weight=0.0375 s.e.=0.0013; P<0.001) (FIG. 22). Three days later, control larvae had continued to grow well while avidin-fed larvae had begun to die (P<0.001) (FIG. 23), and differences in biomass between the two treatments were extreme (P<0.001) (FIG. 24). No further control measurements were made after Day 11 as larvae had begun to pupate. Comparative larval sizes on control and avidin are shown on Day 14 in FIG. 22B.

Differences in size and plant damage on Day 14 are shown in FIG. 22C. By Day 22, all larvae on avidin plants had died.

As with *S. litura*, *H. armigera* larvae on avidin plants often died during the moulting process.

Conclusions:

The expression of avidin in six different transgenic lines of tobacco was fatal to larval *S. litura* and *H. armigera*. Larvae of both these lepidopteran pest species grew rapidly and pupated on a range of non transgenic and transgenic tobacco lines which did not express avidin. Larvae fed avidin-expressing plants were unable to develop normally or attain significant biomass, often dying during early instar moults.

These results provide further evidence of the effectiveness of the avidin construct described in this patent in protecting the plant in which it is expressed from insect damage.

EXAMPLE 9

Toxicity of Avidin Expressed at a Range of Concentration Levels in Tobacco (*Nicotiana tabacum*) Leaves to Larvae of the Cotton Boll Worm (Tomato Fruitworm, Cornear Worm) *Helicoverpa armigera* (*Lepidoptera*: Noctuidae)

Constructs:
Control Lines:
Non-transformed Control Plants:
48 plants (NT 101-NT 148).

These were grown from seeds produced by selfed NT plants 11–14 which were used in the trial described in Example 8.

Avidin-expressing Lines:

Tobacco plants ($T_1$) were grown from seeds collected from 3 selfed plants from the clonal lines PLA2/7, PLA2/9 and PLA2/13. These $T_0$ parental plants had been transformed with the avidin gene with a PPI-I targeting sequence (Example 2 above), and were used in the trial described in Example 8. Twenty four plants from each of these three $T_1$ seed lines were grown for the experiment and 25 of these 72 plants were selected for use depending on their level of avidin expression.

Insects:

Neonate *H. armigera* larvae from our laboratory colony (see Example 8) were placed on the leguminous host plant *Lotus corniculatus* and kept at 18° C. for 34 days prior to the experiment. Late first instar larvae were then transferred to control and avidin-expressing tobacco leaves. Initial larval weight was determined as the mean of the individual weights of a randomly selected sample of 48 larvae weighed at the beginning of the experiment.

Trial Design:

To measure the effect of avidin expression level on the growth, survival and biomass of *H. armigera* larvae, the 72 $T_1$ avidin plants described above were tested for expression level using the ELISA method (Example 5). A leaf sample of approximately 50–60 cm² was removed from the tip of Leaf 4 of each plant for this process. All plants were ranked according to their expression level, and divided into six groups representing six non-overlapping ranges of expression level, from "high" to "low". These six groups of plants were assigned as six treatments with different mean avidin concentrations (Table 6).

At the start of the trial, the highest expressing plant from each treatment group and two control plants of similar physiological form were selected. Leaf numbers were assigned on each plant as described in Example 8, and Leaves 1 and 2 cut from each plant for use in the trial. Petioles were again immersed inserting in agar to maintain leaf freshness, and 12 *H. armigera* larvae were placed on the underside of each leaf.

As in Example 8, leaves were stored in plastic boxes, and the experiment conducted at 24.5±1° C. and 60% relative humidity, with a 16:8 h light:dark cycle.

Larvae were weighed on Days 8, 11, 13, 14 and 15, and surviving larvae were transferred to fresh leaves 1 and 2 from the next highest expressing plant in each treatment croup on Days 6, 8, 11 and 16. To ensure that larvae could feed ad libitum, additional leaves were cut from positions immediately above or below Leaves 1 and 2 on the same plants, and provided to larvae if necessary. Control larvae required many more leaf additions than all other treatments, and thus were given additional leaves from a range of control plants and leaf positions.

TABLE 6

Expression levels of avidin in treatment groups of plants used in trial

| Treatment | Mean expression level of avidin ($\mu$M) | Standard error | Number of plants used |
|---|---|---|---|
| 1 | 17.25 | 0.44 | 5 |
| 2 | 14.18 | 0.09 | 4 |
| 3 | 10.85 | 0.07 | 4 |
| 4 | 8.71 | 0.12 | 4 |
| 5 | 6.40 | 0.12 | 4 |
| 6 | 3.69 | 0.11 | 5 |
| Control | 0 | — | 48 |

Results:

As there were no significant differences between larval growth, survival and biomass on the two control treatments, the results of these two treatments were combined.

Figure 25:
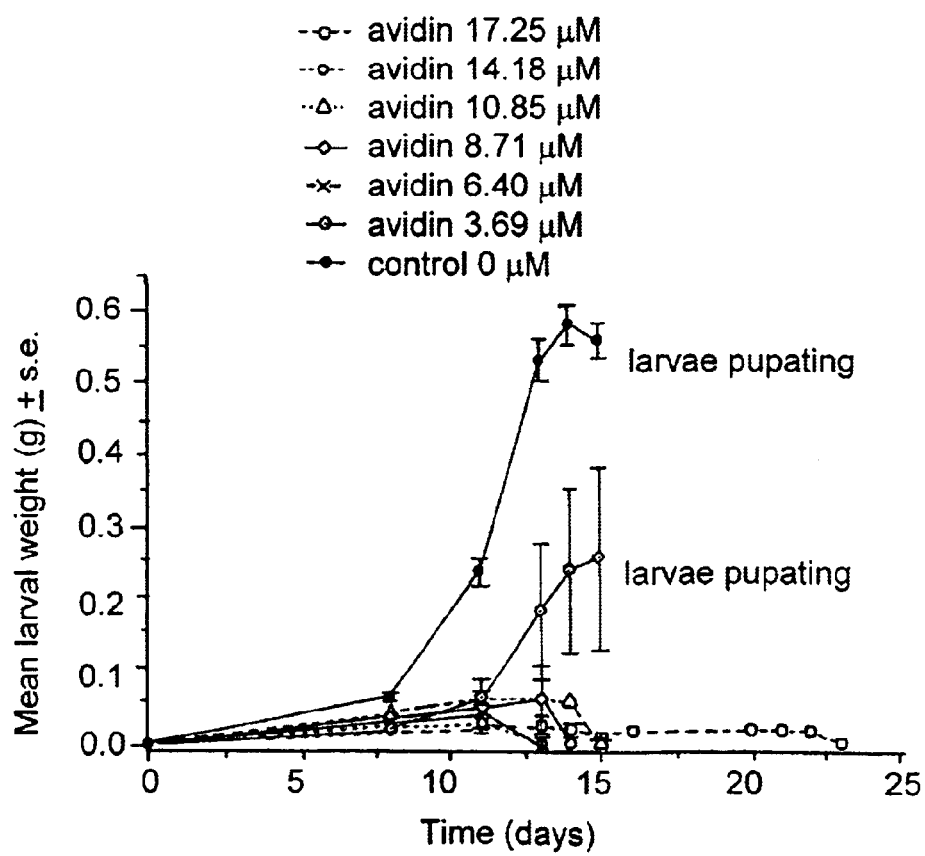
FIG. 25 shows the effect of the level of avidin expression in tobacco on the growth of larvae of the cotton bollworm (corn earworm, tomato fruitworm), *Helicoverpa armigera*.

By the time larvae were first weighed on Day 8 of the experiment, control larvae had grown larger than those in all other treatments (FIG. 25) ($P<0.05$–$P<0.0001$) (ANOVA., Payne et al, 1993). These differences increased with time.

Comparison of larval survival curves using a log-rank test (Kalbfleisch and Prentice, 1980) showed that survival on all avidin-expressing lines was significantly reduced in comparison with control survival ($P<0.001$). There were no significant differences between survival on any of the six lines expressing avidin at different levels ($P=0.328$).

Figure 26:
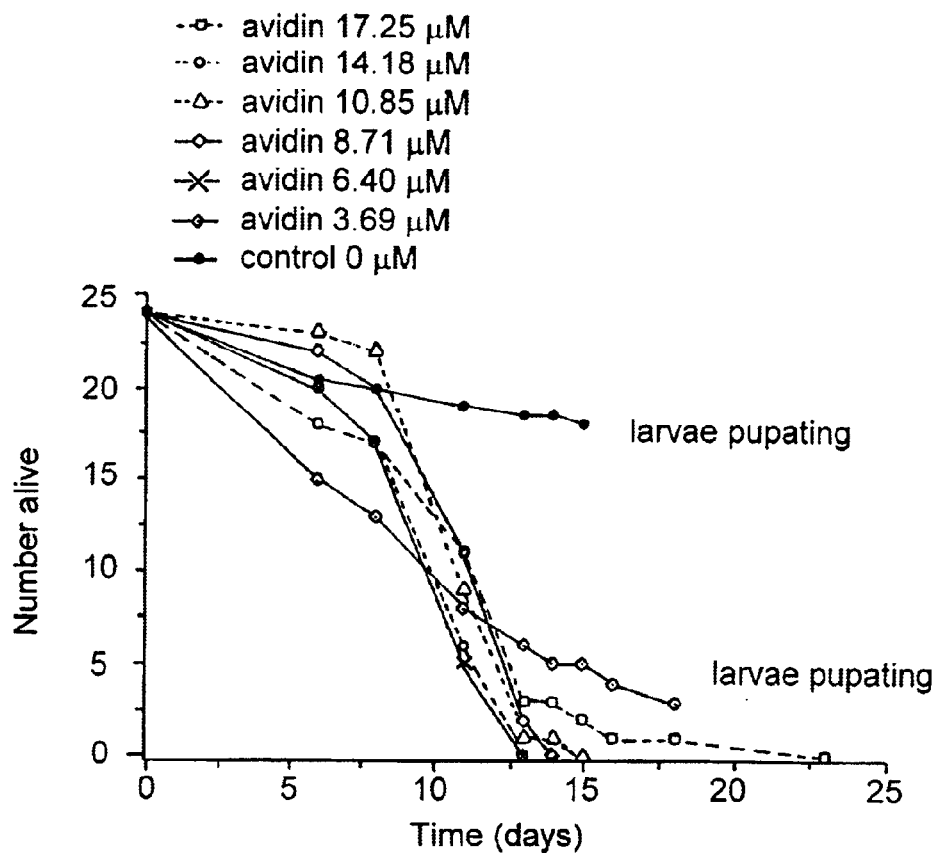
FIG. 26 shows the effect of the level of avidin expression in tobacco on the survival of larvae of the cotton bollworm (corn earworm, tomato fruitworm), *Helicoverpa armigera*.
Figure 27:
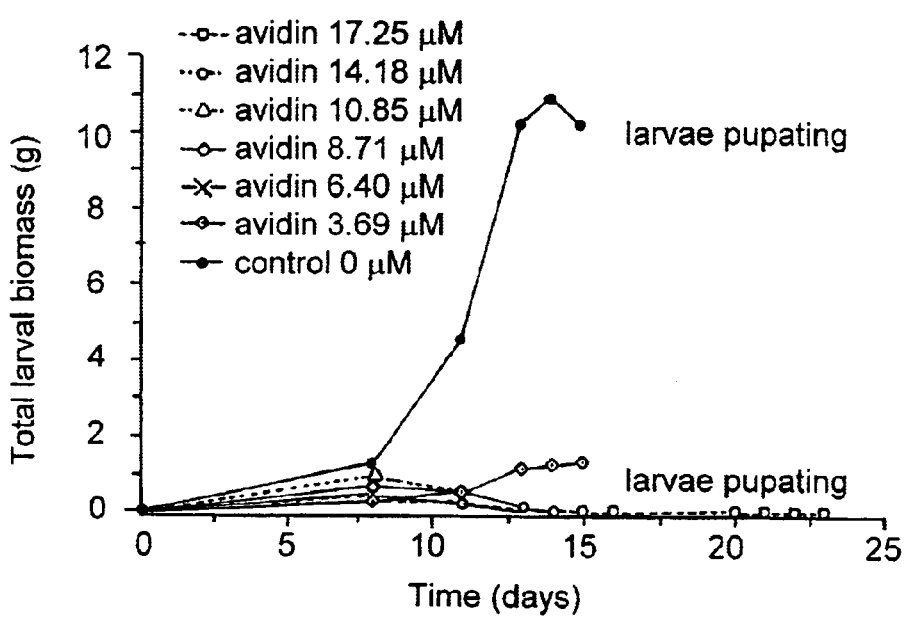
FIG. 27 shows the effect of the level of avidin expression in tobacco on the accumulation of biomass of larvae of the cotton bollworm (corn earworm, tomato fruitworm), *Helicoverpa armigera*.

All the larvae fed plants expressing avidin at 17.25–6.40 M failed to achieve substantial growth, and died, often during moulting, without pupating (FIG. 26). Two of the 24 larvae on the lowest expressing avidin treatment pupated, although they were smaller than control larvae. One of these pupae emerged as a moth. On the two control treatments, 31 of 48 larvae successfully pupated and 19 of these emerged as moths. The number of larvae successfully pupating in the control treatments was reduced by cannibalism of prepupae by voracious late instar larvae. This effect may also have reduced the rate of emergence of moths from pupae in the controls. No such effect occurred in the avidin treatments because of the extremely high larval death rate caused by the ingestion of avidin-expressing leaf material.

Accumulation of biomass on the avidin-expressing lines was negligible compared to that on the control lines (Fic. 27).

Conclusions:

Tobacco plants expressing avidin at levels ranging from 6.40 to 17.25 $\mu$M caused total mortaliry of *H. armigera* larvae in this trial. Expression levels of 3.69 $\mu$M resulted in a very high level of larval mortality (92%). All plants expressing avidin at any level were protected from insect attack as evidenced by the extremely low biomass of insects on those plants.

EXAMPLE 10

Toxicity of Avidin and Streptavidin Incorporated into Artificial Diets to the Pine Shoot Tip Moth, *Rhyacionia Buoliana* (*Lepidoptera*: Tortricidae)

Insects:

A laboratory colony of *Rhyacionia buoliana* was established by field collection of late instar larvae and pupae from pine (*Pinus radiata*) plantations throughout Chile. Field-collected individuals which became adults were confined in laboratory cages to allow mating. Eggs laid by adult females were collected, and larvae which emerged from these were used in this trial.

Methods:

The avidin used in this experiment was a Calbiochem® product purchased from Calbiochem-Novabiochem Corporation, La Jolla, Calif. 92039. It was lyophilized avidin from egg white, Product Number 189725, Lot Number 276992.

The streptavidin was also obtained from Calbiochem-Novabiochem Corporation, and was a lyophilized solid, Product Number 189730, Lot Number B19870.

Avidin and streptavidin were incorporated into artificial diet at the following concentrations in eight treatments:
1. control, 0 µg/mL
2. control, 0 µg/mL
3. avidin, 50 µg/mL
4. avidin, 100 µg/mL
5. avidin. 1000 µg/mL
6. streptavidin. 50 µg/mL
7. streptavidin, 100 µg/mL
8. streptavidin. 1000 µg/mL These levels are equivalent to plant expression of 3.2, 6.4 and 64 µM of avidin, and 3.0, 6.1 and 60.6 µM of streptavidin. We have shown avidin expression levels in tobacco ranging from 3–25 µM (Examples 8, 9 and 18), and streptavidin levels of 11–24 µM (Example 7).

The artificial diet used in this experiment was a general purpose insect rearing diet based on the recipe of Singh (1983). The avidin and streptavidin were added in aqueous solution into freshly made diet, which had cooled to 60° C.

The experiment was run in a randomised complete block design, in three blocks, which were set up on consecutive days. Both avidin and streptavidin, at each of the three doses, were fed to a total of 90 larvae, and 180 larvae were given control diet:
i.e. 2 proteins×3 concentrations×30 larvae×3 blocks=540 larvae+2 controls×30 larvae×3 blocks=180 larvae Within 12 h of hatching from eggs, neonate larvae were placed in pottles containing BIO-SERV® pine tip moth diet (the diet on which the colony was reared).

At the beginning of the experiment, healthy 24 h-old larvae which had established well on this diet were then transferred to 1.5 mL Eppendorf tubes containing a 0.25 ml block of treatment diet, where they were confined individually. Initial mean larval weight was determined by weighing 100 of these healthy larvae selected for the experiment en masse.

Larval survival was checked every seven days for the duration of the experiment. After 14 days, larvae were weighed and transferred to new tubes with 1 µL of fresh diet. After 35 days, surviving larvae were weighed again, and the experiment terminated.

This experiment was conducted in a temperature-controlled incubator set at 20° C., in which lights periodically switched on when the temperature dropped below the target.

Results:

As there were no significant differences between data collected for the three blocks of any given treatment, results for the three blocks were pooled within all treatments.

Figure 28:
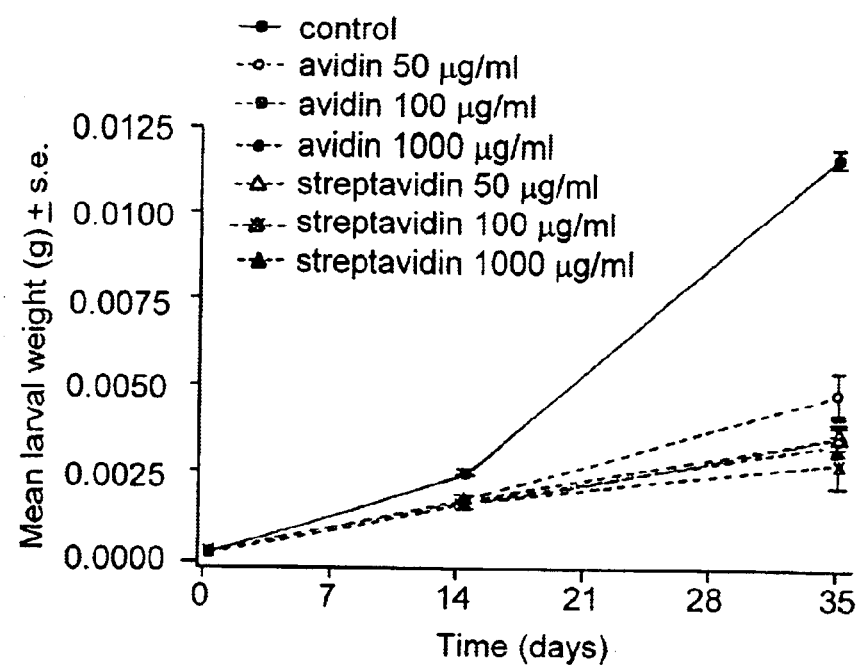
FIG. 28 shows the effect of avidin and streptavidin incorporated into insect diet at three concentrations on the growth of larvae of the pine shoot tip moth, *Rhyacionia buoliana*.
Figure 29:
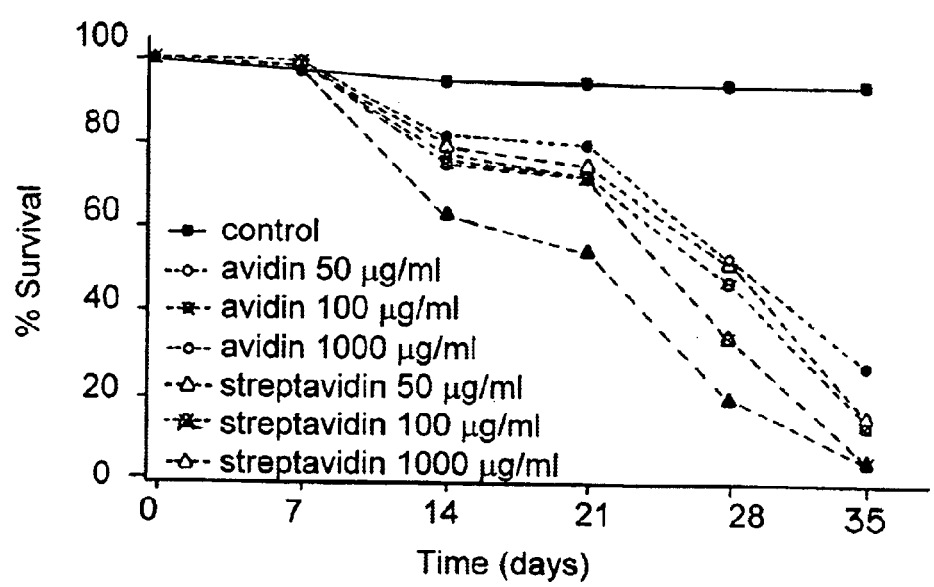
FIG. 29 shows the effect of avidin and streptavidin incorporated into insect diet at three concentrations on the survival of larvae of the pine shoot tip moth, *Rhyacionia buoliana*.
Figure 30:
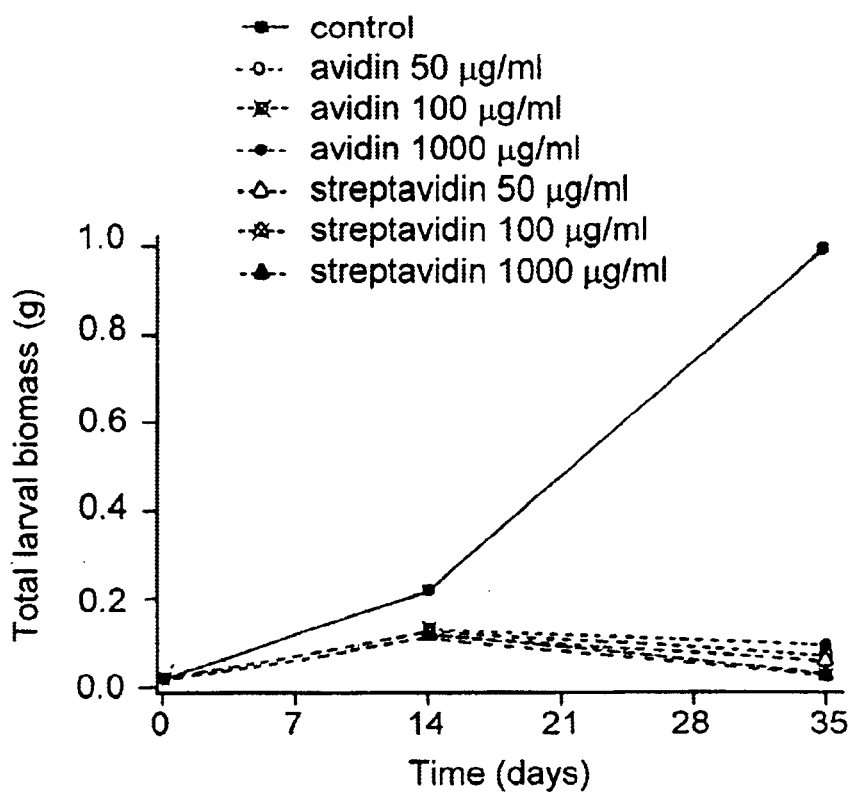
FIG. 30 shows the effect of avidin and streptavidin incorporated into insect diet at three concentrations on the accumulation of biomass of larvae of the pine shoot tip moth, *Rhyacionia buoliana*.

Both avidin and streptavidin at all 3 concentrations had caused significant reductions in larval growth by Day 14 (FIG. 28) ($P<0.0001$) (ANOVA, Payne et al., 1993), and these differences increased by Day 35. Both proteins were toxic to larvae, and most individuals feeding on an avidin or a streptavidin diet were dead before the end of the experiment (FIG. 29). Many of the dead larvae had died during the process of moulting from one instar to the next. Larvae that survived feeding on diet containing either protein at any of the three concentrations were close to death. Comparison of survival curves using log-rank tests showed all treatments reduced larval survival compared with controls ($P<0.001$). The highest dose of streptavidin killed larvae faster than any of the other treatments ($P<0.001$), but there were no other differences among the survival responses to other doses of either protein. Because both avidin and streptavidin killed most larvae and prevented growth in survivors, there were very large differences between insect biomass on controls and all other treatments (FIG. 30).

Conclusions:

This trial has demonstrated the high level of toxicity of both avidin and streptavidin to the pine shoot tip moth, *Rhyacionia buoliana*. These results suggest that either of these proteins would control the pest if expressed in *P. radiata* or other host trees at levels equivalent to those we have demonstrated for avidin and streptavidin in tobacco plants (Examples 7, 8, 9 and 18).

EXAMPLE 11

Toxicity of Avidin-painted Willow (*Salix fragilis*) Leaves to Neonate Willow Sawfly Larvae (*Nematus oligospilus*) (*Hymenoptera*: Tenthredinidae).

Insects:

Willow sawfly larvae (*Nematus oligospilus*) which had hatched within the previous 24-hour period, were obtained from a laboratory colony reared on small potted willow plants (*Salix fragilis*).

Leaf Material:

Leaves were obtained from potted willow plants (*S. fragilis*) grown in a shade house, the same source as those on which the larvae were reared.

Methods:

The avidin used in this trial was a Calbiochem® product, purchased from Calbiochem-Novabiochem Corporation, La Jolla, Calif. 92039. It was lyophilized avidin from egg white, Lot 276992.

Willow leaves were weighed and a mean leaf weight obtained (194.5±13.1 mg). Using this weight the amount of avidin to apply per leaf was calculated as 65 and 130 µM delivered as 200 and 400 µg avidin/leaf.

To ensure avidin was well distributed over the leaf surfaces it was dissolved in a 0.1% solution of the "wetter and sticker", BondXtra® (i.e. 50 µL in 50 mL). 100 µL/leaf gave good coverage.

Solutions were painted on to leaves using a sable brush (Cirrus 110®). The brush was weighed before and after applying the solutions to the leaves and was found to absorb about one-tenth of the volume. Hence 55 µL of each solution was pipetted on and applied to each side of each willow leaf. Leaves were allowed to air dry.

Trial Design:

Excised leaves were trimmed to fit across a Petri dish, one leaf per dish. The leaf petiole was placed in a small tube of water and painted with the appropriate solution. After being air-dried, the leaf was then pushed through a hole in the side of the Petri dish. Water was topped up every 2 days. Close cell foam supported the petiole and filled the space around the hole preventing the larvae escaping. The Petri dish with tube attached was stuck to a backing board with Blu-tack® and held firmly in place with a rubber band. The whole set up was then set vertically on a slotted board. Each Petri dish contained one willow leaf and one larva and each treatment tested 20 larvae. There were four treatments:
1. controls in which leaves were untreated,
2. 0.1% BondXtra®,
3. 65 µM avidin in 0.1% BondXtra®,
4. 130 µM avidin in 0.1% BondXtra®.

Larvae were weighed individually and one placed in each Petri dish containing a single willow leaf. Surviving larvae were weighed again after 7, 14 and 21 days and leaves were changed after 10 and 15 days.

Figure 31:
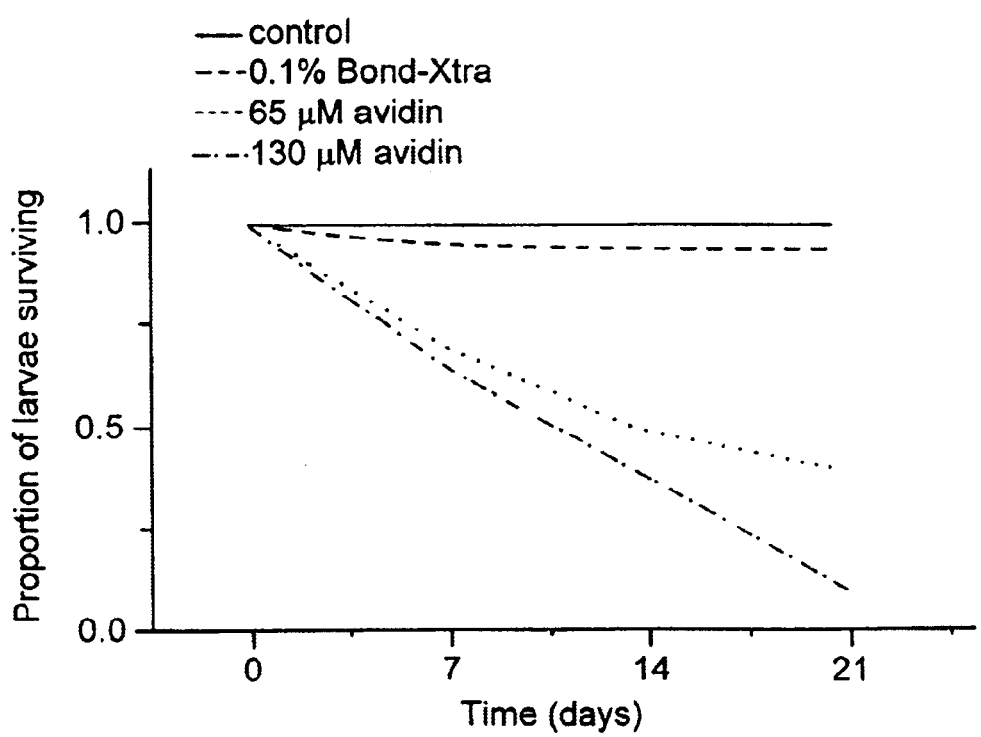
FIG. 31 shows the effect of avidin-painted willow leaves on the survival of larvae of the willow sawfly, *Nematus oligospilus*.
Figure 32:
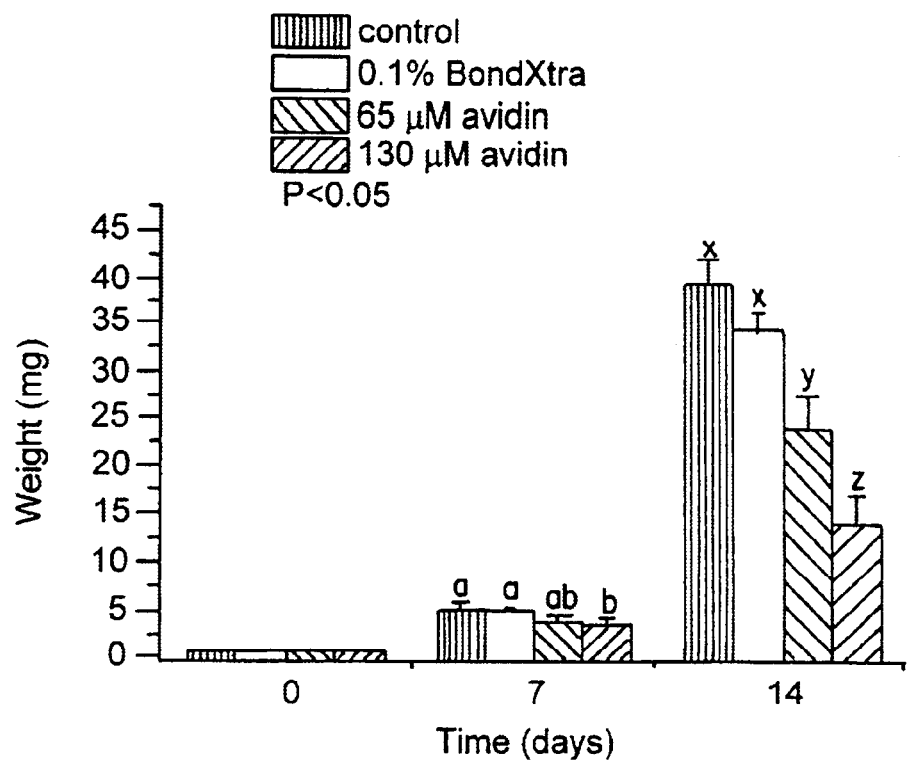
FIG. 32 shows the effect of avidin-painted willow leaves on the weight gain of larvae of the willow sawfly, *Nematus oligospilus*.

Results:

FIG. 31 shows survival of sawfly larvae over the first 21 days by which time the majority of survivors had pupated. Whilst no controls died and only one death was recorded amongst larvae treated with BondXtra® survival of larvae on leaves coated with avidin declined steadily. The proportion of sawfly larvae surviving to 21 days on leaves coated with 65 µM avidin was 0.4, and 130 µM avidin only 0.1. Further, weight gain over the first 14 days was significantly reduced at both avidin concentrations when compared to control larvae and those feeding on leaves treated with BondXtra® alone (FIG. 32).

Figure 33:
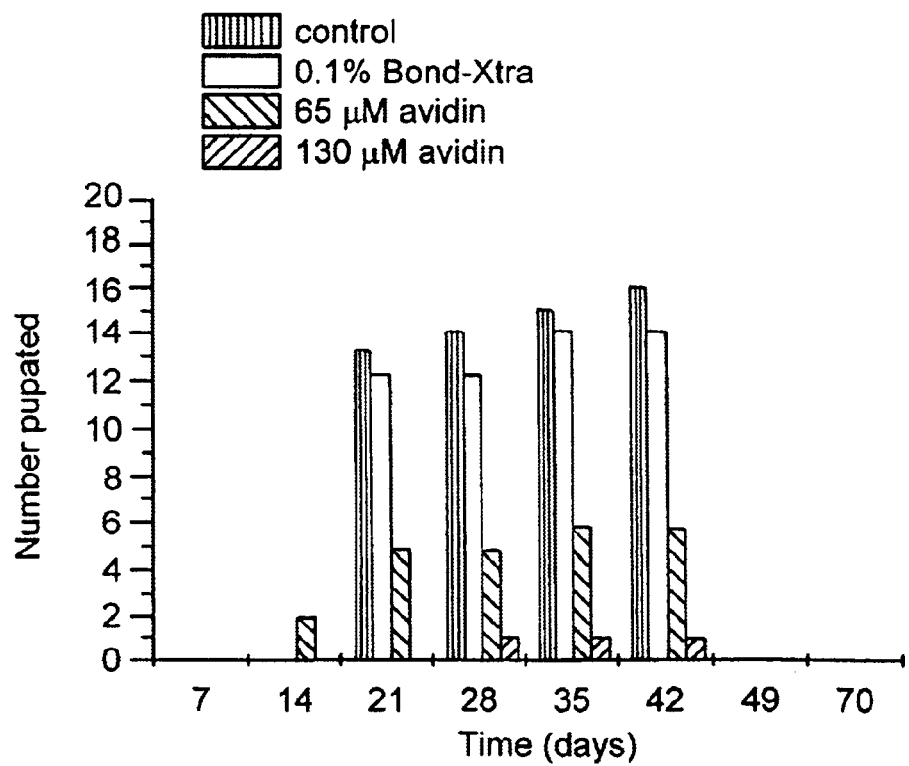
FIG. 33 shows the effect of avidin-painted willow leaves of the formation on the pupae of the willow sawfly, *Nematus oligospilus*.
Figure 34:
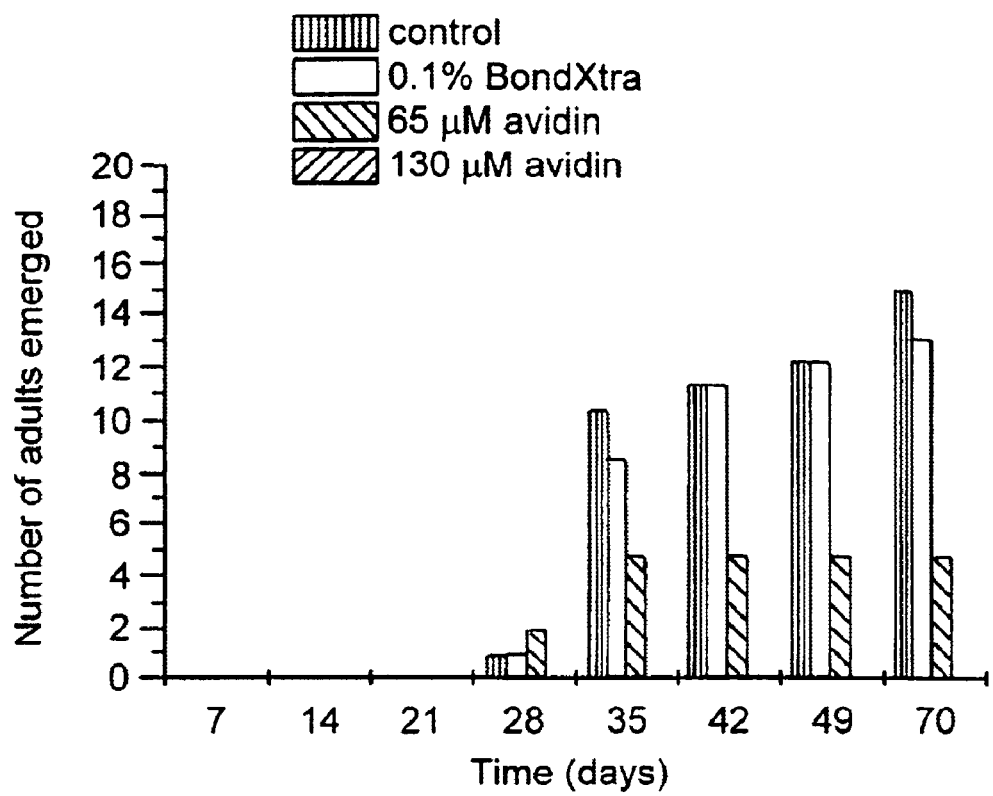
FIG. 34 shows the effect of avidin-painted willow leaves on the emergence of adults of the willow sawfly, *Teleogryllus commodus*.

At pupation, sawfly larvae form a fibrous pupal case or cocoon. At the lower avidin concentration only one out of the six larvae that reached pupation and developed a cocoon failed to emerge as an adult. At the higher avidin concentration, only one larvae attempted and failed to pupate; no adults emerged from this treatment (FIGS. 33 and 34). In both cases where the larva failed to emerge as an adult the fibrous pupal case contained a shrivelled dead larval body and so ecdysis (moult) had not been completed.

Conclusions:

Avidin is highly insecticidal to willow sawfly larvae and, as has been observed in bioassays with this protein on other insect species (see other examples), it appears to have acted both as a growth inhibitor and as a moulting inhibitor.

EXAMPLE 12

Toxicity of Avidin-Painted Lettuce (*Latuca sativa*) Leaves to the Black Field Cricket, *Teleogryllus commodus* (Orthoptera: Gryllidae)

Insects:

Crickets were obtained from a laboratory colony of *Teleogryllus commodus* originally field collected in Northland, New Zealand. Four day old nymphs were used in this trial. These individuals had been fed since eclosion from eggs on the normal colony diet for young nymphs of rolled oats, dried lucerne (*Medicago sativa*) meal and dog biscuits (Pedigree® PAL Meaty-Bites®).

Methods:

The avidin used in this trial was a Calbiochem® product, purchased from Calbiochem-Novabiochem Corporation. La Jolla, Calif. 92039. It was lyophilized avidin from egg white, Lot 276992.

Green distal portions of leaves from organically grown lettuce leaf were cut into sections approximately 4×4 cm. These were painted on both sides with three different solutions, providing three treatments:
1. Control solution of 0.1% (v:v) BondXtra®, a wetting, spreading and sticking agent
2. 4.8 µM avidin (75 µg/g fresh weight of lettuce leaf) in 0.1% (v:v) BondXtra®
3. 19.2 µM avidin (300 µg/g fresh weight of lettuce leaf) in 0.1% (v:v) BondXtra®

Cricket nymphs were weighed and placed individually in 75 mL specimen pottles with ventilation holes punched in their lids, and with a 42.5 mm filter paper disc placed in the bottom of each pottle to absorb excess moisture. Food was replaced as necessary so that crickets could feed ad libitum on fresh leaf material. Each cricket was weighed weekly until all individuals feeding on the avidin-painted leaves had died.

Figure 35:
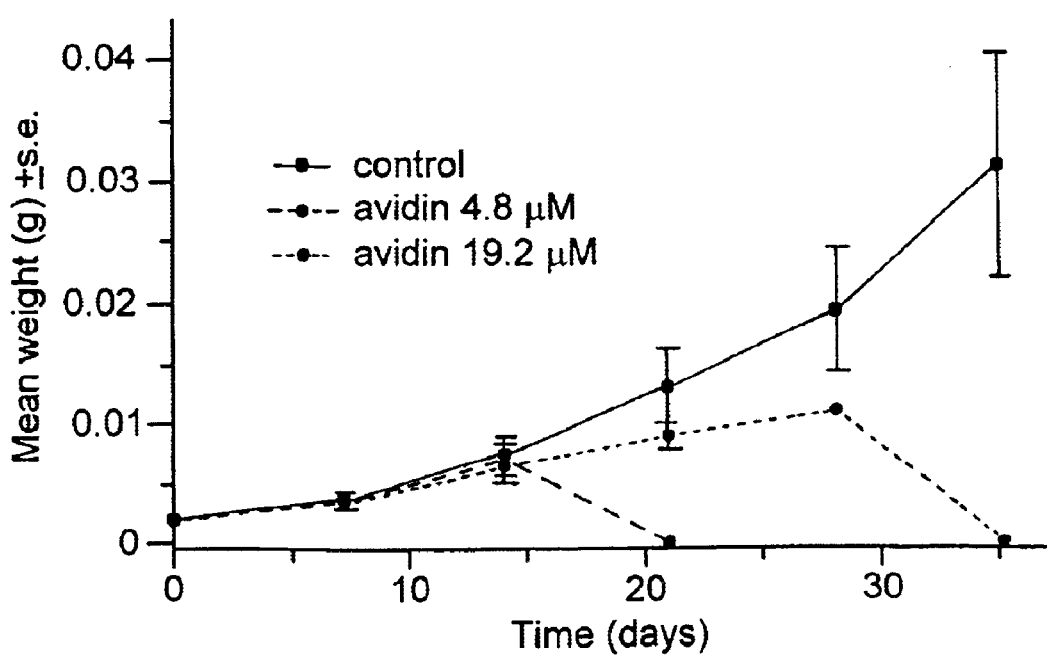
FIG. 35 shows the effect of avidin-painted lettuce leaves the growth of nymphs of the black field cricket, *Teleogryllus commodus*.
Figure 36:
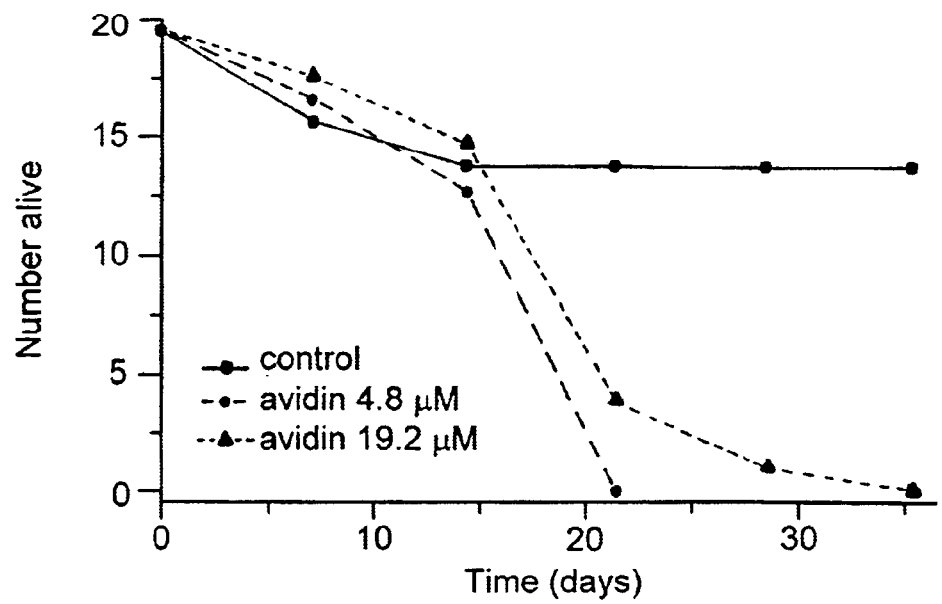
FIG. 36 shows the effect of avidin-painted lettuce leaves on the survival of nymphs of the black field cricket, *Teleogryllus commodus*.
Figure 37:
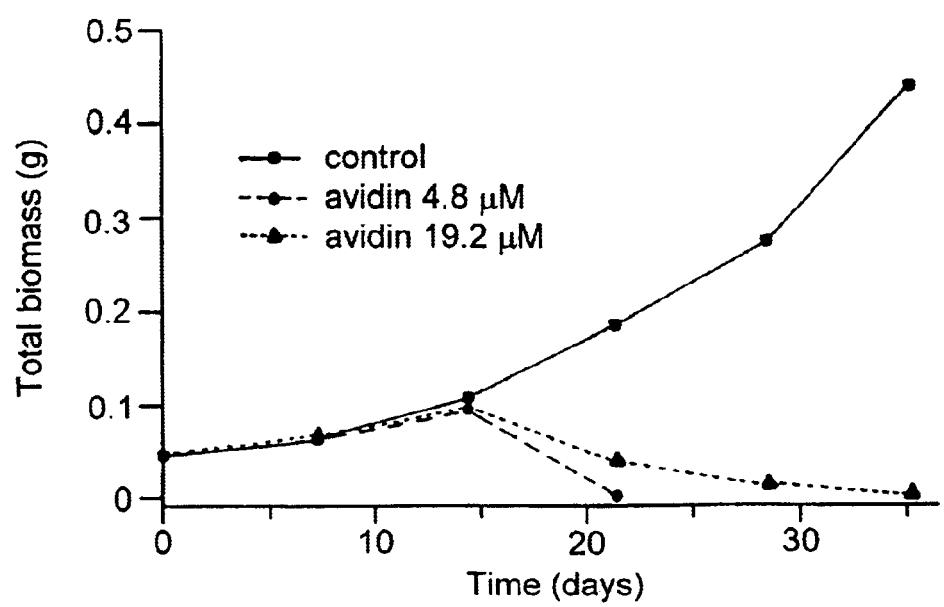
FIG. 37 shows the effect of avidin-painted lettuce leaves on the accumulation of biomass of nymphs of the black field cricket, *Teleogryllus commodus*.

Results:

Crickets grew well on control leaves but poorly on leaves painted with avidin at both concentrations (FIG. 35). By Day 21 control crickets were significantly larger than those surviving avidin treatment (P<0.05) (ANOVA, Payne et al. 1993). By this time, all those on 4.8 µM avidin leaves were dead (FIG. 36) and there were few survivors on the 19.2 µM avidin treatment. By Day 35, all crickets on the 19.2 µM treatment had also died. Many of the avidin-fed crickets died while moulting from one nymphal stage to the next. Cricket biomass in the control treatment steadily increased throughout the experiment, while biomass had reached zero in the 4.8 µM avidin treatment by Day 21, and dropped below the starting value in the 19.2 µM treatment by this time (FIG. 37). Biomass in the 19.2 µM treatment fell to zero soon after this.

Conclusions:

Avidin is highly toxic to the black field cricket, demonstrating the efficacy of this protein as a means of controlling orthopteran pests. This suggests the use of avidin-expressing plants as a means of controlling pests such as locusts and grasshoppers as well as crickets.

EXAMPLE 13

Toxicity of Artificial Diet Containing Streptavidin to Neonate Clover Root Weevil (*Sitona lepidus*) (Coleoptera: Curculionidae) and Neonate Argentine Stem Weevil (*Listronotus bonariensis*) (Coleoptera: Curculionidae)

Insects:

Eggs of both weevil species were obtained from field-collected adults maintained on white clover, *Trifolium repens*, (for *Sitona lepidus*) and ryegrass, *Lolium perenne*, (for *Listronotus bonariensis*) foliage.

*S. lepidus* eggs were placed in Petri dishes on filter paper moistened with sterile distilled water and allowed to hatch at 25° C. To delay hatching until sufficient eggs had been laid for a trial, some eggs were stored for up to 24 days at 10° C., before being brought to the higher temperature for hatching.

*L. bonariensis* eggs were placed directly onto blocks of artificial diet in small plastic containers (4 mL autoanalyser cups), one larva per cup.

Streptavidin:

The streptavidin used in this trial was obtained from Calbiochem-Novabiochem Corporation, and was a lyophilized solid. Product Number 189730. Lot Number B19870.

Diets:

An artificial diet (ASW diet) known to be suitable for rearing *L. bonariensis* (Malone and Wiley, 1990) was modified by omitting biotin from the recipe and used in the streptavidin trials for both weevil species.

To test the diet's suitability for *S. lepidus* trials, some of the first neonate *S. lepidus* larvae obtained were placed onto blocks of unmodified ASW diet (with biotin) for three days prior to being used in the first replicate of the streptavidin feeding trial. Other larvae in this trial had been maintained for the first three days of life on either washed clover roots or a second artificial diet, which also contained biotin (porina diet) (Burgess et al. 1993). As larval feeding was observed only on ASW diet, a "biotin-free" version this diet was used in the subsequent streptavidin trial. Neonate *S. lepidus* larvae used in the second and third replicates had had no previous exposure to diets or natural foods containing biotin, but were used directly in the streptavidin trial.

Trial Designs:

*S. lepidus*

For the *S. lepidus* streptavidin trial, neonate or 3-day-old larvae were transferred individually to wells of microtitre trays containing "biotin-free" ASW diet. Three replicates were set up, each consisting of 100 larvae receiving a streptavidin treatment and 100 larvae as controls. For the 'treatment' group, 0.9 mg/mL streptavidin (55 $\mu$M) was blended thoroughly into the diet before it was dispensed into the wells. Control larvae received "biotin-free" ASW diet without any additive. Microtitre trays containing the diets were first covered by an ironed-on layer of Mylar® film. Larvae were then introduced into each well via slits cut in the Mylar® and then sealed in by a second covering, this time of Frisk® adhesive film. They were observed daily for signs of feeding, burrowing and movement.

After 11 to 25 days, the films were removed from the trays and each larva was picked out of the diet and placed individually on a small cut block of the same diet in an autoanalyser cup (4 mL). Any deaths were recorded at this time and at approximately weekly intervals thereafter until the end of the experiment (94 days for Replicate 1:80 days for Replicate 2 and 78 days for Replicate 3).

*L. bonariensis*

For the *L. bonariensis* streptavidin trial, "biotin-free" ASW diet was made up as before, with the addition of 0.9 mg/mL streptavidin (55 $\mu$M) for the treatment group. Three replicates, each consisting of 31 streptavidin-fed and 31 control larvae, were set up. For these weevils, each egg was placed directly on a cut block of the appropriate diet in an autoanalayser cup (4 mL) and sealed with its plastic lid. They were examined daily to observe larval hatching, feeding, burrowing or movement. At approximately weekly intervals the containers were opened, the diet block teased apart and larval deaths recorded. Fresh diet of the same type was provided when required. The experiment was ended after 51 days, when many of the control insects were still alive.

Results:

*S. lepidus*

Figure 38:
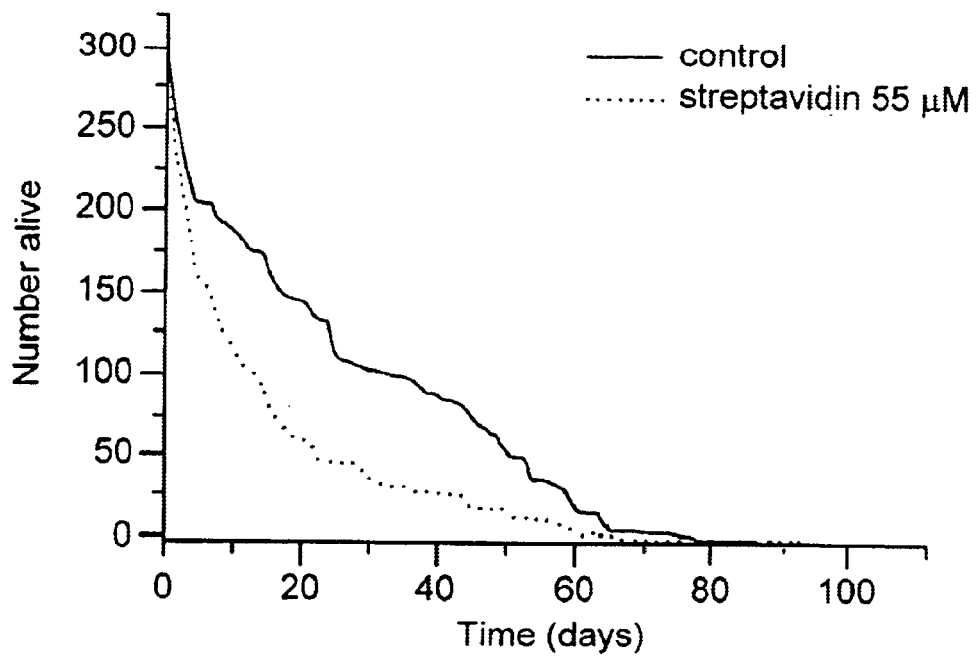
FIG. 38 shows the effect of streptavidin incorporated into insect diet on the survival of neonate larvae of the clover root weevil, *Sitona lepidus*.

In each replicate, larval survival was significantly lower for weevils feeding on diet with 55 $\mu$M streptavidin added than for the control weevils ($P<0.001$, log-rank tests to compare survival curves (Kalbfleisch and Prentice, 1980)). FIG. 38 shows the survival curves for all replicates combined. Many of the larvae in the streptavidin treated group appeared to have died during or immediately after a larval moult. Dead larvae often had a soft, transparent head and the darker discarded head capsule attached to the rear of the insect.

Table 7 shows the median survival times for each group of weevils. Weevils in Replicate 1 had better survival than those in Replicates 2 and 3. This may be due to the Replicate 1 weevils receiving either clover roots or ASW or porina diet with biotin aided for three days before the start of the trial. In each case however, larvae treated with streptavidin died significantly sooner than the control larvae.

Control survival was poorer than might be expected for weevils in the field and only four control weevils developed into adults before the end of the experiment, probably because ASW diet was not the ideal medium for rearing this insect. No adults emerged among the clover root weevils fed streptavidin.

*L. bonariensis*

Figure 39:
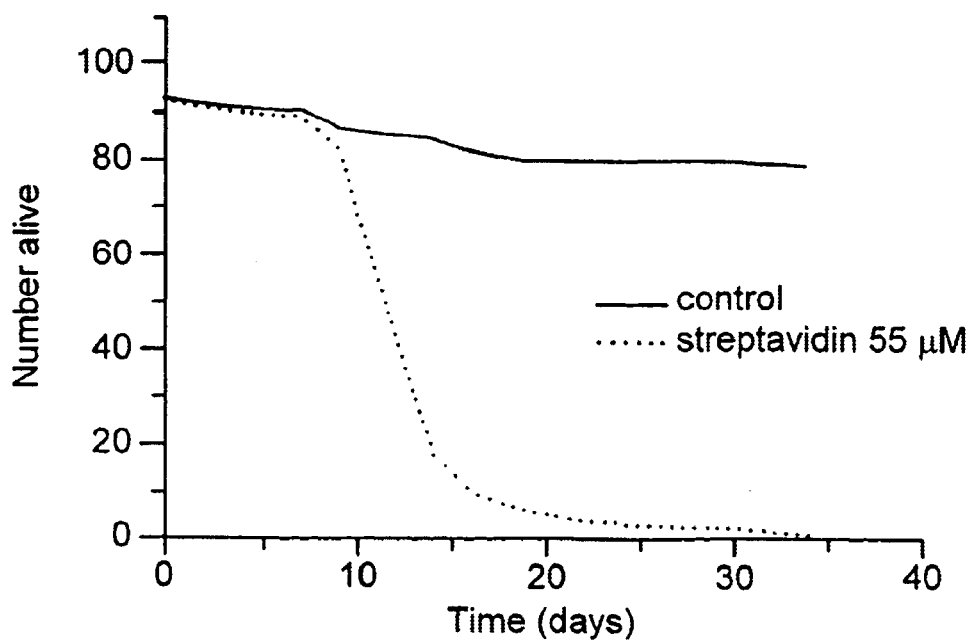
FIG. 39 shows the effect of streptavidin incorporated into insect diet on the survival of larvae of the Argentine stem weevil, *Listronotus bonariensis*.

In each replicate, larval survival was significantly lower for the weevils fed streptavidin than for the controls ($P<0.001$, log-rank tests to compare survival curves). FIG. 39 shows the survival curves for data from the three replicates combined. As with the clover root weevils, Argentine stem weevil larvae that had received streptavidin appeared to have died during the moulting process and discarded head capsules were found adhering to the rear ends of dead larvae.

Conclusions:

Streptavidin has significant toxicity to the larvae of two plant-eating weevils, the clover root weevil. *S. lepidus*, and the Argentine stem weevil, *L. bonariensis*. This suggests that pasture plants expressing biotin-binding proteins in the roots or stems could be protected from attack by these pests.

TABLE 7

Median survival times for *S. lepidus* larvae (days). 95% confidence intervals in brackets

|  | Replicate 1 | Replicate 2 | Replicate 3 |
| --- | --- | --- | --- |
| Streptavidin Treatment | 14 (11–15) | 4 (4–6) | 4 (3–7) |
| Control | 24 (21–29) | 8 (4–18) | 16 (11–25) |

EXAMPLE 14

Feeding Trials with Adult Clover Root Weevils (*Sitona lepidus*) (Coleoptera: Curculionidae) fed with Avidin-painted Clover (*Trifolium repens*) Foliage Methods:

Adult *Sitona lepidus* were collected from a field at Ruakura Agricultural Research Centre, Hamilton, New Zealand, using a suction-powered insect-collecting device. They were then placed individually in clear plastic 30 mL containers ("Coulter cups") with vented lids, each containing a single painted leaf of white clover (*Trifolium repens*) with its stem embedded in about 10 mL of 0.4% agar in the bottom of the cup. This kept the leaf turgid for several days, while providing the weevil with a solid surface to walk on.

The avidin used in this trial was a Calbiochem® product, purchased from Calbiochem-Novabiochem Corporation, La Jolla, Calif. 92039. It was lyophilized avidin from egg white, Lot 276992.

As the upper surfaces of clover leaves are very hydrophobic, and *S. lepidus* adult weevils typically consume the entire leaf, only the undersides of the leaves were painted. The following solutions were applied with a small sable brush:

1. Controls were painted with 0.1% (v:v) BondXtra® (a wetting, spreading and sticking agent) at a rate of 80 $\mu$l solution per g of leaf (fresh weight).
2. "Low" avidin treatment leaves were painted with a 5 mg/mL avidin solution in 0.1% BondXtra® at the same rate as above. This rate approximates a leaf expressing 26 $\mu$M avidin.
3. "High" avidin treatment leaves were painted with a 10 mg/mL avidin solution in 0.1% BondXtra® at the same rate as above. This rate approximates a leaf expressing 52 $\mu$M avidin.

Between 15 and 18 adult weevils were placed on control leaves. 16 to 18 on low avidin-painted leaves and 16 to 18 on high avidin-painted leaves. The experiment was replicated three times (total of 149 weevils).

Weevils were examined and deaths recorded every weekday until all weevils had died.

Figure 40:
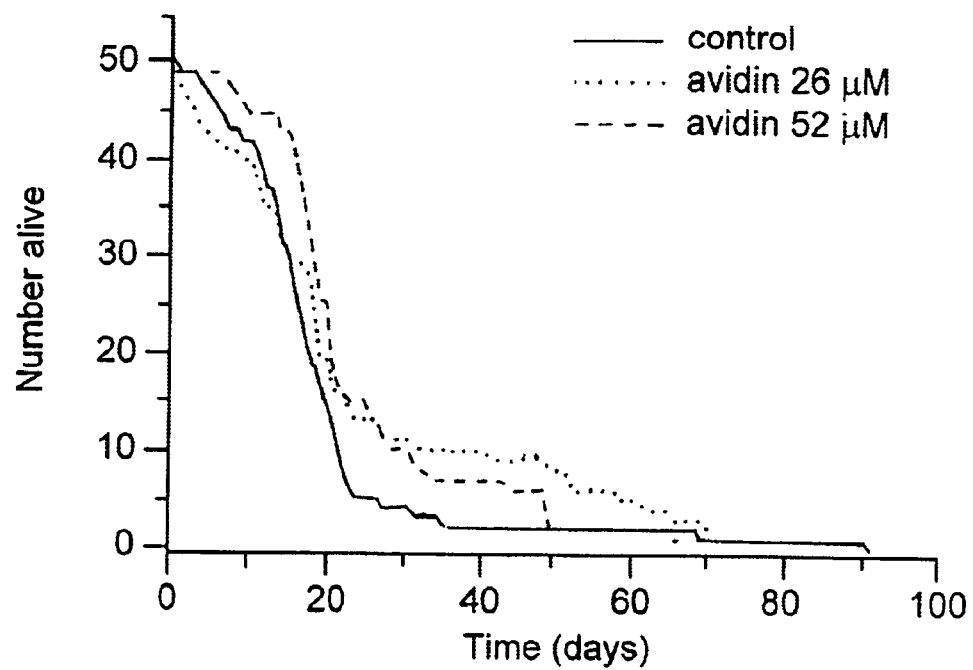
FIG. 40 shows the effect of avidin-painted clover leaves on the survival of adults of the clover root weevil, *Sitona lepidus*.

Results:

There were no significant differences among the survival curves for adult *S. lepidus* fed clover leaves painted with two doses of avidin or with a control solution without avidin (FIG. 40) (log-rank test, Kalbfleisch and Prentice, 1980).

Conclusions:

Avidin is not toxic to adult clover root weevils, *S. lepidus*, when painted onto clover leaves at approximately 26 or 52 $\mu$M. It is thus unlikely that transgenic clover plants expressing avidin at these levels will have toxicity to the adult stage of this weevil.

EXAMPLE 15

Feeding Trials with Adult Honeybees, *Apis mellifera* (Hymenoptera: Apidae), and Artificial Diet Containing Avidin Method:

Young adult honeybees were collected as they emerged from frames of capped bee brood taken from hives kept at our apiary in Auckland, New Zealand.

The avidin used in this trial was a Calbiochem® product, purchased from Calbiochem-Novabiochem Corporation, La Jolla, Calif. 92039. It was lyophilized avidin from egg white, Lot 276992.

Bees were assigned randomly to wooden cages (9×8×7 cm) with mesh on two sides, 30 bees per cage. Each cage was fitted with two gravity feeders, one containing water and the other sugar syrup (60% w:v sucrose solution). These were replenished as necessary during the experiment.

Each cage was also provided with a small cup containing a mixture of bee-collected pollen (1 part) and sugar candy (2 parts) (candy recipe: Ambrose, 1992) to which avidin had been added at two different concentrations. One group of cages was supplied with pollen/candy to which 0.1 mg avidin per g of pollen had been added (equivalent to approximately 6.7 $\mu$M avidin) and a second group was supplied with a mixture containing 0.3 mg avidin per g of pollen (equivalent to approximately 20 $\mu$M avidin). A third set of bees (controls) received pollen/candy without additive. The trial was replicated four times. i.e. a total of 12 cages of bees.

To measure consumption of the pollen/candy food by the bees, each cup was weighed at the start of the experiment and again at Days 8 and 14. Each cage was checked daily for bee deaths.

Figure 41:
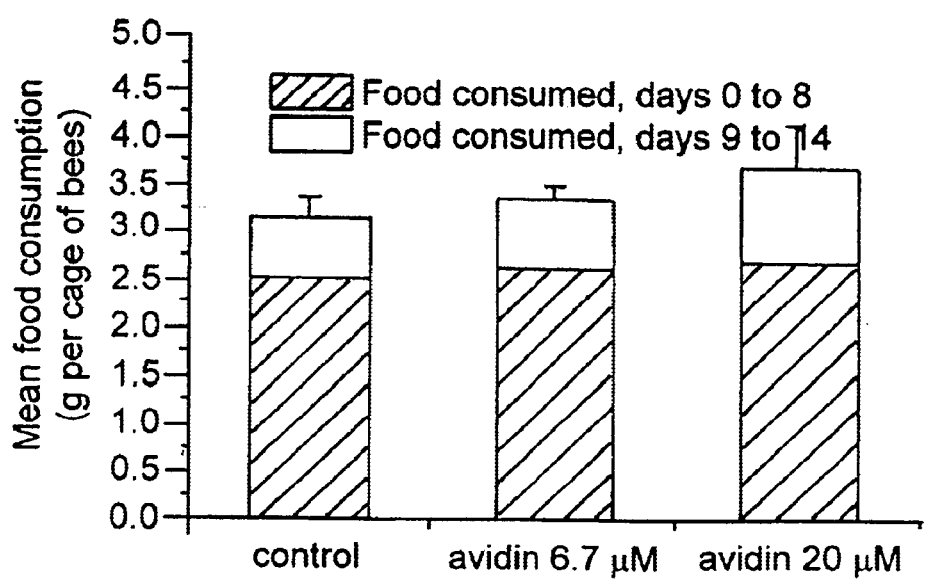
FIG. 41 shows the effect of avidin added to pollen on the consumption of that food by adult honeybees, *Apis mellifera*.

Results:

There were no significant differences in the mean quantities of pollen/candy consumed by the three groups of bees (ANOVA) over the first 8 days of exposure to the foods, between Days 8 and 14, or over the entire 14-day period (FIG. 41).

Figure 42:
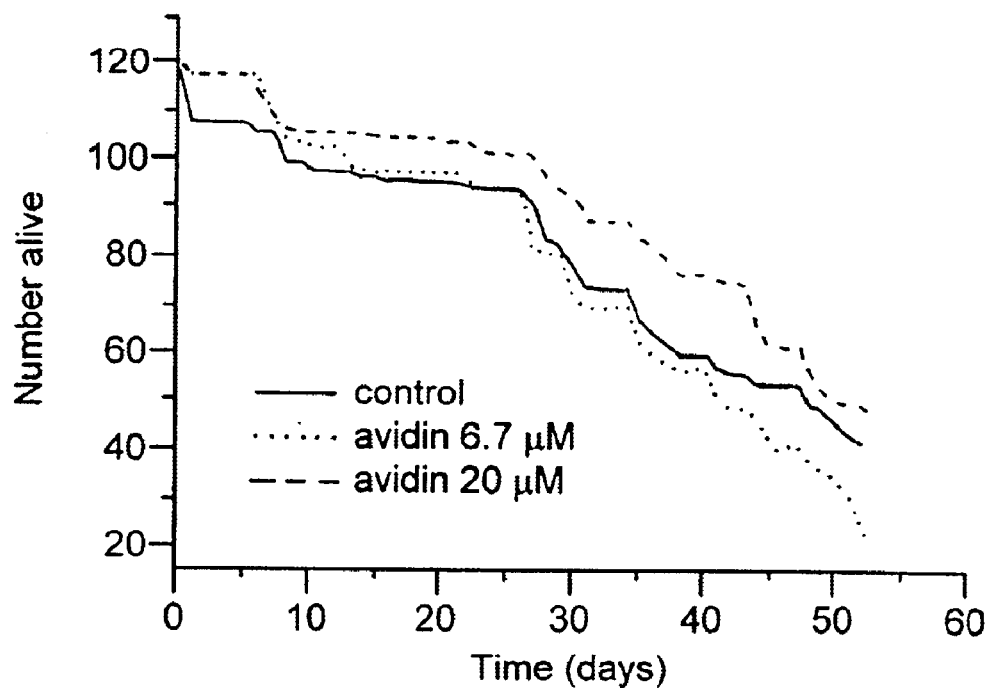
FIG. 42 shows the effect of avidin added to pollen on the survival of adult honeybees. *Apis mellifera*.

Comparisons of survival curves using log-rank tests (Kalbfleisch and Prentice, 1980) showed that bees fed the higher dose of avidin had significantly better survival ($P<0.002$) than those fed the lower dose. Control bee survival was intermediate between, and did not differ significantly from, that of bees fed either avidin dose (FIG. 42).

Conclusions:

Adult honeybees readily consume pollen/candy mixtures containing approximately 6.7 or 20 $\mu$M avidin and, when compared with control bees, their survival is unaffected by this consumption. This suggests that if biotin-binding proteins are expressed at these levels in pollen from plants modified to contain these genes, then young adult bees will not be repelled or harmed by such pollen.

EXAMPLE 16

Feeding Trials with Slugs (*Deroceras Reticulatum*) (Stylommatophora: Agriolimacidae) and Snails (*Cantareus aspersus*) (Stylommatophora: Helicidae) Fed with Avidin Painted onto Lettuce (*Latuca saliva*) Foliage Methods:

Snails and slugs were collected from local gardens (Auckland, New Zealand), weighed and placed in groups in sealed plastic containers (220×160×40 mm) with organically-grown lettuce leaves coated thoroughly with one of the following treatments:

1. Controls were painted with 0.1% (v:v) BondXtra® (a wetting spreading and sticking gent) only;
2. 4.8 $\mu$M avidin treatment leaves were painted with an avidin solution in 0.1% BondXtra® that delivered 75 $\mu$g of avidin per g fresh weight of lettuce;
3. 19.2 $\mu$M avidin treatment leaves were painted with an avidin solution in 0.1% BondXtra® that delivered 300 $\mu$L of avidin per g fresh weight of lettuce.

Each container was checked daily for deaths, the interior sprayed with water mist and the painted lettuce replenished as necessary. At the end of the experiment (after 51 days) all surviving animals were weighed.

Snails:

Snails were individually identified with a number written on their shells with permanent marker pen. Two containers of ten snails each were set up for each treatment (Le. 3 treatments×2 containers×10 snails=60 snails total). Each snail was weighed at the beginning of the experiment and the survivors also weighed at the end.

Slugs:

Five containers, each containing five slugs, were set up for each of the three treatments (i.e. 3 treatments×5 containers×5 slugs=75 slugs total). As slugs could not be individually marked, all five from each container were weighed together at the be beginning of the experiment. Surviving slugs were weighed individually at the end of the experiment.

Figure 43:
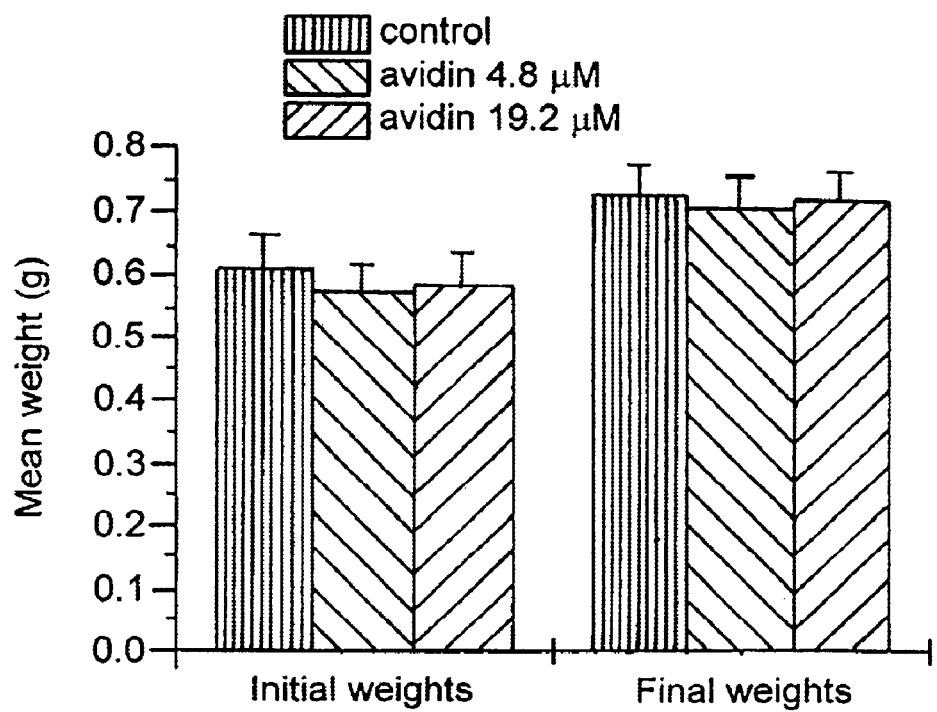
FIG. 43 shows the effect of avidin-painted lettuce leaves on the weights of snails, *Cantareus aspersus*.

Results:

Snails:

The three groups of snails used in the experiment had similar initial weights (ANOVA, FIG. 43). All snails grew during the 51-day experiment and there were no significant differences in final weights among the three groups (ANOVA, FIG. 43).

Figure 44:
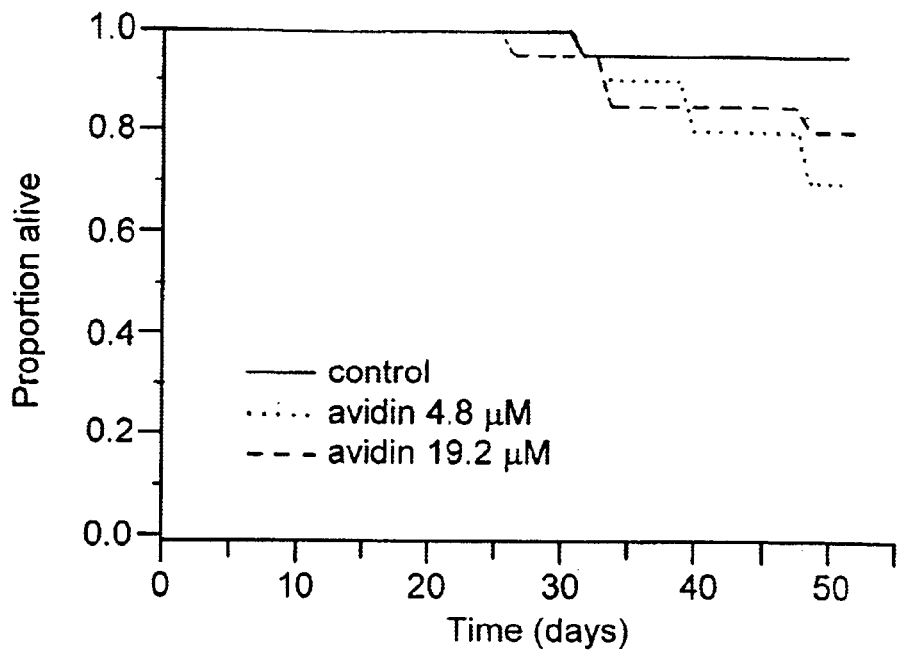
FIG. 44 shows the effect of avidin-painted lettuce leaves on the survival of snails, *Cantareus aspersus*.

Few snails died during the experiment (FIG. 44). There were no significant differences in mean snail longevity among the three groups (ANOVA, a 51-day longevity was assumed for all snails alive at the end of the experiment. i.e. an underestimate).

Figure 45:
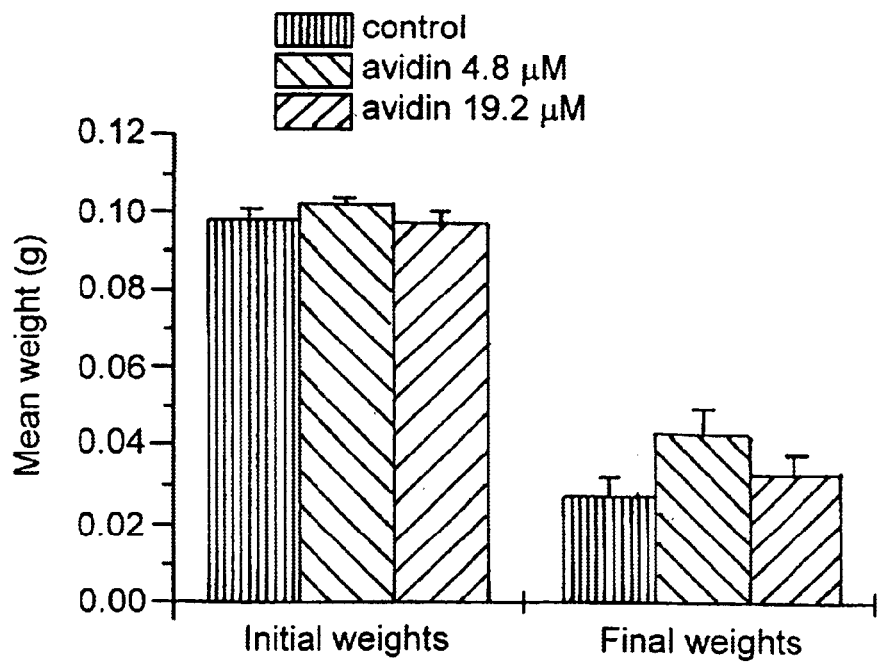
FIG. 45 shows the effect of avidin-painted lettuce leaves on the weight of slugs, *Deroceras reticulatum*.
Figure 48:
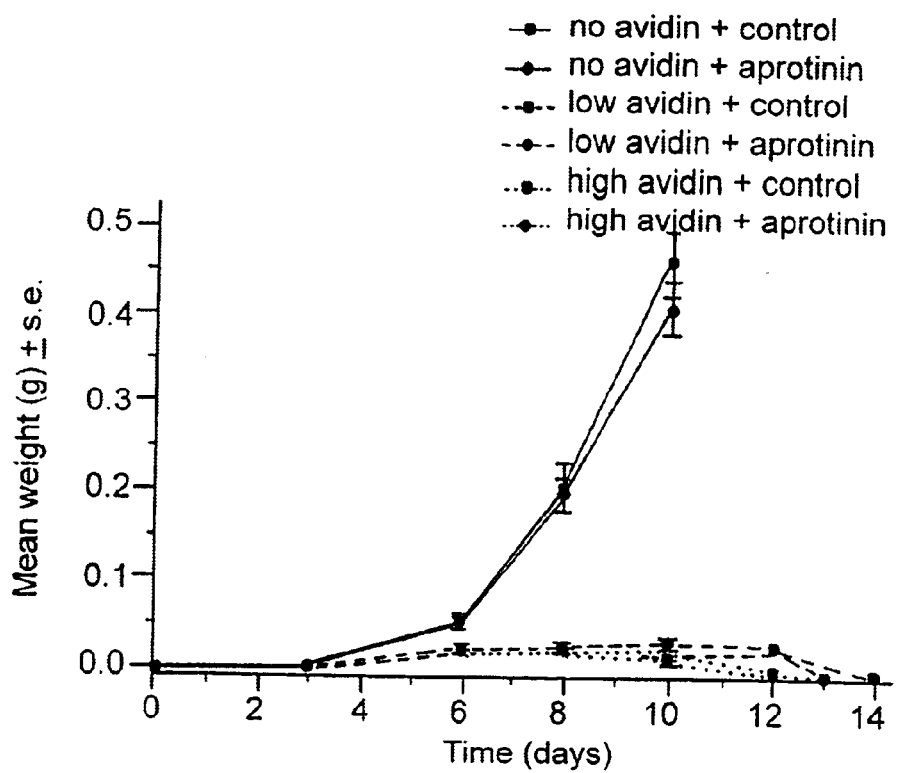
FIG. 48 shows the effect of avidin expression in tobacco combined with painted-on aprotinin on growth of larvae of the cotton bollworm (corn earworm, tomato fruitworm), *Helicoverpa armigera*.
Figure 49:
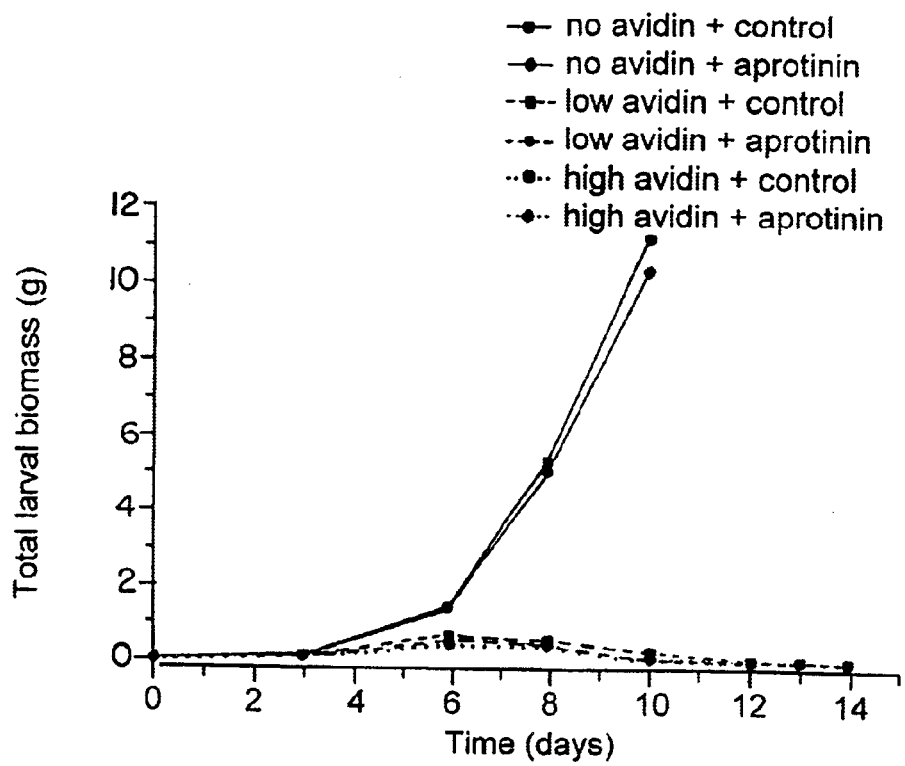
FIG. 49 shows the effect of avidin expression in tobacco combined with painted-on aprotinin on biomass of larvae of the cotton bollworm (corn earworm, tomato fruitworm), *Helicoverpa armigera*.

Slugs:

Initial weights of slugs were also similar across the three groups, but either lettuce must have been a poor diet for them or the conditions in their containers did not favour their development, because all slugs lost weight during the experiment (FIG. 45). There were no significant differences attributable to the treatments in initial or final mean slug weights (ANOVA).

Slug survival, particularly among the controls, was also poor under these experimental conditions (FIG. 46). In fact slugs on lettuce painted with either 4.8 $\mu$M or 19.2 $\mu$M avidin had significantly greater mean longevity than the control slugs (ANOVA, P=0.040, assuming all surviving slugs at the end of the experiment had a longevity of 51 days).

Conclusions:

Avidin had no effect on snail growth or survival when applied to their lettuce leaf food at 4.8 $\mu$M or 19.2 $\mu$M for a period of 51 days.

Slug results were confounded by poor growth of all slugs and poor survival of controls during the trial. However, avidin had no obvious toxicity to these invertebrates over a 51-day period of receiving lettuce painted with 4.8 $\mu$M or 19.2 $\mu$M of this protein.

EXAMPLE 17

Evaluation of Resistance of Tobacco (*Nicotiana tabacum*) Plants Expressing Avidin to Three Species of Root-knot Nematodes Methods:
Plants:

Tobacco seedlings were germinated either from non-transgenic (NT) seed or from seed collected from three independent selfed original transformant plants (PLA2/1, PLA2/4 and PLA2/24).

Avidin Expression Levels:

Twenty five control and 25 transgenic seedlings were transferred individually to 60-mm-diameter plastic pots of peat based porting mix and left to grow for a week before leaf samples were taken for ELISA analysis of gene expression (Example 5).

Avidin levels in both roots and leaves were measured earlier in 14 transgenic seedlings (from selfed independent oringinal transformants PLA2/7, PLA2/9 and PLA2/13) and two non-transgenic plants. Levels of avidin varied between 0 and 2.23 $\mu$M in roots and 0 and 16.84 $\mu$M in leaves. There was a linear correlation between leaf and root avidin levels in individual plants (n=16, $R^2$=0.716). Leaf avidin levels were subsequently used to select experimental material since it is not possible to harvest and measure root material prior to assay. Biotin concentrations in these plants were independent of avidin expression, being 0.05 $\mu$M in root tissue and 0.7 $\mu$M in leaves.

Nematodes:

Twenty highly expressing PLA2 plants and 20 non-transgenic plants were re-potted into 100-mm-diameter pots and a week later inoculated with a suspension 4000 eggs of root-knot nematodes injected into holes around the roots (method described in Sasser and Carter 1985). The nematode species used were *Meloidogyne javanica*, *Meloidogyne hapla* and *Meloidogyne incognita*. Control plants were injected with water. Thus, the design was 3 nematode species+1 control=4 inoculation types X2 Gene categories X5 replicates=40 pots.

After seven weeks, roots were washed free of potting mix and the galls counted. Roots and galls were then crushed with a small roller and extracted in chlorine solution to free the eggs, which were sieved out and counted.

Results:

The levels of avidin in the transgenic plants were 11.4±6.8 $\mu$M (range 2.4–26.05). Even at the lowest avidin level a six-fold molar excess of avidin over biotin can be calculated. There were no significant differences between means of gall and egg counts for each of the three root-knot nematode species (P>0.10) (ANOVA. Sokal and Rohlf 1969) (Table 8). No galls were seen on sham inoculated plants.

Conclusion:

Transgenic tobacco expressing high levels of avidin in root tissue is not resistant to root-knot nematode attack.

TABLE 8

Number of eggs laid and galls formed on tobacco roots by three species of nematodes.

| | M. javanica | | | | | M. hapla | | | | | M. incognita | | | |
| --- | --- | --- | --- | --- | --- | --- | --- | --- | --- | --- | --- | --- | --- | --- |
| Plant | Galls | Mean (s.e.) | Eggs | Mean (s.e.) | Plant | Galls | Mean | Eggs | Mean (s.e.) | Plant | Galls | Mean (s.e.) | Eggs | Mean |
| NT | | | | | NT | | | | | NT | | | | |
| 1 | 209 | | 0 | | 8 | 208 | | 87 | | 9 | 28 | | 0 | |
| 2 | 185 | | 63 | | 10 | 249 | | 0 | | 15 | 14 | | 41 | |
| 3 | 127 | | 0 | | 14 | 256 | | 22 | | 21 | 22 | | 20 | |
| 13 | 222 | | 0 | | 16 | 251 | | 0 | | 22 | 17 | | 34 | |
| 17 | 112 | 171 (22) | 56 | 24 (15) | 20 | 247 | 242 (9) | 0 | 22 (17) | 23 | 51 | 26 (7) | 0 | 19 (8) |
| PLA2/ | | | | | PLA2/ | | | | | PLA2/ | | | | |
| 1/6 | 139 | | 17 | | 24/9 | 149 | | 34 | | 1/7 | 30 | | 16 | |
| 4/1 | 175 | | 42 | | 24/11 | 216 | | 26 | | 4/8 | 21 | | 0 | |
| 24/1 | 74 | | 16 | | 24/12 | 197 | | 65 | | 4/14 | 22 | | 0 | |
| 24/4 | 89 | | 27 | | 24/14 | 189 | | 115 | | 24/5 | 16 | | 25 | |
| 24/7 | 127 | 121 (18) | 0 | 20 (7) | 4/24 | 277 | 206 (21) | 62 | 60 (16) | 24/8 | 32 | 24 (3) | 18 | 12 (5) |

EXAMPLE 18

Combined Toxic Effects of Avidin Expressed in Tobacco (*Nicotiana tabacum*) Leaves Painted with Either a Protease Inhibitor or a Bt Insecticidal Protein to Larval *Helicoverpa armigera* (Lepidoptera: *Noctuidae*): Bt and Avidin act Synergistically Constructs:
Control lines:
Non-transformed control plants:

Two hundred and forty one plants (NT 201-NT 441) were grown from seeds produced by selfed NT plant 11 which was used in the trial described in Example 8.

Avidin-expressing lines:
Selfed $T_2$ avidin-expressing generation

Tobacco plants were grown from seeds collected from three of the plants used in the trial described in Example 9. These parent plants were selfed (self-fertilised) and were the $T_1$ offspring of plants from the original transformant ($T_0$) plant lines PLA2/7, PLA2/9 and PLA2/13 used in the trial described in Example S. The plants used in this trial were thus second-generation (T$_2$) selfed plants derived from plants which had been transformed with the avidin gene with a PPI-I targeting sequence (Example 2).

Ninety eight plants from the PLA2/7 #18 line, 99 from the PLA2/9 #24 line and 126 from the PLA2/13 #22 line were grown for the experiment.

On each plant used in the experiment, Leaf 1 was designated as the uppermost (youngest) leaf which was 8 cm or more in length from leaf tip to junction of leaf base with the petiole. The leaves below Leaf 1 were assigned numbers consecutively down the plant Leaves 1, 2 and 3 were used for *H. armigera* feeding, as previous experiments had shown larvae grow best on young leaves.

Insecticidal Proteins:

Two purified insecticidal proteins were painted onto tobacco foliage in this experiment:

*Bacillus thuringiensis* insecticidal protein, Cry1Ba Activated Cry1Ba toxin was obtained from a large-scale fermentation of *B. thuringiensis* Bt4412, purified and cleaved according to the method described by Simpson et al. (1997).

Protease inhibitor, aprotinin, obtained from Intergen® Company, Canada/USA (Product No. 7105, Lot No. NT59808).

Insects:

*H. armigera* were obtained from a laboratory colony reared on artificial diet as described in McManus and Burgess (1995) and established from moths collected in Christchurch, New Zealand.

Neonate *H. armigera* larvae were placed on artificial diet for 48 h following emergence from eggs. These late first instar larvae were then placed on tobacco leaves as described below. Initial larval weight was determined as the mean of the individual weights of a randomly chosen sample of 54 of the larvae used in the trial.

Determination of Avidin Expression Levels:

Before commencing the experiment, a whole leaf sample comprising a leaf of at least 8 cm in length was taken from the 263 of the 323 avidin-expressing plants which had grown the best over an eight week period. Eighty nine PLA2/7 #18 plants, 71 PLA2/9 #24 plants and 103 PLA2/13 #22 plants were tested for avidin expression level using the ELISA assay described in Example 5. The plants were then ranked according to avidin expression level. Plants from the top of the table were then used in treatments requiring "high" expressors and those from the bottom of the table used where "low" expressors were required.

Trial Design:

Larvae were subjected to nine different treatments to test the effects of avidin, aprotinin and Cry1Ba separately and in two-way combinations. Each leaf was weighed before painting, and all solutions were applied at a rate of 100 µL solution per g of fresh leaf. To ensure leaves remained turgid, the petiole of each cut leaf was immersed in a setting solution of 0.4% w:v agar in a 30 mL coulter cup.

Treatments:

Control tobacco leaves painted with a control solution of 0.1% (v:v) BondXtra® (a wetting, spreading and sticking agent).

Control tobacco leaves painted with a 2 mg/ml solution of aprotinin in 0.1% (v:v) BondXtra® at the same rate as above. If tobacco leaves are about 2% protein, then this rate approximates a leaf expressing aprotinin as 1% of total soluble protein.

Control tobacco leaves painted with a 1 mg/ml solution of Cry1Ba in 0.1% (v:v) BondXtra® at the same rate as above. If tobacco leaves are about 2% protein, then this rate approximates a leaf expressing Cry1Ba as 0.5% of total soluble protein.

Tobacco leaves expressing avidin at a "low" level (see below) and painted with 0.1% (v:v) BondXtra®

Tobacco leaves expressing avidin at a "low" level and painted with a 2 mg/ml solution of aprotinin in 0.1% (v:v) BondXtra®

Tobacco leaves expressing avidin at a low" level and painted with a 1 mg/ml solution of Cry1Ba in 0.1% (v:v) BondXtra®

Tobacco leaves expressing avidin at a "high" level (see below) and painted with 0.1% (v:v) BondXtra®

Tobacco leaves expressing avidin at a "high" level and painted with a 2 mg/ml solution of aprotinin in 0.1% (v:v) BondXtra®

Tobacco leaves expressing avidin at a "high" level and painted with a 1 mg/ml solution of Cry1Ba in 0.1% (v:v) BondXtra®

The ranges of avidin expression levels in the plants used were as follows:

Treatment 4 ("low"): 2.12–5.27 µM
Treatment 5 ("low"): 2.62–5.30 µM
Treatment 6 ("low"): 3.62–5.24 µM
Treatment 7 ("high"): 12.95–21.27 µM
Treatment 8 ("high"): 12.90–21.00 µM
Treatment 9 ("high"): 14.18–18.10 µM Ten larvae were placed on the underside of each treated leaf inside a 300×210×80 mm plastic storage box lined with paper towels and with a snap-on lid. Three replicate boxes were set up for each treatment, i.e. 27 boxes in total, 30 larvae per treatment (two of the treatments were inadvertently given 31 larvae). Larvae and leaves were checked daily, and leaves were replaced with identically treated fresh leaves from similar plants as necessary so that larvae could feed ad libitum.

The experiment was conducted in a controlled temperature room at 30±1° C. and 60% relative humidity, with a 16:8 h light:dark cycle.

Larval deaths were recorded on Day 2 and daily thereafter for 14 days or until or all had died if this occurred earlier. Larvae were weighed on Days 3, 6, 8, 10 and 12. Once larvae had begun to pupate in any treatment, larvae in that treatment were no longer weighed.

Results:

Survival curves for *H. armigera* in the nine different treatment groups are shown in FIG. 47. Log-rank tests (Kalbfleisch and Prentice, 1980) were used to compare median survival in the different treatments. The only treatment which did not reduce median survival time compared with control survival was that using aprotinin-painted control leaves.

The four treatments using leaves expressing avidin at both high and low levels, with and without aprotinin painted on, killed all larvae within 13 days. Death often occured during early larval instar moulting. Survival on all these treatments was significantly reduced in comparison with survival on control leaves with and without aprotinin (ANOVA P 25<0.001) (Payne etal. 1993). Median survival times on these four avidin-expressing treatments did not differ significantly from each other. Thus the effect on median larval survival of the combination of avidin expression and aprotinin was equivalent to the effect of avidin expression alone. However, closer examination of the survival curves for the "low avidin" and the "low avidin with aprotinin" reveals that they diverge between days 8 and 12. The proportion of larvae alive on the "low avidin with aprotinin" treatment is significantly lower on days 9, 10 and 11 (ANOVA P<0.05). This demonstrates that avidin can be combined with a protease inhibitor to produce a more toxic effect on larvae, even though the effect of the protease inhibitor alone may be subtle. Additionally, there is no suggestion of antagonism between the two types of resistance protein.

The three treatments in which Cry1Ba was painted onto the leaves killed all larvae within four days. Larvae feeding on high and low avidin-expressing leaves painted with Cry1Ba died significantly faster than those feeding on Cry1Ba-painted control leaves (ANOVA $P<0.001$). The effects on mean larval survival of both the high avidin/Cry1Ba and the low avidin/Cry1Ba combination treatments were greater than the sum of the effects of the high or low avidin expression alone and Cry1Ba painting alone. Thus synergistic effects were observed with these combinations.

Growth rates and biomass were plotted for larvae on all the non-Cry1Ba treatments. Larvae feeding on control plants painted with the control solution or the aprotinin solution grew and accumulated biomass exponentially, while those on all treatments expressing avidin at high or low levels failed to grow or accumulate substantial biomass (FIGS. 48 And 49). Because of the powerful effects of the avidin alone, it was not possible to measure any more subtle effects that the combination with aprotinin may have had on these two parameters.

Conclusions:

Synergistic toxic effects on *H. armigera* larvae were observed with combinations of avidin-expressing tobacco leaf and the Bt insecticidal protein. Cry1Ba.

This suggests strongly that plants containing chimeric genes and expressing both avidin and Bt will be highly effective in protecting the plants from pest attack. It is likely that such plants will be more toxic than those expressing either protein singly.

Avidin at both high and low expression levels when combined with aprotinin was as effective as avidin expression alone in killing larvae and preventing growth and biomass accumulation. During the latter part of the experiment, larval death was greater in the combined aprotinin/low avidin treatment than in the low avidin treatment alone. This demonstrates the possibility that additive or synergistic effects could occur between avidin or streptavidin and a protease inhibitor which reduces larval growth and survival. The absence of any antagonistic effects between the biotin binding protein and the protease inhibitor shows the compatibility of these two types of resistance factor.

It is likely that plants expressing avidin together with a second effective insecticidal protein employing a different mode of action will not only have greater toxicity, but also more durable resistance to pest attack than plants expressing or containing a Bt protein, a protease inhibitor or another type of pest resistance factor on its own.

REFERENCES

Argarana C. E., Kuntz, I. D., Birkens, Axel R., and Cantor C. R. (1986). Molecular Cloning and Nucleotide Sequence of the Streptavidin Gene Nucleic Acids research 14: 1871–1882.

Bayer E. A. Ben-Hur H., Wilchek M. (1990) Isolation and properties of streptavidin. Methods in Enzymology 184: 80–89.

Bednarek S Y, Wilkins T. A., Dombrowski J. E., Raikhel N V (1990) A carboxyl-terminal propeptide is necessary for proper sorting of barley lectin to vacuoles of tobacco. Plant Cell 1990 2:1145–1155.

Beuning L. L. Spriggs T. W., and Christeller J. T. (1994) Evolution of the Proteinase Inhibitor I Family and Apparent Lack of Hypervariability in the Proteinase Contact Loop. J. Mol. Evol. 39 (6): 644–654.

Boulter, D. (1993). Review Article Number 86. Insect Pest Control by Copying Nature using Genetically Engineered Crops. Phytochemistry 34: 1453–1466.

Broodryk, S. W. 1971. Ecological investigations on the potato tuber moth *Phthorimaea operculella* (Zeller) (Lepidoptera: Gelechiidae). Phytophylactica 3: 73–84.

Burgess, E. P. J., Main, C. S., Stevens, P. S., Gatehouse, A. M. R., Christeller, J. T. and Laing, W. A. 1993. Protease inhibitors active against porina caterpillar (*Wiseana cervinata*). *Proc. 6th Australasian Grassl. Invert. Ecoli. Conf.* 1993 (R. A., Prestidge, Ed.). AgResearch, Hamilton, New Zealand, 331–339.

Chrispeels, M. J. (1991). Sorting of Proteins in the Secretory System. Annu. Rev. Plant Physiol. Plant Mol. Biol. 42: 21–53.

Chrispeels M. J, Raihkel N V. Short peptide domains target proteins to plant vacuoles. Cell. 1992 Feb. 21; 68(4): 613–616.

Cleveland, T. E. Thornburg, R. W., and Ryan, C. A. (1987). Molecular Characterization of Wound-inducible Inhibitor I Gene from Potato and the Processing of its mRNA and Protein. Plant Mol. Biol. 8: 199–207.

Dadd, R. H. (1985). Nutrition:Organisms In: Comprehensive Insect Physiology, Biochemistry and Pharmacology (Kerkut G. A. and Gilbert, L. L.) Pergamon Press, NY Vol 4, p 313–390).

Ditta G., Stanfield S., Corbin D., and Helinski D. R. (1980) Broad Host Range DNA Cloning System for Gram-Negative Bacteria: Construction of a Gene Bank of *Rhizobium* meliloti. Proc Natl Acad Sci USA 77 (12): 7347–7351.

Donson J, Kearney C M, Hilf M E, Dawson W O (1991); Systematic expression of a bacterial gene by a tobacco mosaic virus-based vector. Proc Natl. Acad. Sci. USA., 88:7204–8.

Drombrowski J E, Raikhel N V. Protein targeting to the plant vacuole—a historical perspective. Braz J. Med. Biol. Res. 1996 April; 29(4): 413–430.

Gleave A. P. (1992) A Versatile Binary Vector System with a T-DNA Organisational Structure Conducive to Efficient Integration of Cloned DNA into the Plant Genome. Plant Mol. Biol. 20 (6): 1203–1207.

Gleave, A. P., Mitra, D. S., Markwick, N. P., Morris. B. A. M. and Beuning, L. L. 1998. Enhancing the expression of the *Bacillus* thuringiensis cry9Aa2 gene in transgenic plants by nucleotide sequence modification. Molecular Breeding 4: 459–472.

Gope M. L., Keinanen R. A., Kristo P. A., Conneely O. M., Beattie W. G., Zarucki-Schulz T., O'Malley B. W. and Kulomaa M. S. (1987) Molecular Cloning of the Chicken Avidin cDNA. Nucleic Acids Res. 15 (8): 3595–3606.

Graham, J. S., Pearce, G., Merryweather, J. Titani, K., Ericsson L. H. and Ryan. C. A. (1985). Wound-induced Proteinase Inhibitors from Tomato Leaves. J. Biol. Chem. 260: 6561–6564.

Holwerda B C, Padgett H S. Rogers J C (1992) Proaleurain vacuolar targeting is mediated by short contiguous peptide interactions. Plant Cell 4:307–318.

James, C. and A. F. Krattiger (1996). Global Review of the Field Testing and Commercialisation of Transgenic Plants, 1986 to 1995: The First Decade of Crop Biotechnology. International Service for the Acquisition of Agri-Biotech Applications (ISAAA) Briefs No. 1.11) ISAAA: Ithaca, N.Y. pp 31.

Joshi R L, Joshi V, Ow D W (1990) BSMV genome mediated expression of a foreign gene in dicot and monocot plant cells. EMBO J. 9:2663–9.

Kalbfleisch, J. D. and Prentice, R. L. 1980. Statistical Analysis of Failure Time Data. John Wiley, New York.

Keinanen R A, Wallen M J, Kristo P A, Laukkanen M O, Toimela T A, Helenius M A, Kulomaa M S Molecular cloning and nucleotide sequence of chicken avidin-related genes. 1–5. Eur. J, Biochem. 220:615–621 (1994).

Keller, M., Sneh, B., Strizhov, N., Prudovsky, E., Regev, A., Koncz, C., Schell, J., Zilberstein, A. (1996): Digestion of delta-endotoxin by gut proteases may explain reduced sensitivity of advanced instar larvae of Spodoptera littoralis to CryIC. Insect Biochem. Mol. Biol 26: 365–73.

Kirsch T, Paris N, Butler J M, Beevers L, Rogers J C. Purification and initial characterization of a potential plant vacuolar targeting receptor. Proc. Natl. Acad. Sci. USA. 1994 Apr. 12; 91(8): 3403–3407.

Malone, L. A. and Wigley, P. J. 1990. A practical method for rearing Argentine stem weevil, Listronotus bonariensis (Coleoptera: Curculionidae) in the laboratory. N.Z Entomol. 13, 87–88.

Mariani, C., Goldberg R. B., Leemans, J. (1991), Engineered male sterility in plants. Symp. Soc. Exp. Biol. 45:271–9.

Martilla A T, Airenne K J, Laitinen O H, Kulik T. Bayer E A, Wilchek M, Kulomaa M S. Engineering of chicken avidin: a progressive series of reduced charge mutants. FEBS Letters 441: 313–317 (1998).

Matsuoka, K. Matsumoto, S., Hattori, T., Machida, Y., and Nakamura, K. (1990) Vacuolar Targeting and Posttranslational Processing of the Precursor to the Sweet Potato Tuberous Root Storage Protein in Heterologous Plant Cells. J. Biol. Chem. 265: 19750–19757.

Meisner, J., K. R. S. Ascher, and D. Lowie. 1974. Phagostimulants for the larva of the potato tuber moth, Gnorimoschema operculella Zell. Z. Angew. Entomol. 77: 77–106.

Michelmore, R, Marsh, E., Seely, S., and Benoit, L. (1987). Transformation of lettuce (Lactuca sativa) mediated by Agrobacterium tumefaciens. Plant Cell Reports 6:439–442.

Miller, D. W., et al., in Genetic Engineering (1986) Setlo W, J K et al., Eds, Plenum Publishing, Vol 8: pages 277–297).

Moore D. S., and Michael S. F. (1995) Mutagenesis of Amplified DNA Sequences Using Ampligase Thermostable DNA Ligase. Epicentre Forum 2 (4): 4–5.

Morgan, T. D., B. Oppert, T. H. Czapala, and K. J. Kramer (1993). Avidin and Streptavaidin as Insecticidal and Growth Inhibiting Dietary Proteins. Entomol. exp. appl. 69: 97–108.

Murray C. and Christeller J. T. (1994) Genomic Nucleotide Sequence of a Proteinase Inhibitor II Gene. Plant Physiol. 106: 1681.

Nakamura, K., and Matsuoka, K. (1993) Protein Targeting to the Vacuole in Plant Cells. Plant Physiol. 101: 1–5.

Neuhaus J M, Sticher L, Meins F Jr, Boller T (1991) A short C-terminal sequence is necessary and sufficient for the targeting of chitinases to the plant vacuole. Proc Natl Acad Sci USA 88:10362–10366.

Nielsen K J, Hill J M, Andersom M A, Craik D J. Synthesis and structure determination of NMR of a putative vacuolar targeting peptide and model of proteinase inhibitor from Nicotiana alata. Biochemistry. 1996 Jan. 16; 35(2): 369–378.

Rusch S L, Kendall D A. Protein transport via amino-terminal targeting sequences: common themes in diverse systems. Mol. Membr. Biol. 1995 October; 12(4): 295–307.

Saalbach G, Rosso M, Schumann U (1996) The vacuolar targeting signal of the 2S albumin from Brazil nut resides at the C terminus and involves the C-terminal propeptide as an essential element. Plant Physiol 112:975–985.

Sanchez-Serrano, J., Schmidt, R., Schell. J., and Willmitzer, L. (1986). Nucleotide Sequence of Proteinase Inhibitor II Encoding cDNA of Potato (Solanum tuberosum) and its Mode of Expression. Mol. Gen. Genet. 203: 15–20.

Schatz P J. (1993) Bio/Technology 11, 1138–1143

Schroder M R, Borkhsenious O W, Matsuoka K, Nakamura K Raikhel N V. Colocalization of barley lectin and sporamin in vacuoles of transgenic tobacco plants. Plant Physiol. 1993 February; 101(2): 451–458.

Seshagiri P B, Adiga P R (i987) Isolation and characterisation of a biotin-binding protein from the pregnant-rat serum and comparison with that from the chicken egg-yolk. Biochim Biophys Acta 916:474–481.

Shao, Z., Cui. Y., Liu, X., Yi, H., Ji, J., Yu, Z. (1998): Processing of delta-endotoxin of Bacillus thuringiensis subsp. Kurstaki HD-1 in Heliothis armigera midgut juice and the effects of protease inhibitors., J Invertebr. Pathol. 72: 73–81.

Subramanian N, Adiga P R (1995) Simultaneous purification of biotin-binding protein-I and -II from chicken egg yolk and their characterization. Biochem J 308:573–577.

Tague B W, Dickinson C D, Chrispeels M Y (1990) A short domain of the plant vacuolar protein phytohemagglutinin targets invertase to the yeast vacuole. Plant Cell 2:533–546.

Thompson L. D. and Weber P. C. (1993) Construction and Expression of a Synthetic Streptavidin-Encoding Gene in Escherichia coli. Gene 136: 243–246.

Torres, C., Cantliffe, D. J., Laughner, B., Bieniek, M. Nagata, R., Ashraf, M. and R. J. Feri (1993). Stable transformation of lettuce cultivar South Bay from cotyledon explants. Plant Cell, Tissue and Organ Culture 34: 279–285.

Turpen, T H. (1999) Tobacco mosaic virus and the virescence of biotechnology. Philos Trans. R Soc. Lond. Biol. Sci., 354: 665–73, 1999).

Vitale A, Chrispeels M J (1992) Sorting of proteins to the vacuoles of plant cells. Bioassays 14:151–160.

Von Heijne, G. (1983). Patterns of Amino Acids Near Signal-Sequence Cleavage Sites. Eur. J. Biochem. 133: 17–21.

Walker-Simmons, M., and Ryan, C. A. (1977). Immunological Identification of Proteinase Inhibitors I and II in Isolated Tomato Leaf Vacuoles. Plant Physiol. 60: 61–63.

Wilcheta M, Bayer EA. (eds) 1990. Avidin-Biotin Biotechnology. Methods of Enzymology Vol 184.

Zhang, X., and Conner, A. J. (1992). Genotypic effects on tissue culture response of lettuce cotyledons. J. Genet and Breed 46: 287–290.

All references are incorporated herein by reference.

What is claimed is:

1. An isolated nucleic acid molecule comprising:
   (i) a first nucleic acid sequence that encodes a vacuole targeting polypeptide operably linked to
   (ii) a second nucleic acid sequence that encodes a biotin binding protein selected from the group consisting of:
      (a) avidin; and
      (b) streptavidin.

2. The nucleic acid molecule of claim 1, wherein the vacuole targeting polypeptide is a potato proteinase inhibitor signal polypeptide.

3. The nucleic acid molecule of claim 2, wherein the vacuole targeting polypeptide is a potato proteinase inhibitor I signal polypeptide.

4. The nucleic acid molecule of claim 2, wherein the vacuole targeting polypeptide is a potato proteinase inhibitor II signal polypeptide.

5. The nucleic acid molecule of claim 1, wherein the biotin binding protein is avidin.

6. The nucleic acid molecule of claim 1, wherein the biotin binding protein is streptavidin.

7. The nucleic acid molecule of claim 6, wherein streptavidin is selected from the group consisting of: Core streptavidin, synthetic Core streptavidin, and SYNSAV.

8. The nucleic acid molecule of claim 6, wherein the streptavidin is encoded by the sequence set forth in SEQ ID NO:10.

9. The nucleic acid molecule of claim 1, wherein the vacuole targeting polypeptide is a potato proteinase inhibitor I polypeptide and the biotin binding protein is avidin.

10. The nucleic acid molecule of claim 1, wherein the vacuole targeting polypeptide is a potato proteinase inhibitor II signal polypeptide and the biotin binding protein is streptavidin.

11. The nucleic acid molecule of claim 1, wherein the vacuole targeting sequence is an N-terminal targeting polypeptide.

12. The nucleic acid molecule according to claim 1, wherein said nucleic acid molecule is a DNA molecule.

13. A vector comprising the nucleic acid molecule according to claim 12.

14. A host cell transformed with the vector according to claim 13.

15. The host cell according to claim 14, wherein said cell is a plant cell.

16. A method for producing a biotin-binding protein, said method comprising the steps of:

(a) culturing a host cell which has been transformed with a vector comprising the nucleic acid molecule according to claim 12 to produce an expressed biotin-binding protein; and (b) recovering the expressed biotin-binding protein.

17. A method for producing a pest resistant plant, said method comprising transforming the plant genome with at least one nucleic acid molecule according to claim 12, thereby producing a pest resistant plant.

18. A transgenic plant that comprises the nucleic acid molecule according to claim 12.

19. A transgenic plant expressing pesticidally effective concentrations of the biotin-binding protein, wherein the plant comprises the nucleic acid molecule according to claim 1.

20. A method for producing a biotin-binding protein, said method comprising extracting avidin or streptavidin from a plant transformed with the nucleic acid molecule according to claim 1.

21. Seed that is the product of the plant according to claim 18, wherein the seed comprises the nucleic acid molecule.

* * * * *

SEQUENCE LISTING

<160> NUMBER OF SEQ ID NOS: 18

<210> SEQ ID NO 1
<211> LENGTH: 324
<212> TYPE: DNA
<213> ORGANISM: Artificial Sequence
<220> FEATURE:
<223> OTHER INFORMATION: Description of Artificial Sequence:potato
      proteinase inhibitor I (PPI-I/pUC19)
<220> FEATURE:
<221> NAME/KEY: CDS
<222> LOCATION: (1)..(324)
<223> OTHER INFORMATION: PPI-I/pUC19

<400> SEQUENCE: 1
atggagtcaa agtttgctca catcattgtt ttctttcttc ttgcaacttc ctttgaaact     60
ctcttggcac gaaaagaaag tgatggacca gagatcttag aacttcaaaa ggaatttgaa    120
tgcaatggaa aacaaaggtg gccagaactt attggtgtac caacaaagct tgctaagggg    180
ataattgaga aggaaaattc actcataact aatgttcaga tactactgaa tggttctcca    240
gtcacaatgg attatcgttg taatcgagtt cgtctttttg ataacatttt gggtgatgtt    300
gtacaaattc ctagggtggc ttaa                                          324

<210> SEQ ID NO 2
<211> LENGTH: 576
<212> TYPE: DNA
<213> ORGANISM: Artificial Sequence
<220> FEATURE:
<223> OTHER INFORMATION: Description of Artificial Sequence:avidin cDNA
      (pGEMav)
<220> FEATURE:
<221> NAME/KEY: CDS
<222> LOCATION: (44)..(502)
<223> OTHER INFORMATION: avidin (pGEMav)
<220> FEATURE:
<221> NAME/KEY: sig_peptide
<222> LOCATION: (44)..(115)
<223> OTHER INFORMATION: signal sequence

<400> SEQUENCE: 2
gaattccgca aggagcacac ccggctgtcc acctgctgca gagatggtgc acgcaacctc     60
cccgctgctg ctgctgctgc tgctcagcct ggctctggtg ctcccggga tccctgccag    120 aaagtgctcg ctgactggga atggaccaa cgatctgggc tccaacatga ccatcggggc    180
tgtgaacagc agaggtgaat tcacaggcac ctacatcaca gccgtaacag ccacatcaaa    240
tgagatcaaa gagtcaccac tgcatgggac acaaaacacc atcaacaaga ggacccagcc    300 caccttggc ttcaccgtca attggaagtt ttcagagtcc accactgtct tcacgggcca    360
gtgcttcata gacaggaatg ggaaggaggt cctgaagacc atgtggctgc tgcggtcaag    420
tgttaatgac attggtgatg actggaaagc taccagggtc ggcatcaaca tcttcactcg    480
cctgcgcaca cagaaggagt gaggatggcc ccgcaaagcc agcaacaatg ccggagtgct    540
gacactgctt gtgatattcc tccccaataa agcttg                              576

<210> SEQ ID NO 3
<211> LENGTH: 401
<212> TYPE: DNA
<213> ORGANISM: Artificial Sequence
<220> FEATURE:
<223> OTHER INFORMATION: Description of Artificial Sequence:streptavidin
      cDNA (Streptavidin/pUC19)
<220> FEATURE:

```
<221> NAME/KEY: CDS
<222> LOCATION: (11)..(400)
<223> OTHER INFORMATION: streptavidin (Streptavidin/pUC19)

<400> SEQUENCE: 3
gaattcgcat atggctgaag ctggtatcac cggtacttgg tacaaccagc tggggtctac      60
cttcatcgtt accgctggtg ctgacggtgc actgaccggt acttacgaaa gcgctgttgg     120
taacgctgaa agccgttatg ttctgaccgg tcgttacgac tctgctccgg ctaccgacgg     180
ttctggtact gctctgggtt ggaccgttgc ttggaaaaac aactaccgta acgctcactc     240
tgctaccacc tggtctggcc agtacgttgg tggtgctgaa gctcgtatca acacccagtg     300
gctgctgacc tctggtacca ccgaagctaa cgcttggaaa tctaccctgg ttggtcacga     360
cacgttcacc aaagttaaac cgtctgctgc ttctatctag a                        401

<210> SEQ ID NO 4
<211> LENGTH: 584
<212> TYPE: DNA
<213> ORGANISM: Artificial Sequence
<220> FEATURE:
<223> OTHER INFORMATION: Description of Artificial Sequence:potato
      proteinase inhibitor II (PPI-II/pUC19)
<220> FEATURE:
<221> NAME/KEY: CDS
<222> LOCATION: (1)..(584)
<223> OTHER INFORMATION: PPI-II/pUC19
<220> FEATURE:
<221> NAME/KEY: sig_peptide
<222> LOCATION: (1)..(212)
<223> OTHER INFORMATION: signal sequence

<400> SEQUENCE: 4
atggatgttc acaaggaagt taatttcgtt gcttacctac taattgttct tggtaagatt      60
ttcctttact cctttgtttt aaaaaataaa aaacaaaaa aatcttggt ttatacatat      120 atatacacac aagtagtttt atttttttcc tttatattat atttgttgta ggaatatttc     180
tacttgttag cgtggtggaa catgttgatg cgaagatctg tactaaagaa tgtggtaatc     240
tgggttttgg gatatgccca cgttcagaag gaagtccgaa aaatcccata tgcatcaatt     300
gttgctcagg ctataagggt tgtaattatt atagtgtttt cgggagattt atttgcgaag     360
gagaatctga cctaaaaaac ccaaaagctt gccccctaaa ttgtgataca aatattgcct     420
attcaagatg cccccattca gaaggaaaat cgctaattta tcccaccgga tgtaccacat     480
gttgcacagg gtacaagggt tgctactatt tcggtaaaaa tggcaagttt gtatgcgaag     540
gagagagtga tgaacccaag gcaaatatgt accctgcaat gtga                     584

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence:altered Bam
      H I site

<400> SEQUENCE: 5
ggagatccaa ccatg                                                       15

<210> SEQ ID NO 6
<211> LENGTH: 486
<212> TYPE: DNA
<213> ORGANISM: Artificial Sequence
<220> FEATURE:
<223> OTHER INFORMATION: Description of Artificial Sequence:PPI-I/Avidin
```

-continued

```
      gene fusion
<220> FEATURE:
<221> NAME/KEY: CDS
<222> LOCATION: (1)..(486)
<223> OTHER INFORMATION: PPI-I/Avidin fusion protein

<400> SEQUENCE: 6
atggagtcaa agtttgctca catcattgtt ttctttcttc ttgcaactcc ctttgaaact    60
ctcttggcac gaaagaaag tgatggacca gagatccctg ccagaaagtg ctcgctgact    120
gggaaatgga ccaacgatct gggctccaac atgaccatcg gggctgtgaa cagcagaggt    180
gaattcacag gcacctacat cacagccgta acagccacat caaatgagat caaagagtca    240
ccattgcatg ggacacaaaa caccatcaac aagaggaccc agcccacctt tggcttcacc    300
gtcaattgga gttttcaga gtccaccact gtcttcacgg gccagtgctt catagacagg    360
aatgggaagg aggtcctgaa gaccatgtgg ctgctgcggt caagtgttaa tgacattggt    420
gatgactgga agctaccag ggtcggcatc aacatcttca ctcgcctgcg cacacagaag    480
gagtga                                                                486

<210> SEQ ID NO 7
<211> LENGTH: 161
<212> TYPE: PRT
<213> ORGANISM: Artificial Sequence
<220> FEATURE:
<223> OTHER INFORMATION: Description of Artificial Sequence:PPI-I/Avidin
      fusion protein

<400> SEQUENCE: 7

Met Glu Ser Lys Phe Ala His Ile Ile Val Phe Phe Leu Leu Ala Thr
  1               5                  10                  15

Pro Phe Glu Thr Leu Leu Ala Arg Lys Glu Ser Asp Gly Pro Glu Ile
                 20                  25                  30

Pro Ala Arg Lys Cys Ser Leu Thr Gly Lys Trp Thr Asn Asp Leu Gly
             35                  40                  45

Ser Asn Met Thr Ile Gly Ala Val Asn Ser Arg Gly Glu Phe Thr Gly
         50                  55                  60

Thr Tyr Ile Thr Ala Val Thr Ala Thr Ser Asn Glu Ile Lys Glu Ser
 65                  70                  75                  80

Pro Leu His Gly Thr Gln Asn Thr Ile Asn Lys Arg Thr Gln Pro Thr
                 85                  90                  95

Phe Gly Phe Thr Val Asn Trp Lys Phe Ser Glu Ser Thr Thr Val Phe
            100                 105                 110

Thr Gly Gln Cys Phe Ile Asp Arg Asn Gly Lys Glu Val Leu Lys Thr
        115                 120                 125

Met Trp Leu Leu Arg Ser Ser Val Asn Asp Ile Gly Asp Asp Trp Lys
    130                 135                 140

Ala Thr Arg Val Gly Ile Asn Ile Phe Thr Arg Leu Arg Thr Gln Lys
145                 150                 155                 160

Glu

<210> SEQ ID NO 8
<211> LENGTH: 626
<212> TYPE: DNA
<213> ORGANISM: Artificial Sequence
<220> FEATURE:
<223> OTHER INFORMATION: Description of Artificial
      Sequence:PPI-II/Streptavidin gene fusion
<220> FEATURE:
<221> NAME/KEY: CDS
```

```
<222> LOCATION: (1)..(626)
<223> OTHER INFORMATION: PPI-II/Streptavidin fusion protein
<220> FEATURE:
<221> NAME/KEY: modified_base
<222> LOCATION: (585)
<223> OTHER INFORMATION: n = g, a, c or t

<400> SEQUENCE: 8
atggatgttc acaaggaagt taatttcgtt gcttacctac taattgttct tggtaagatt      60
ttcctttact cctttgtttt aaaaaataaa aaaacaaaaa aaatcttggt ttatacatat     120
atatacacac aagtagtttt attttttttcc tttatattat atttgttgta ggaatatttc    180
tacttgttag cgtggtggaa catgttgatg cgaagatctg tactaagaat cgcatatgg     240 ctgaagctgg tatcaccggt acttggtaca accagctggg gtctaccttc atcgttaccg    300
ctggtgctga cggtgcactg accggtactt acgaaagcgc tgttggtaac gctgaaagcc    360
gttatgttct gaccggtcgt tacgactctg ctccggctac cgacggttct ggtactgctc    420
tgggttggac cgttgcttgg aaaaacaact accgtaacgc tcactctgct accacctggt    480
ctggccagta cgttggtggt gctgaagctc gtatcaacac ccagtggctg ctgacctctg    540
gtaccaccga agctaacgct tggaaatcta ccctggttgg tcacnacacg ttcaccaaag    600
ttaaaccgtc tgctgcttct atctag                                        626

<210> SEQ ID NO 9
<211> LENGTH: 168
<212> TYPE: PRT
<213> ORGANISM: Artificial Sequence
<220> FEATURE:
<223> OTHER INFORMATION: Description of Artificial
      Sequence:PPI-II/Streptavidin fusion protein

<400> SEQUENCE: 9

Met Asp Val His Lys Glu Val Asn Phe Val Ala Tyr Leu Leu Ile Val
  1               5                  10                  15

Leu Gly Ile Phe Leu Leu Val Ser Val Val Glu His Val Asp Ala Lys
                 20                  25                  30

Ile Cys Thr Lys Asn Ser His Met Ala Glu Ala Gly Ile Thr Gly Thr
             35                  40                  45

Trp Tyr Asn Gln Leu Gly Ser Thr Phe Ile Val Thr Ala Gly Ala Asp
 50                  55                  60

Gly Ala Leu Thr Gly Thr Tyr Glu Ser Ala Val Gly Asn Ala Glu Ser
 65                  70                  75                  80

Arg Tyr Val Leu Thr Gly Arg Tyr Asp Ser Ala Pro Ala Thr Asp Gly
                 85                  90                  95

Ser Gly Thr Ala Leu Gly Trp Thr Val Ala Trp Lys Asn Asn Tyr Arg
            100                 105                 110

Asn Ala His Ser Ala Thr Thr Trp Ser Gly Gln Tyr Val Gly Gly Ala
        115                 120                 125

Glu Ala Arg Ile Asn Thr Gln Trp Leu Leu Thr Ser Gly Thr Thr Glu
130                 135                 140

Ala Asn Ala Trp Lys Ser Thr Leu Val Gly His Asp Thr Phe Thr Lys
145                 150                 155                 160

Val Lys Pro Ser Ala Ala Ser Ile
                165

<210> SEQ ID NO 10
<211> LENGTH: 638
<212> TYPE: DNA
```

```
<213> ORGANISM: Streptomyces avidinii
<220> FEATURE:
<221> NAME/KEY: CDS
<222> LOCATION: (50)..(601)
<223> OTHER INFORMATION: streptavidin
<220> FEATURE:
<221> NAME/KEY: sig_peptide
<222> LOCATION: (50)..(121)
<223> OTHER INFORMATION: signal sequence

<400> SEQUENCE: 10
ccctccgtcc ccgccgggca acaactaggg agtattttc gtgtctcac atg cgc aag      58
                                                     Met Arg Lys
                                                       1 atc gtc gtt gca gcc atc gcc gtt tcc ctg acc acg gtc tcg att acg     106
Ile Val Val Ala Ala Ile Ala Val Ser Leu Thr Thr Val Ser Ile Thr
      5                  10                  15 gcc agc gct tcg gca gac ccc tcc aag gac tcg aag gcc cag gtc tcg     154
Ala Ser Ala Ser Ala Asp Pro Ser Lys Asp Ser Lys Ala Gln Val Ser
 20                  25                  30                  35 gcc gcc gag gcc ggc atc acc ggc acc tgg tac aac cag ctc ggc tcg     202
Ala Ala Glu Ala Gly Ile Thr Gly Thr Trp Tyr Asn Gln Leu Gly Ser
                 40                  45                  50 acc ttc atc gtg acc gcg ggc gcc gac ggc gcc ctg acc gga acc tac     250
Thr Phe Ile Val Thr Ala Gly Ala Asp Gly Ala Leu Thr Gly Thr Tyr
             55                  60                  65 gag tcg gcc gtc ggc aac gcc gag agc cgc tac gtc ctg acc ggt cgt     298
Glu Ser Ala Val Gly Asn Ala Glu Ser Arg Tyr Val Leu Thr Gly Arg
         70                  75                  80 tac gac agc gcc ccg gcc acc gac ggc agc ggc acc gcc ctc ggt tgg     346
Tyr Asp Ser Ala Pro Ala Thr Asp Gly Ser Gly Thr Ala Leu Gly Trp
     85                  90                  95 acg gtg gcc tgg aag aat aac tac cgc aac gcc cac tcc gcg acc acg     394
Thr Val Ala Trp Lys Asn Asn Tyr Arg Asn Ala His Ser Ala Thr Thr
100                 105                 110                 115 tgg agc ggc cag tac gtc ggc ggc gcc gag gcg agg atc aac acc cag     442
Trp Ser Gly Gln Tyr Val Gly Gly Ala Glu Ala Arg Ile Asn Thr Gln
                120                 125                 130 tgg ctg ctg acc tcc ggc acc acc gag gcc aac gcc tgg aag tcc acg     490
Trp Leu Leu Thr Ser Gly Thr Thr Glu Ala Asn Ala Trp Lys Ser Thr
            135                 140                 145 ctg gtc ggc cac gac acc ttc acc aag gtg aag ccg tcc gcc gcc tcc     538
Leu Val Gly His Asp Thr Phe Thr Lys Val Lys Pro Ser Ala Ala Ser
        150                 155                 160 atc gac gcg gcg aag aag gcc ggc gtc aac aac ggc aac ccg ctc gac     586
Ile Asp Ala Ala Lys Lys Ala Gly Val Asn Asn Gly Asn Pro Leu Asp
165                 170                 175 gcc gtt cag cag tag tcgcgtcccg gcaccggcgg gtgccgggac ctcggcc       638
Ala Val Gln Gln
180

<210> SEQ ID NO 11
<211> LENGTH: 183
<212> TYPE: PRT
<213> ORGANISM: Streptomyces avidinii

<400> SEQUENCE: 11

Met Arg Lys Ile Val Val Ala Ala Ile Ala Val Ser Leu Thr Thr Val
  1               5                  10                  15

Ser Ile Thr Ala Ser Ala Ser Ala Asp Pro Ser Lys Asp Ser Lys Ala
             20                  25                  30

Gln Val Ser Ala Ala Glu Ala Gly Ile Thr Gly Thr Trp Tyr Asn Gln
```

```
                35                  40                  45
Leu Gly Ser Thr Phe Ile Val Thr Ala Gly Ala Asp Gly Ala Leu Thr
 50                  55                  60

Gly Thr Tyr Glu Ser Ala Val Gly Asn Ala Glu Ser Arg Tyr Val Leu
 65                  70                  75                  80

Thr Gly Arg Tyr Asp Ser Ala Pro Ala Thr Asp Gly Ser Gly Thr Ala
                 85                  90                  95

Leu Gly Trp Thr Val Ala Trp Lys Asn Asn Tyr Arg Asn Ala His Ser
                100                 105                 110

Ala Thr Thr Trp Ser Gly Gln Tyr Val Gly Ala Glu Ala Arg Ile
            115                 120                 125

Asn Thr Gln Trp Leu Leu Thr Ser Gly Thr Thr Glu Ala Asn Ala Trp
130                 135                 140

Lys Ser Thr Leu Val Gly His Asp Thr Phe Thr Lys Val Lys Pro Ser
145                 150                 155                 160

Ala Ala Ser Ile Asp Ala Ala Lys Lys Ala Gly Val Asn Asn Gly Asn
                165                 170                 175

Pro Leu Asp Ala Val Gln Gln
            180
```

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:forward M13
      (lacZ) primer [Perkin Elmer]

<400> SEQUENCE: 12
gccagggttt tcccagtcac ga                                           22

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:reverse M13
      (lacZ) primer [Perkin Elmer]

<400> SEQUENCE: 13
gagcggataa caatttcaca cagg                                         24

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:avidin
      upstream primer

<400> SEQUENCE: 14
gcacacccgg ctgtccacct g                                            21

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence:PPI-I
      phosphorylated mutagenic primer
<220> FEATURE:
<221> NAME/KEY: modified_base
<222> LOCATION: (1)

-continued

```
<223> OTHER INFORMATION: n = 5' phosphorylated g

<400> SEQUENCE: 15
natggaccag agatcttaga ac                                            22

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:avidin
      phosphorylated mutagenic primer
<220> FEATURE:
<221> NAME/KEY: modified_base
<222> LOCATION: (1)
<223> OTHER INFORMATION: n = 5' phosphorylated g

<400> SEQUENCE: 16
ngctcccggg atccctgcca g                                             21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:PCR sense
      primer

<400> SEQUENCE: 17
ctgcaggtcg actctagagg a                                             21

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence:PCR
      antisense primer

<400> SEQUENCE: 18
ggtgaattct tagtacagat cttcgca                                       27
```